(12) United States Patent
Haines

(10) Patent No.: US 8,353,914 B2
(45) Date of Patent: Jan. 15, 2013

(54) METHODS AND APPARATUS FOR IMPROVED PROFILE BASED RESECTION

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 1558 days.

(21) Appl. No.: 11/825,857

(22) Filed: Jul. 9, 2007

(65) Prior Publication Data

US 2009/0076514 A1  Mar. 19, 2009

Related U.S. Application Data

(62) Division of application No. 11/075,553, filed on Mar. 8, 2005, now abandoned.

(60) Provisional application No. 60/551,160, filed on Mar. 8, 2004, provisional application No. 60/551,080, filed on Mar. 8, 2004, provisional application No. 60/551,078, filed on Mar. 8, 2004, provisional application No. 60/551,096, filed on Mar. 8, 2004, provisional application No. 60/551,631, filed on Mar. 8, 2004, provisional application No. 60/551,307, filed on Mar. 8, 2004, provisional application No. 60/551,262, filed on Mar. 8, 2004.

(51) Int. Cl.
*A61F 5/00* (2006.01)
(52) U.S. Cl. ........................................................ 606/87
(58) Field of Classification Search .................... 606/79, 606/82, 86 R, 87–89, 96; 623/20.14, 20.32, 623/20.35
See application file for complete search history.

(56) References Cited

U.S. PATENT DOCUMENTS

| | | | |
|---|---|---|---|
| 2,697,433 A | 12/1954 | Zehnder |
| 3,457,922 A | 7/1969 | Ray |
| 3,739,662 A | 6/1973 | Windelman et al. |
| 3,748,662 A | 7/1973 | Helfet |
| 3,774,244 A | 11/1973 | Walker |
| 3,798,679 A | 3/1974 | Ewald |
| 3,816,855 A | 6/1974 | Salch |
| 3,906,550 A | 9/1975 | Rostoker |
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,000,525 A | 1/1977 | Klawitter |

(Continued)

FOREIGN PATENT DOCUMENTS

EP  0104732  4/1984

(Continued)

OTHER PUBLICATIONS

Freeman Samuelson, *Total Knee System*, published by Biomet, Inc., 1994 ("Biomet Brochure") (Attached as Exhibit F).

(Continued)

*Primary Examiner* — Kevin T Truong
*Assistant Examiner* — Michael Araj
(74) *Attorney, Agent, or Firm* — Patterson Thuente Christensen Pedersen, P.A.

(57) ABSTRACT

Alignment guides, cutting guides, cutting tools and soft tissue management techniques for profile based resection (PBR) arthroplasty facilitate intraoperative and postoperative efficacy and ease of use. In one embodiment, a manual alignment guide is provided that permits less invasive incisions by providing soft tissue accommodating contours or reliefs. In another embodiment, a single medial drill guide plate is used for the PBR arthroplasty.

19 Claims, 51 Drawing Sheets

U.S. PATENT DOCUMENTS

| | | |
|---|---|---|
| 4,016,606 A | 4/1977 | Murray |
| 4,069,824 A | 1/1978 | Weinstock |
| 4,178,641 A | 12/1979 | Grundel |
| 4,207,627 A | 6/1980 | Cloutier |
| 4,213,209 A | 7/1980 | Insall |
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Peterson |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundei |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,808,185 A | 2/1989 | Penenberg |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,963,153 A | 10/1990 | Noesberger |
| 4,971,075 A | 11/1990 | Lee |
| 4,979,949 A | 12/1990 | Matsen |
| 4,986,833 A | 1/1991 | Worland |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr |
| 5,080,675 A | 1/1992 | Lawes |
| 5,092,869 A | 3/1992 | Waldron |
| 5,098,436 A | 3/1992 | Ferrante |
| 5,100,409 A | 3/1992 | Coates |
| 5,108,398 A | 4/1992 | McQueen |
| 5,112,336 A | 5/1992 | Krevolin |
| 5,116,375 A | 5/1992 | Hofmann |
| 5,122,144 A | 6/1992 | Bert |
| 5,129,907 A | 7/1992 | Heldreth |
| 5,129,909 A | 7/1992 | Sutherland |
| 5,133,758 A | 7/1992 | Hollister |
| 5,133,759 A | 7/1992 | Turner |
| 5,137,536 A | 8/1992 | Koshino |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,263,956 A | 11/1993 | Nobles |
| 5,269,786 A | 12/1993 | Morgan |
| 5,275,603 A | 1/1994 | Ferrante |
| 5,279,575 A | 1/1994 | Sugarbaker |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Peterson |
| 5,358,527 A | 10/1994 | Forte |
| 5,358,529 A | 10/1994 | Davidson |
| 5,358,531 A | 10/1994 | Goodfellow |
| 5,364,401 A | 11/1994 | Ferreante |
| 5,364,402 A | 11/1994 | Mumme |
| 5,370,699 A | 12/1994 | Hood |
| 5,370,701 A | 12/1994 | Finn |
| 5,391,170 A | 2/1995 | McGuire |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson, Jr. |
| 5,443,464 A | 8/1995 | Russell |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellow |
| 5,514,136 A | 5/1996 | Richelsoph |
| 5,514,139 A | 5/1996 | Goldstein |
| 5,514,143 A | 5/1996 | Bonutti |
| 5,520,694 A | 5/1996 | Dance |
| 5,520,695 A | 5/1996 | Luckman |
| 5,540,695 A | 7/1996 | Levy |
| 5,542,947 A | 8/1996 | Treacy |
| 5,549,683 A | 8/1996 | Bonutti |
| 5,549,684 A | 8/1996 | Amino |
| 5,549,688 A | 8/1996 | Ries |
| 5,551,429 A | 9/1996 | Fitzpatrick |
| 5,562,674 A | 10/1996 | Stalcup |
| 5,569,262 A | 10/1996 | Carney |
| 5,571,100 A | 11/1996 | Goble |

| Patent | Type | Date | Name |
|---|---|---|---|
| 5,578,039 | A | 11/1996 | Vendrely |
| 5,593,411 | A | 1/1997 | Stalcup |
| 5,597,379 | A | 1/1997 | Haines |
| 5,601,563 | A | 2/1997 | Burke |
| 5,601,566 | A | 2/1997 | Dance |
| 5,609,645 | A | 3/1997 | Vinciguerra |
| 5,611,802 | A | 3/1997 | Samuelson |
| 5,613,969 | A | 3/1997 | Jenkins, Jr. |
| 5,628,749 | A | 5/1997 | Vendrely |
| 5,639,279 | A | 6/1997 | Burkinshaw |
| 5,643,272 | A | 7/1997 | Haines |
| 5,649,928 | A | 7/1997 | Grundei |
| 5,653,714 | A | 8/1997 | Dietz |
| 5,658,293 | A | 8/1997 | Vanlaningham |
| 5,667,511 | A | 9/1997 | Vendrely |
| 5,681,354 | A | 10/1997 | Eckhoff |
| 5,682,886 | A | 11/1997 | Delp et al. |
| 5,690,632 | A | 11/1997 | Schwartz |
| 5,690,635 | A | 11/1997 | Matsen, III |
| 5,690,637 | A | 11/1997 | Wen |
| 5,697,935 | A | 12/1997 | Moran |
| 5,702,458 | A | 12/1997 | Burstein |
| 5,723,016 | A | 3/1998 | Minns |
| 5,725,530 | A | 3/1998 | Popken |
| 5,728,162 | A | 3/1998 | Eckhoff |
| 5,755,801 | A | 5/1998 | Walker |
| 5,755,803 | A | 5/1998 | Haines |
| 5,755,804 | A | 5/1998 | Schmotzer |
| 5,766,257 | A | 6/1998 | Goodman |
| 5,769,855 | A | 6/1998 | Bertin |
| 5,769,899 | A | 6/1998 | Schwartz |
| 5,776,200 | A | 7/1998 | Johnson |
| 5,782,921 | A | 7/1998 | Colleran |
| 5,782,925 | A | 7/1998 | Collaz |
| 5,799,055 | A | 8/1998 | Peshkin |
| 5,800,552 | A | 9/1998 | Forte |
| 5,810,827 | A | 9/1998 | Haines |
| 5,824,100 | A | 10/1998 | Kester |
| 5,824,102 | A | 10/1998 | Buscayret |
| 5,824,105 | A | 10/1998 | Ries |
| 5,871,545 | A | 2/1999 | Goodfellow |
| 5,871,546 | A | 2/1999 | Colleran |
| 5,879,354 | A | 3/1999 | Haines |
| 5,879,392 | A | 3/1999 | McMinn |
| 5,906,643 | A | 5/1999 | Walker |
| 5,908,424 | A | 6/1999 | Bertin |
| 5,925,049 | A | 7/1999 | Gustilo |
| 5,935,173 | A | 8/1999 | Roger |
| 5,944,758 | A | 8/1999 | Mansat |
| 5,954,770 | A | 9/1999 | Schmotzer |
| 5,980,526 | A | 11/1999 | Johnson |
| 5,986,169 | A | 11/1999 | Gjunter |
| 5,997,577 | A | 12/1999 | Herrington |
| 6,039,764 | A | 3/2000 | Pottenger |
| 6,056,754 | A | 5/2000 | Haines |
| 6,059,788 | A | 5/2000 | Katz |
| 6,068,658 | A | 5/2000 | Insall |
| 6,080,195 | A | 6/2000 | Colleran |
| 6,083,228 | A | 7/2000 | Michelson |
| 6,099,570 | A | 8/2000 | Livet |
| 6,110,182 | A | 8/2000 | Mowlai-Ashtiani |
| 6,120,543 | A | 9/2000 | Meesenburg |
| 6,132,468 | A | 10/2000 | Mansmann |
| 6,139,581 | A | 10/2000 | Engh |
| 6,165,223 | A | 12/2000 | Metzger |
| 6,171,340 | B1 | 1/2001 | McDowell |
| 6,195,577 | B1 | 2/2001 | Truwit |
| 6,197,064 | B1 | 3/2001 | Haines |
| 6,203,576 | B1 | 3/2001 | Afriat |
| 6,206,926 | B1 | 3/2001 | Pappas |
| 6,210,443 | B1 | 4/2001 | Marceaux |
| 6,235,060 | B1 | 5/2001 | Meesenburg |
| 6,236,875 | B1 | 5/2001 | Bucholz |
| 6,264,697 | B1 | 7/2001 | Walker |
| 6,285,902 | B1 | 9/2001 | Kienzle |
| 6,306,146 | B1 | 10/2001 | Dinkler |
| 6,306,172 | B1 | 10/2001 | O'Neil |
| 6,325,828 | B1 | 12/2001 | Dennis |
| 6,340,363 | B1 | 1/2002 | Bolger |
| 6,342,075 | B1 | 1/2002 | MacArthur |
| 6,348,058 | B1 | 2/2002 | Melkent |
| 6,361,564 | B1 | 3/2002 | Marceaux |
| 6,368,353 | B1 | 4/2002 | Arcand |
| 6,375,658 | B1 | 4/2002 | Hangody |
| 6,379,388 | B1 | 4/2002 | Ensign |
| 6,401,346 | B1 | 6/2002 | Roberts |
| 6,406,497 | B2 | 6/2002 | Takei |
| 6,413,279 | B1 | 7/2002 | Metzger |
| 6,430,434 | B1 | 8/2002 | Mittelstadt |
| 6,436,145 | B1 | 8/2002 | Miller |
| 6,443,991 | B1 | 9/2002 | Running |
| 6,458,128 | B1 | 10/2002 | Schulze |
| 6,470,207 | B1 | 10/2002 | Simon |
| 6,475,241 | B2 | 11/2002 | Pappas |
| 6,477,400 | B1 | 11/2002 | Barrick |
| 6,482,409 | B1 | 11/2002 | Lobb |
| 6,485,519 | B2 | 11/2002 | Meyers |
| 6,491,699 | B1 | 12/2002 | Henderson |
| 6,491,726 | B2 | 12/2002 | Pappas |
| 6,500,208 | B1 | 12/2002 | Metzger |
| 6,506,215 | B1 | 1/2003 | Letot |
| 6,520,964 | B2 | 2/2003 | Tallarida |
| 6,554,838 | B2 | 4/2003 | McGovern |
| 6,575,980 | B1 | 6/2003 | Robie |
| 6,579,290 | B1 | 6/2003 | Hardcastle |
| 6,595,997 | B2 | 7/2003 | Axelson, Jr. et al. |
| 6,620,198 | B2 | 9/2003 | Burstein |
| 6,623,526 | B1 | 9/2003 | Lloyd |
| 6,645,251 | B2 | 11/2003 | Salehi |
| 6,679,917 | B2 | 1/2004 | Ek |
| 6,685,711 | B2 | 2/2004 | Axelson |
| 6,694,168 | B2 | 2/2004 | Traxel |
| 6,694,768 | B2 | 2/2004 | Lu |
| 6,695,848 | B2 | 2/2004 | Haines |
| 6,697,664 | B2 | 2/2004 | Kienzle |
| 6,701,174 | B1 | 3/2004 | Krause |
| 6,702,821 | B2 | 3/2004 | Bonutti |
| 6,711,432 | B1 | 3/2004 | Krause et al. |
| 6,725,080 | B2 | 4/2004 | Melkent |
| 6,755,563 | B2 | 6/2004 | Wahlig |
| 6,755,835 | B2 | 6/2004 | Schultheiss |
| 6,755,864 | B1 | 6/2004 | Brack |
| 6,764,516 | B2 | 7/2004 | Pappas |
| 6,770,097 | B2 | 8/2004 | Leclercq |
| 6,773,461 | B2 | 8/2004 | Meyers |
| 6,783,550 | B2 | 8/2004 | MacArthur |
| 6,796,988 | B2 | 9/2004 | Malkent et al. |
| 6,827,723 | B2 | 12/2004 | Carson |
| 6,858,032 | B2 | 2/2005 | Chow |
| 6,875,222 | B2 | 4/2005 | Long |
| 6,886,684 | B2 | 5/2005 | Hacikyan |
| 6,898,858 | B1 | 5/2005 | Spell |
| 6,911,044 | B2 | 6/2005 | Fell |
| 6,916,324 | B2 | 7/2005 | Sanford |
| 6,916,340 | B2 | 7/2005 | Metzger |
| 6,942,627 | B2 | 9/2005 | Huitema |
| 6,942,694 | B2 | 9/2005 | Liddicoat |
| 7,018,418 | B2 | 3/2006 | Amrich |
| 7,029,477 | B2 | 4/2006 | Grimm |
| 7,048,741 | B2 | 5/2006 | Swanson |
| 7,060,074 | B2 * | 6/2006 | Rosa et al. ............ 606/88 |
| 7,077,867 | B1 | 7/2006 | Pope |
| 7,104,966 | B2 | 9/2006 | Shiber |
| 7,104,996 | B2 | 9/2006 | Bonutti |
| 7,141,053 | B2 | 11/2006 | Rosa |
| 7,172,596 | B2 | 2/2007 | Coon |
| 7,175,630 | B2 | 2/2007 | Farling |
| 7,241,298 | B2 | 7/2007 | Nemec |
| 7,326,252 | B2 | 2/2008 | Otto |
| 7,344,541 | B2 | 3/2008 | Haines |
| 7,371,240 | B2 | 5/2008 | Pinczewski |
| 7,422,605 | B2 | 9/2008 | Burstein |
| 7,491,235 | B2 | 2/2009 | Fell |
| 7,618,451 | B2 | 11/2009 | Fitz et al. |
| 7,922,771 | B2 | 4/2011 | Otto |
| 2001/0018615 | A1 | 8/2001 | Biegun |
| 2001/0044627 | A1 | 11/2001 | Justin |
| 2001/0049558 | A1 | 12/2001 | Liddicoat |

| | | | | | | |
|---|---|---|---|---|---|---|
| 2002/0055784 A1 | 5/2002 | Burstein | | GB | 1409150 | 10/1975 |
| 2002/0103541 A1 | 8/2002 | Meyers | | GB | 2007980 | 7/1982 |
| 2002/0107576 A1 | 8/2002 | Meyers | | GB | 2296443 | 7/1996 |
| 2002/0120340 A1 | 8/2002 | Metzger | | GB | 2324249 | 10/1998 |
| 2002/0161447 A1 | 10/2002 | Salehi | | GB | 2335145 | 9/1999 |
| 2002/0183760 A1* | 12/2002 | McGovern et al. ............ 606/88 | | JP | 02-501806 | 1/1983 |
| 2002/0198531 A1 | 12/2002 | Millard | | JP | 58-209343 | 12/1983 |
| 2003/0028196 A1 | 2/2003 | Bonutti | | JP | 61-170453 | 8/1986 |
| 2003/0055501 A1 | 3/2003 | Fell | | JP | 62-133948 | 6/1987 |
| 2003/0055509 A1 | 3/2003 | McCue | | JP | 62-254750 | 6/1987 |
| 2003/0060882 A1 | 3/2003 | Fell | | JP | 01-119244 | 5/1989 |
| 2003/0060883 A1 | 3/2003 | Fell | | JP | 01-126957 | 5/1989 |
| 2003/0060884 A1 | 3/2003 | Fell | | JP | 01-209055 | 8/1989 |
| 2003/0060885 A1 | 3/2003 | Fell | | JP | 02-057247 | 2/1990 |
| 2003/0069585 A1 | 4/2003 | Axelson | | JP | 02-234756 | 9/1990 |
| 2003/0069591 A1 | 4/2003 | Carson | | JP | 02-234757 | 9/1990 |
| 2003/0093156 A1 | 5/2003 | Metzger | | JP | 02-239861 | 9/1990 |
| 2003/0130665 A1 | 7/2003 | Pinczewski | | JP | 02-243143 | 9/1990 |
| 2003/0158606 A1 | 8/2003 | Coon | | JP | 02-246971 | 10/1990 |
| 2003/0181986 A1 | 9/2003 | Buchholz | | JP | 2002/274214 | 11/1990 |
| 2003/0208122 A1 | 11/2003 | Melkent | | JP | 03-032663 | 2/1991 |
| 2003/0212413 A1 | 11/2003 | Wilk | | JP | 04-297254 | 10/1992 |
| 2004/0039396 A1 | 2/2004 | Couture | | JP | 04-361746 | 12/1992 |
| 2004/0044414 A1 | 3/2004 | Nowakowski | | JP | 05-003880 | 1/1993 |
| 2004/0122305 A1 | 6/2004 | Grimm | | JP | 05-502814 | 5/1993 |
| 2004/0152970 A1 | 8/2004 | Hunter | | JP | 5-41510 | 6/1993 |
| 2004/0153066 A1 | 8/2004 | Coon | | JP | 05-269140 | 10/1993 |
| 2004/0199249 A1 | 10/2004 | Fell | | JP | 05-277130 | 10/1993 |
| 2004/0199250 A1 | 10/2004 | Fell | | JP | 06-08033 | 1/1994 |
| 2004/0249467 A1 | 12/2004 | Meyers | | JP | 06-38971 | 2/1994 |
| 2004/0249471 A1 | 12/2004 | Bindseil | | JP | 6-217984 | 8/1994 |
| 2004/0267363 A1 | 12/2004 | Fell | | JP | 06-233775 | 8/1994 |
| 2005/0033424 A1 | 2/2005 | Fell | | JP | 06-237941 | 8/1994 |
| 2005/0149038 A1 | 7/2005 | Haines | | JP | 7-501966 | 3/1995 |
| 2005/0149039 A1 | 7/2005 | Haines | | JP | 7-116185 | 5/1995 |
| 2005/0149040 A1 | 7/2005 | Haines | | JP | 7-136200 | 5/1995 |
| 2005/0171604 A1 | 8/2005 | Michalow | | RU | 2121319 | 11/1998 |
| 2005/0283251 A1 | 12/2005 | Coon | | SE | 382155 | 1/1976 |
| 2006/0015109 A1 | 1/2006 | Haines | | SU | 577020 T | 10/1977 |
| 2006/0015115 A1 | 1/2006 | Haines | | WO | WO 81/03122 | 11/1981 |
| 2006/0015116 A1 | 1/2006 | Haines | | WO | WO 91/00061 | 1/1991 |
| 2006/0015117 A1 | 1/2006 | Haines | | WO | WO 91/10408 | 7/1991 |
| 2006/0030853 A1 | 2/2006 | Haines | | WO | WO 93/22990 | 11/1993 |
| 2006/0030854 A1 | 2/2006 | Haines | | WO | WO 93/25157 | 12/1993 |
| 2006/0030855 A1 | 2/2006 | Haines | | WO | WO 94/05212 | 3/1994 |
| 2006/0030944 A1 | 2/2006 | Haines | | WO | WO 94/08528 | 4/1994 |
| 2006/0052875 A1 | 3/2006 | Bernero | | WO | WO 94/09730 | 5/1994 |
| 2006/0058882 A1 | 3/2006 | Haines | | WO | WO 94/14366 | 7/1994 |
| 2007/0078517 A1 | 4/2007 | Engh | | WO | WO 94/22397 | 10/1994 |
| 2007/0179607 A1 | 8/2007 | Hodorek | | WO | WO96/01588 | 1/1996 |
| 2008/0154270 A1 | 6/2008 | Haines | | WO | WO96/07361 A1 | 3/1996 |
| 2009/0082773 A1 | 3/2009 | Haines | | WO | WO 96/24295 | 8/1996 |
| 2009/0138018 A1 | 5/2009 | Haines | | WO | WO 97/05827 | 2/1997 |
| 2010/0191244 A1 | 7/2010 | White | | WO | WO97/29703 A1 | 8/1997 |
| | | | | WO | WO97/29704 A1 | 8/1997 |

FOREIGN PATENT DOCUMENTS

| | | |
|---|---|---|
| EP | 0121142 | 10/1984 |
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| WO | WO 9820817 | 5/1998 |
| WO | WO 99/27872 | 6/1999 |
| WO | WO 99/30649 | 6/1999 |
| WO | WO 01/13825 | 3/2001 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

Freeman, Mark II *Total Knee Replacement System*, published 1985 (Attached as Exhibit G).

Protek F/S Modular Total Knee Replacement System, pp. 1-57, published by Protek in Jan. 1991 (Attached as Exhibit H).

*Low Contact Stress Meniscal Bearing Unicompartmental Knee Replacement: Long-Term Evaluation of Cemented and Cementless Results*, Journal of Orthopaedic Rheumatology (presented at the 57th Annual American Academy of Orthpaedic Surgeons Meetings, New Orleans, LA, Feb. 11, 1990), Bates No. DEP00004096-DEP00004107.

N.J. Unicompartmental Knee, Dated Sep. 15, 1989, Bates No. DEP00004108-DEP00004116.

Buechel, Frederick F., *NJ LCS Unicompartmental Knee System with Porocoat*, dated Oct. 24, 1994, Bates No. DEP000004117-DEP00004130.

Buechel, Frederick F. *NJ LCS Unicompartmental Knee System with Porocoat*, 1994, Bates No. DEP00004131-DEP00004141.

Buechel, Frederick F. *NJ LCS Unicompartmental Knee System with Porocoat*, 1994, Bates No. DEP00004142-DEP00004152.

Engh, et al., *The AMK Total Knee System, Design Rationale and Surgical Procedure*, dated 1989, Bates No. DEP00004153-DEP00004201.

*Advertising Proteck Mark II PCR Total Knee Replacement System*, Journal of Bone and Joint Surgery, 1987, Bates No. DEP00004202-DEP00004230.

Protek, *Parts Brochure for Mark II Protek*,1987, Bates No. DEP00004231-DEP00004235.

Chapman, Michael W., *Operative Orthopaedics*, vol. 1, Published by J.B. Lipponcott Co., Philadelphia, dated 1988, Bates No. DEP00004236-DEP00004247.

American Academy of Orthopaedic Surgeons, *Flyer from 57th Annual American Academy of Orthopaedic Surgeons Meeting*, Feb. 13, 1990, Bates No. DEP00004248-DEP00004251.

Crossett et al., *AMK Congruency Instrument System, Surgical Technique*, dated 1997, Bates No. DEP00004252-DEP00004267.

Engh et al., *AMK Surgical Technique*, Bates No. DEP00004268-DEP00004298, dated 1989.

Engh et al., *AMK Surgical Technique*, Bates No. DEP00004299-DEP0004329, dated 1989.

Crenshaw, A.H., *Campbell's Operative Orthopaedics*, 4th Edition, vol. 1, Bates No. DEP00004330-DEP00004333, dated 1963.

Howmedica, *Duraconcept, Design Concepts of the Duracon Total Knee System*, Bates No. DEP00004337-DEP00004337, dated 1993.

Freeman et al., *Total Knee System*, Bates No. DEP00004350-DEP00004361, Published prior to Jun. 7, 1994.

Freeman et al., *F/S Modular Total Knee Replacement System-SICOT*, 90 Edition, Bates No. DEP00004362-DEP00004373, dated 1990.

Buechel, Frederick F., *Howmedica Product Catalog*, Bates No. DEP00004374-DEP00004375, dated 1994.

Massarella, Antony, *Interax Bulletin, No. 6, Tibial Intramedullary Alignment Surgical Technique*, Bates No. DEP00004387-DEP0000-4390, dated Feb. 23, 1994.

Desjardins et al., *Interax Operative Technique*, Bates No. DEP00004391-DEP00004411, dated 1994.

Desjardins et al., *Interax Total Knee Operative Technique: Monogram Total Knee Instruments*, Bates No. DEP00004412-DEP00004432, dated 1993.

Howmedica, *Interax Tibial IM*, Bates No. DEP00004433-DEP00004433, dated 1994.

Depuy, *LCS Uni PMA Data from FDA Website*, Bates No. DEP00004434-DEP00004434, dated 1991.

Briard et al., *LCS Uni Unicompartmental Knee System with Porocoat*, Bates No. DEP00004452-DEP00004462, dated 1991.

Freeman et al., *Mark II Total Knee Replacement System*, Bates No. DEP00004463-DEP00004492, dated 1985.

Buechel, Frederick F., *NJ LCS Unicompartmental Knee System with Porocoat*, Bates No. DEP00004493-DEP00004503, dated 1994.

Chapman, Michael W. *Operative Orthopaedics*, vol. 3, 2nd Edition, Published by J.B. Lipponcott Co., BATES No. DEP00004504-DEP00004508, dated 1993.

Biomet, *Oxford Meniscal Knee Phase II Unicompartmental Replacement*, Bates No. DEP00004509-DEP00004515, Published prior to Jun. 7, 1994.

Scott et al., *P.F.C. Sigma Unicompartmental Knee System*, Bates No. DEP00004531-DEP00004539, dated 1998.

Freeman et al., *F/S Modular Total Knee Replacement System*, Bates No. DEP00004540-DEP00004596, dated 1990.

Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates No. DEP00004752-DEP00004763.

Scott et al., *Unicompartmental and High Tibial Osteotomy for Osteoarthritis of the Knee*, Journal of Bone and Joint Surgery, vol. 63-A, No. 4, Apr. 1, 1981, Bates No. DEP00004764-DEP00004775.

Thornhill, Thomas S., *Unicompartmental Knee Arthroplasty Clinical Orthopaedics and Related Research*, No. 205, Apr. 1, 1986, pp. 121-131, Bates No. DEP00004776-DEP00004791.

Forst et al., *A Special jg for Tibial Resection for the Implantation of GSB-Knee-Prostheses in Problematic cases*, pp. 162-166, dated Jun. 1, 1984, Bates No. DEP00004838-DEP00004842.

Ingillis et al., *Revision Total Knee Replacement Techniques in Orthopedics*, dated Apr. 1, 1990, Bates No. DEP00005583-DEP00005592.

Uvehammer et al., "In Vivo Kinematics of Total Knee Arthroplasty: Concave Versus Posterior-Stabilised Tibial Joint Surface", vol. 82-B, No. 4, May 2000, pp. 499-505.

U.S. Appl. 12/638,692, filed Dec. 15, 2009, Haines.

T.D.V. Cooke et al., *Universal Bone Cutting Device for Precision Knee Replacement Arthroplasty and Osteotomy*, 7 J. Biomed. Eng'g 45, 47, col. 2, 11. 52-57 (1985).

E. Marlowe Goble and Daniel F. Justin, *Minimally invasive total knee replacement: principles and technique*, Orthop. Clin. N. Am. 35 (2004) 235-245.

Whiteside Ortholoc Total Knee System: Surgical Procedure, Dow Coming Wright, pp. WMT000001-WMT000040, Jun. 1985.

Zimmer, Insall/Burstein II, *Constrained Condylar: Modular Knee System*, 35 pages, copyright 1989.

File History for U.S. Appl. No. 12/187,210, filed Aug. 6, 2008.

File History for U.S. Appl. No. 11/075,842, filed Mar. 8, 2005.

File History for U.S. Appl. No. 11/075,828, filed Mar. 8, 2005.

U.S. Appl. No. 11/036,584, Inventor: Haines, filed Jan. 14, 2005.

File History for U.S. Appl. No. 11/075,840, filed Mar. 8, 2005.

U.S. Appl. No. 11/075,552, Inventor: Haines, filed Mar. 8, 2005.

File History for U.S. Appl. No. 11/049,634, filed Feb. 5, 2005.

File History for U.S. Appl. No. 11/074,599, filed Mar. 8, 2005.

File History for U.S. Appl. No. 11/075,553, filed Mar. 8, 2005.

U.S. Appl. No. 12/171,843, Inventor: Haines, filed Jul. 11, 2008.

File History for U.S. Appl. No. 11/075,836, filed Mar. 8, 2005.

Whiteside Ortholoc Total Knee System, Dow Corning Wright, pp. ZH000109679-ZH000109690, Aug. 2009.

Zimmer, Insall/Burnstein II, *Modular Knee System*, Surgical Technique, pp. ZH000109691-ZH000109710, Aug. 2009.

Zimmer, The Miller/Galante Advantage: Total Knee System, pp. ZH000156953-ZH000156968, Aug. 2009.

* cited by examiner

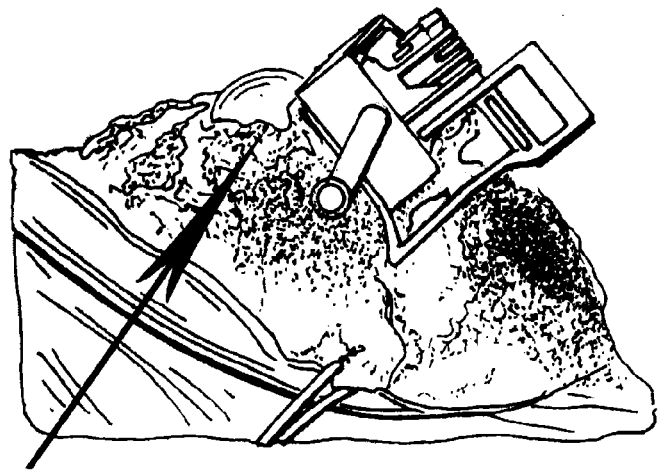
FEMUR  *Fig. 3A*
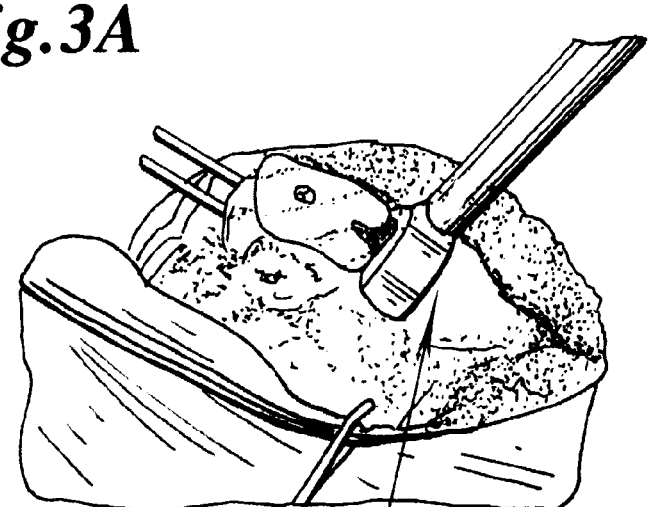
*Fig. 3B*  TIBIA
PATELLA
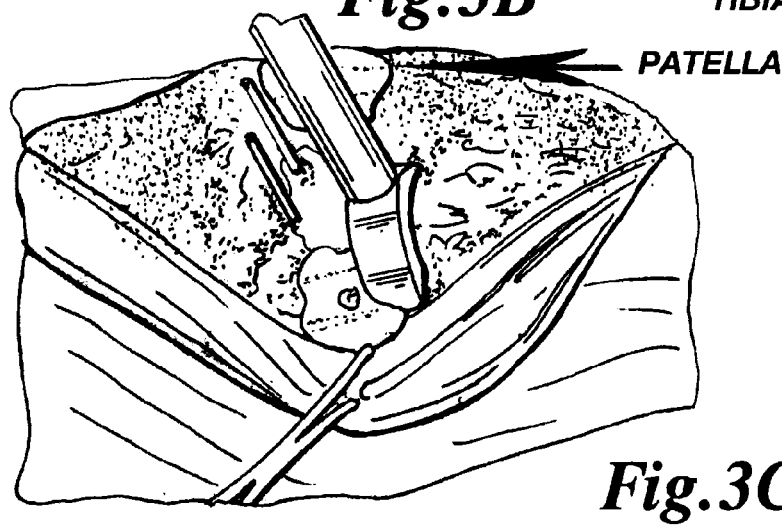
*Fig. 3C*

Fig. 6   SOFT TISSUE OR PATELLOFEMORAL ACCOMODATING CONTOUR

DRILL GUIDE TINES

DRILL

ALTERNATE ADDITIONAL PIVOT LOCATIONS

PIVOT APERTURES COULD BE A PLURALITY OF THEM (IN ONE GUIDE OR MULTIPLE GUIDES) TO FACILITATE MINIMAL INCISION SIZE

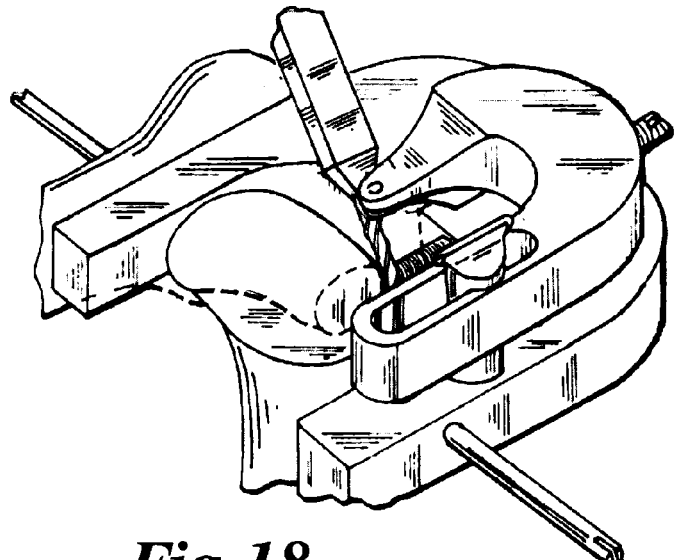
*Fig.18*
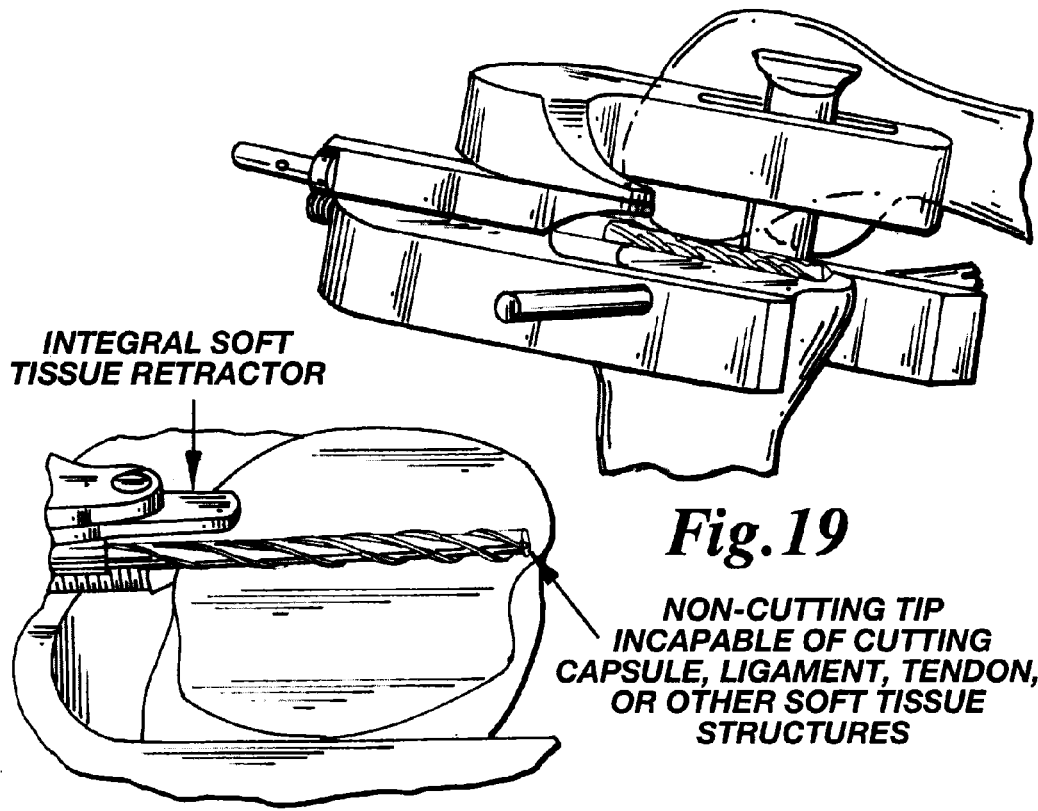
INTEGRAL SOFT TISSUE RETRACTOR
*Fig.19*
NON-CUTTING TIP INCAPABLE OF CUTTING CAPSULE, LIGAMENT, TENDON, OR OTHER SOFT TISSUE STRUCTURES
*Fig.20*

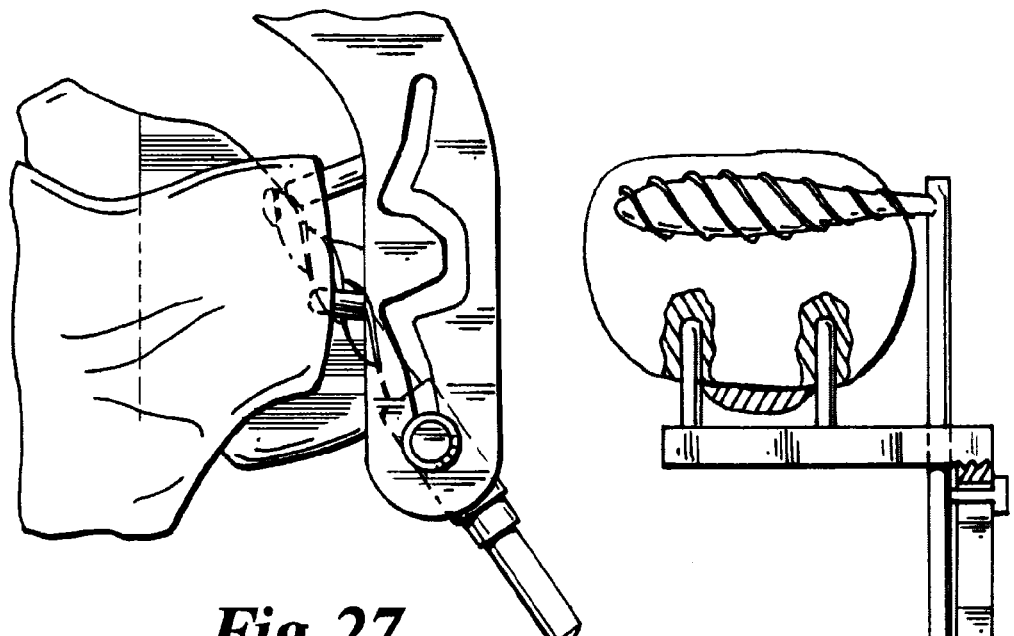
*Fig.27*
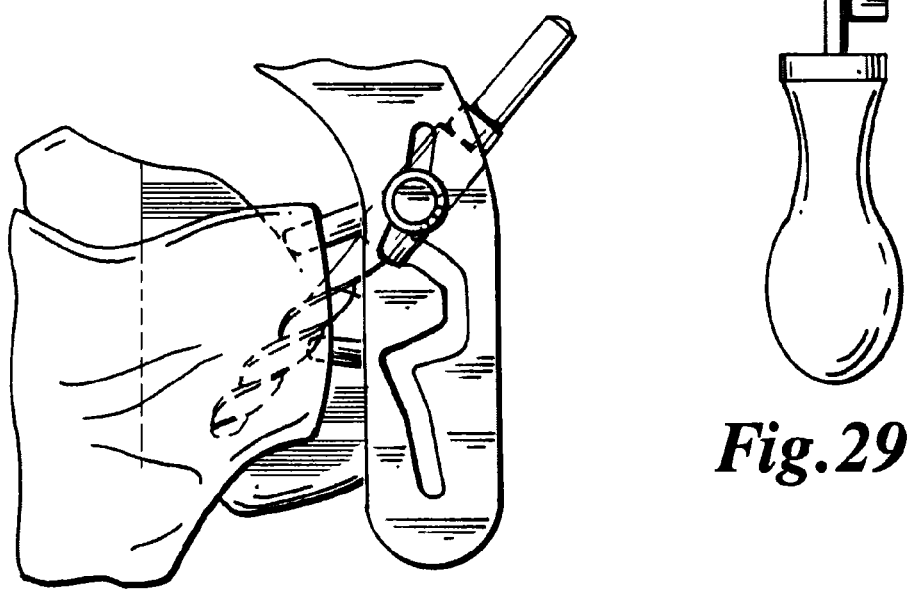
*Fig.28*
*Fig.29*

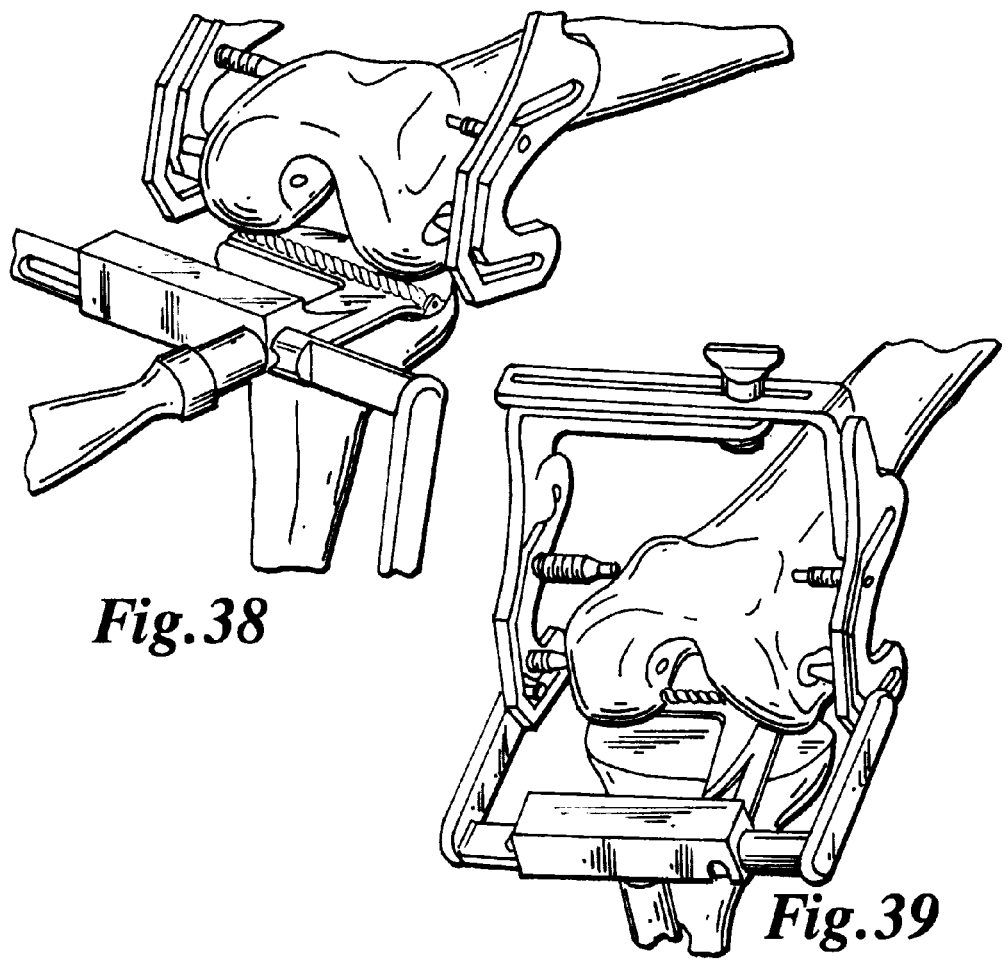
Fig.38
Fig.39
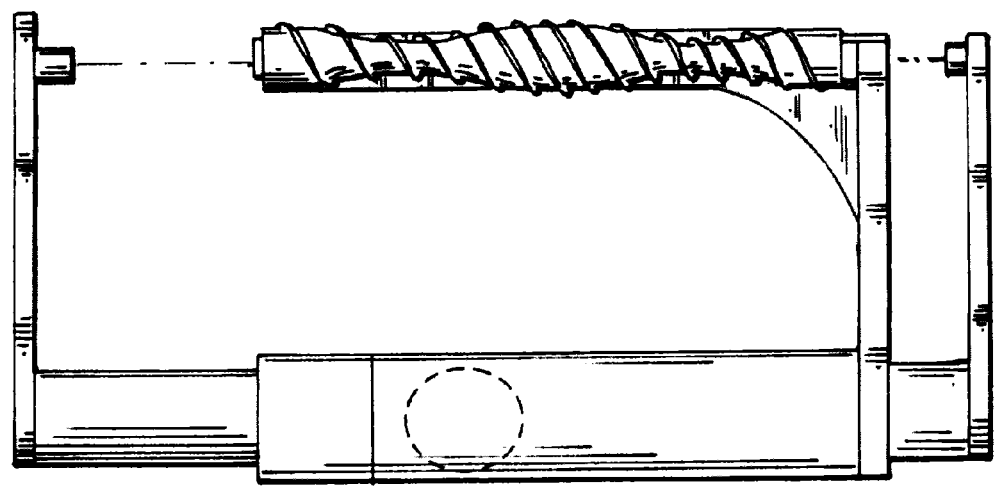
Fig.40

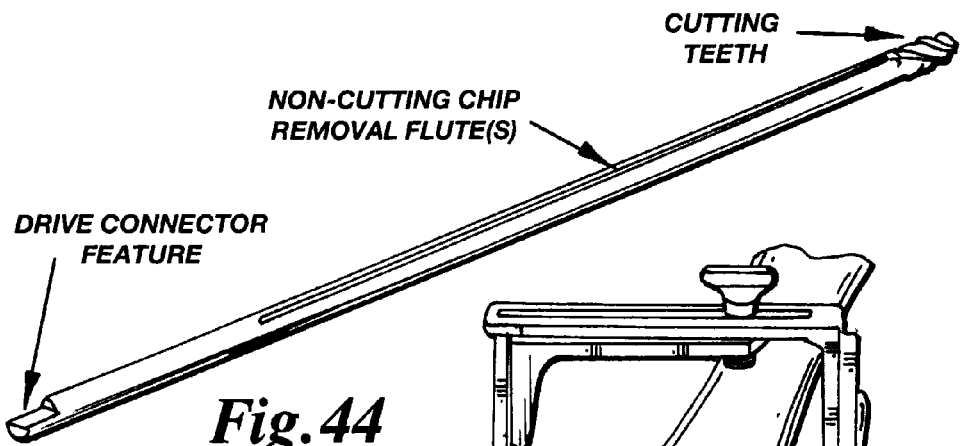
Fig.44
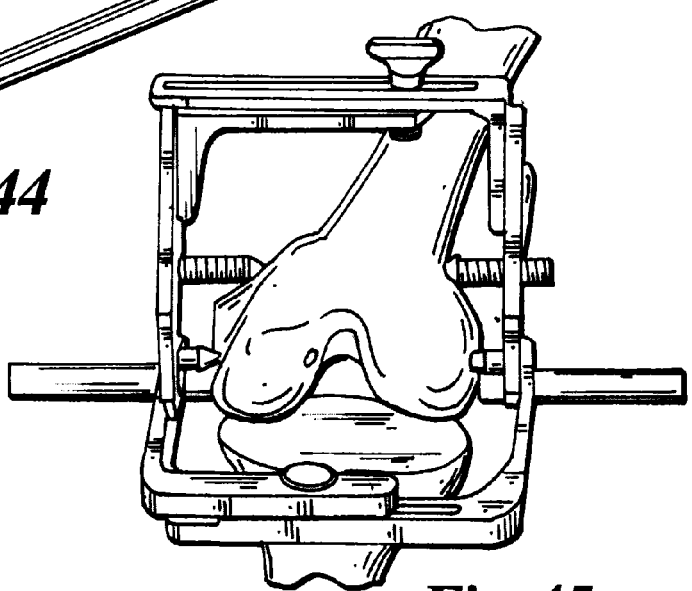
Fig.45
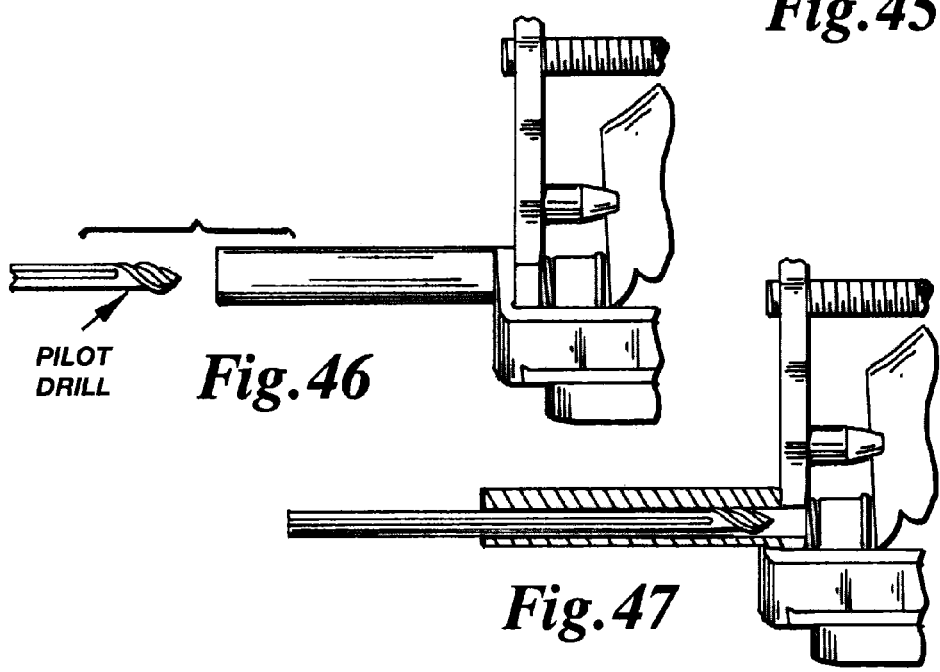
Fig.46
Fig.47

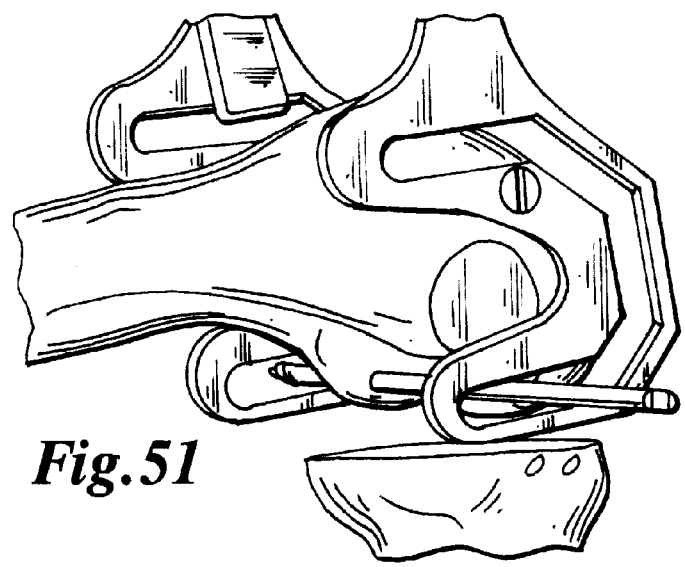
*Fig.51*
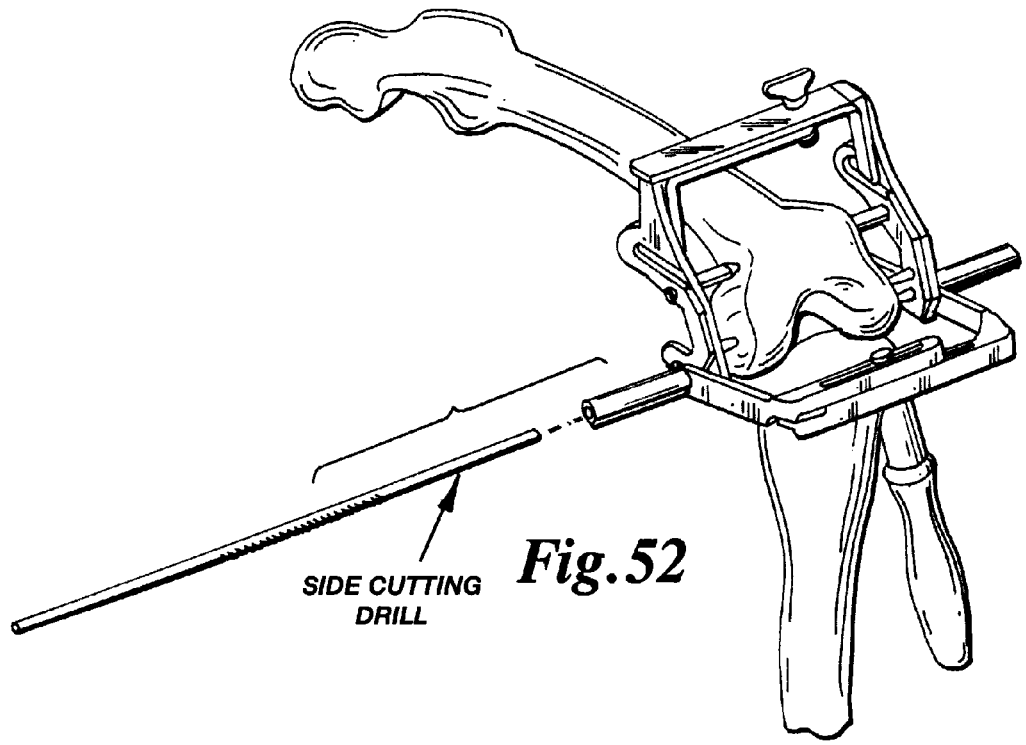
SIDE CUTTING DRILL  *Fig.52*

BONE REMNANTS TO BE REMOVED

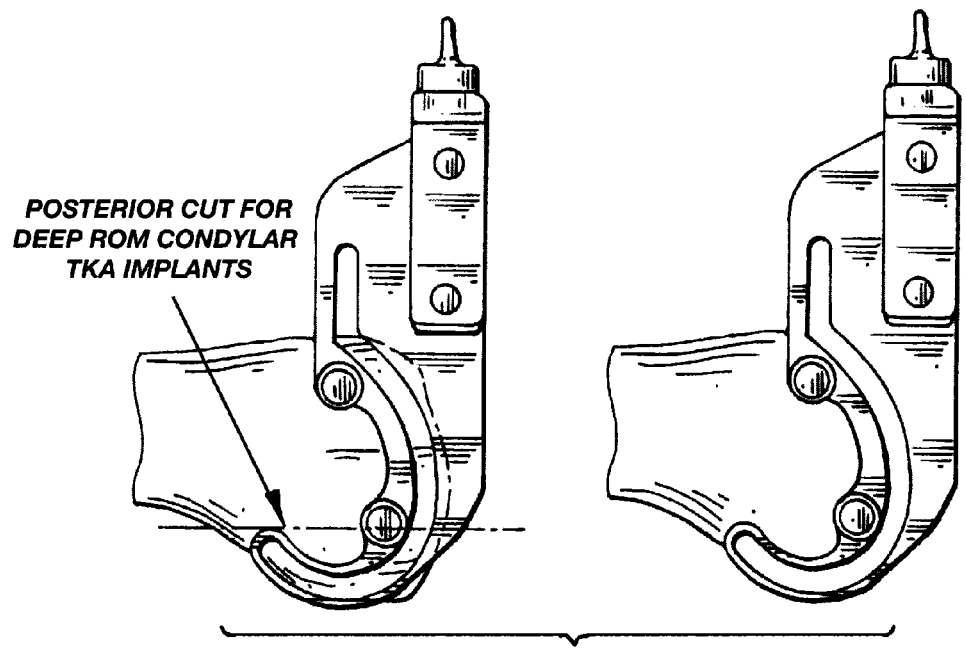
Fig.61
POSTERIOR CUT FOR DEEP ROM CONDYLAR TKA IMPLANTS
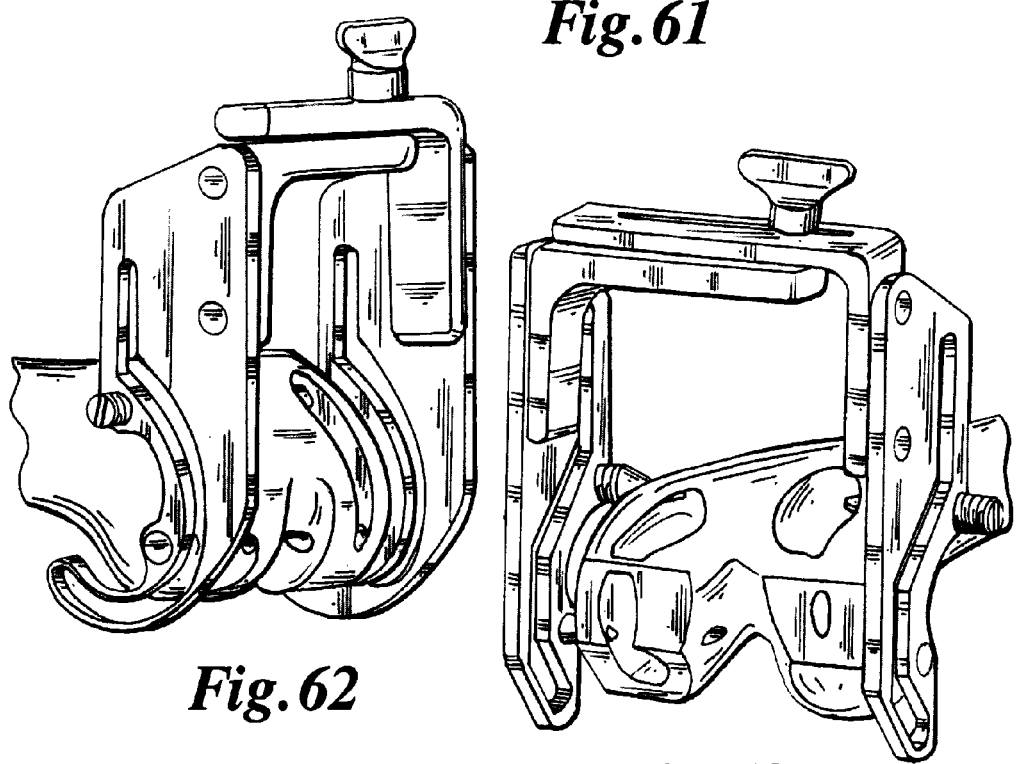
Fig.62
Fig.63

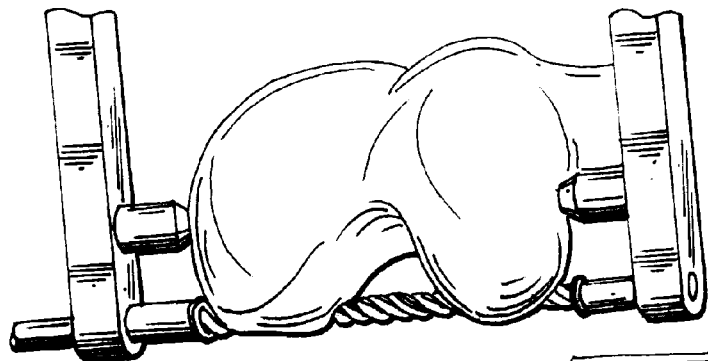

Fig. 78

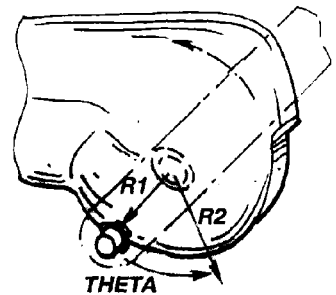

Fig. 79

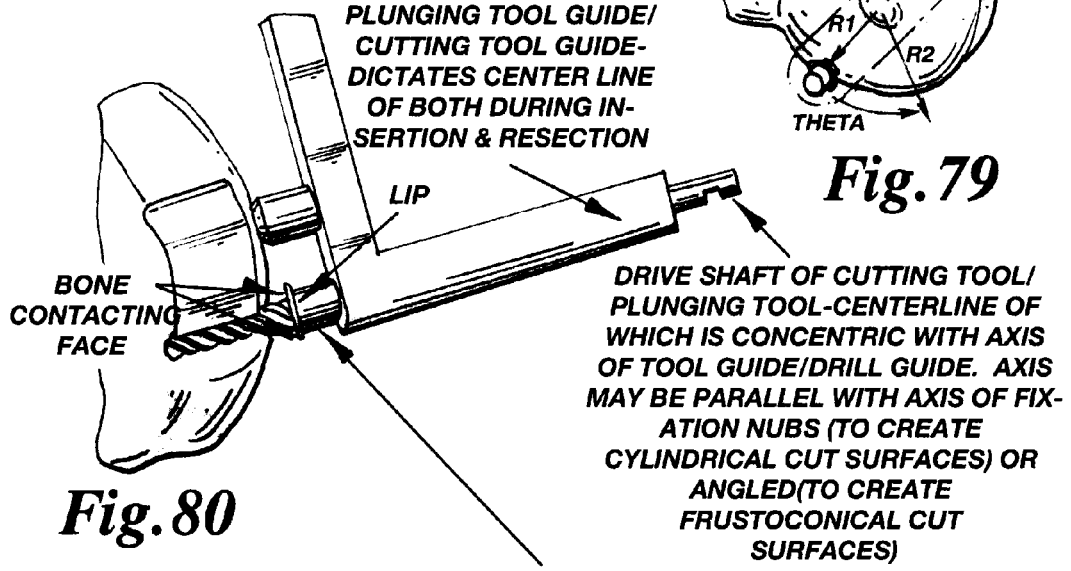

Fig. 80

PLUNGING TOOL GUIDE/ CUTTING TOOL GUIDE- DICTATES CENTER LINE OF BOTH DURING IN- SERTION & RESECTION

LIP

BONE CONTACTING FACE

DRIVE SHAFT OF CUTTING TOOL/ PLUNGING TOOL-CENTERLINE OF WHICH IS CONCENTRIC WITH AXIS OF TOOL GUIDE/DRILL GUIDE. AXIS MAY BE PARALLEL WITH AXIS OF FIX- ATION NUBS (TO CREATE CYLINDRICAL CUT SURFACES) OR ANGLED(TO CREATE FRUSTOCONICAL CUT SURFACES)

SOFT TISSUE 'SLEEVE'-PERHAPS SPRING LOADING TO BIAS IT INTO CONTACT WITH BONE TO PREVENT SOFT TISSUE CONTACT WITH CUTTING SURFACES OF CUTTING TOOL. SLEEVE COULD/SHOULD BE ARTICULATED WITH MILLING HANDLE TO REMAIN IN CONTACT WITH BONE AS MILL OR OTHER CUTTER TRAVERSES ITS OR THE CUTTING PATH. THE LITTLE LIP, PERHAPS A BIGGER LIP, COULD HELP RETAIN THE BONE CONTACTING FACE BETWEEN BONE & CAPSULE/LIGAMENT/SOFT TISSUE DURING CUTTING. IN THIS MANNER, CONTACT BETWEEN THE CUTTING TOOL AND SOFT TISSUE, AND THEREBY ANY TRAUMA BEYOND INSERTION OF THE TOOL THROUGH THE SOFT TISSUE AND ACROSS THE BONE, MAY BE AVOIDED.

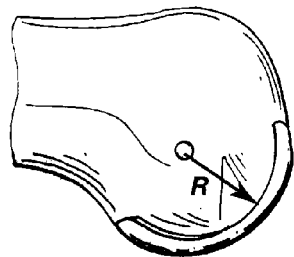
*Fig. 81*
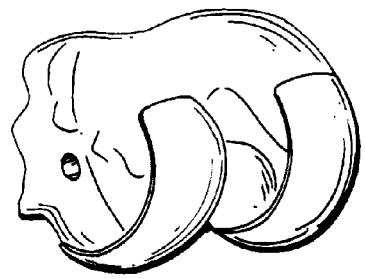
*Fig. 82*
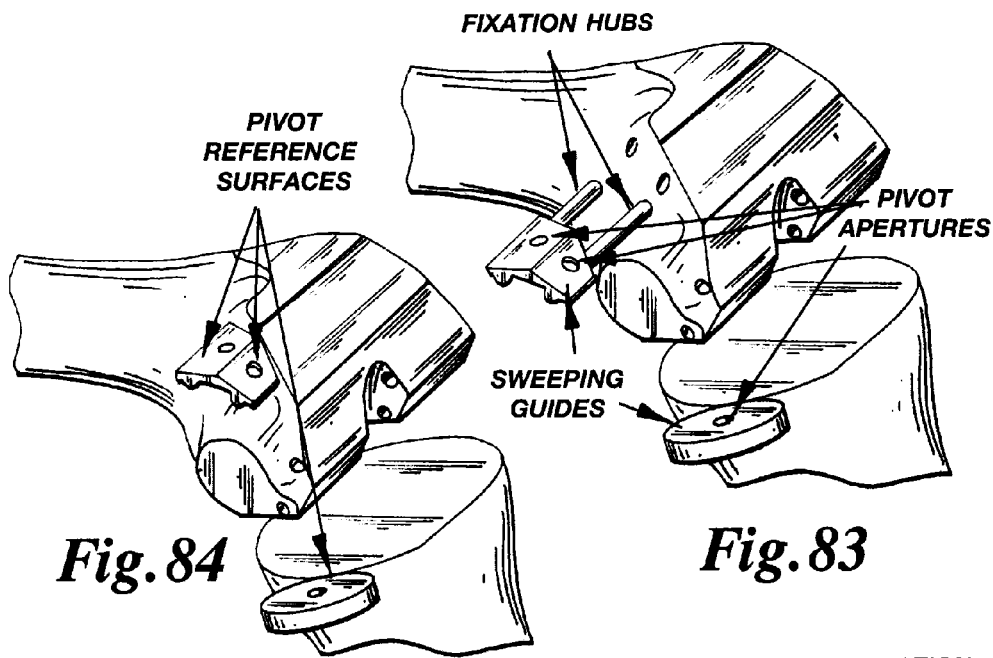
*Fig. 84*  *Fig. 83*
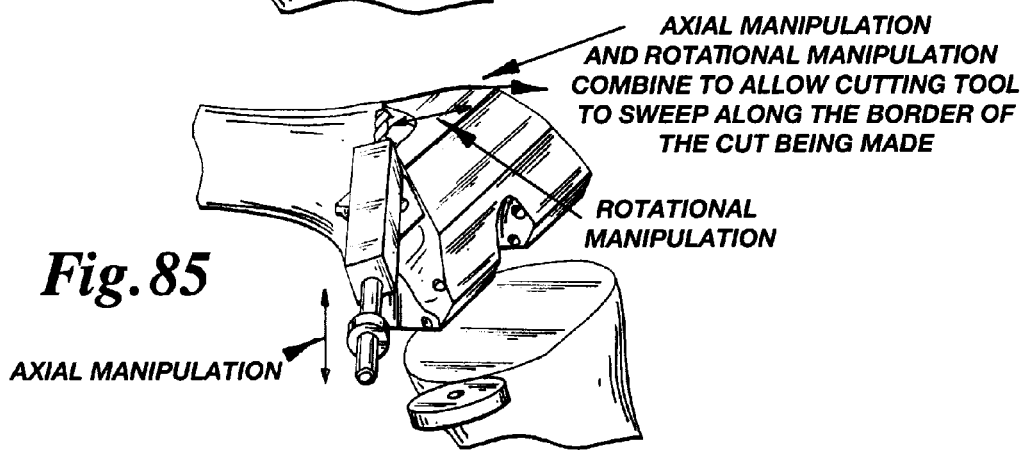
*Fig. 85*

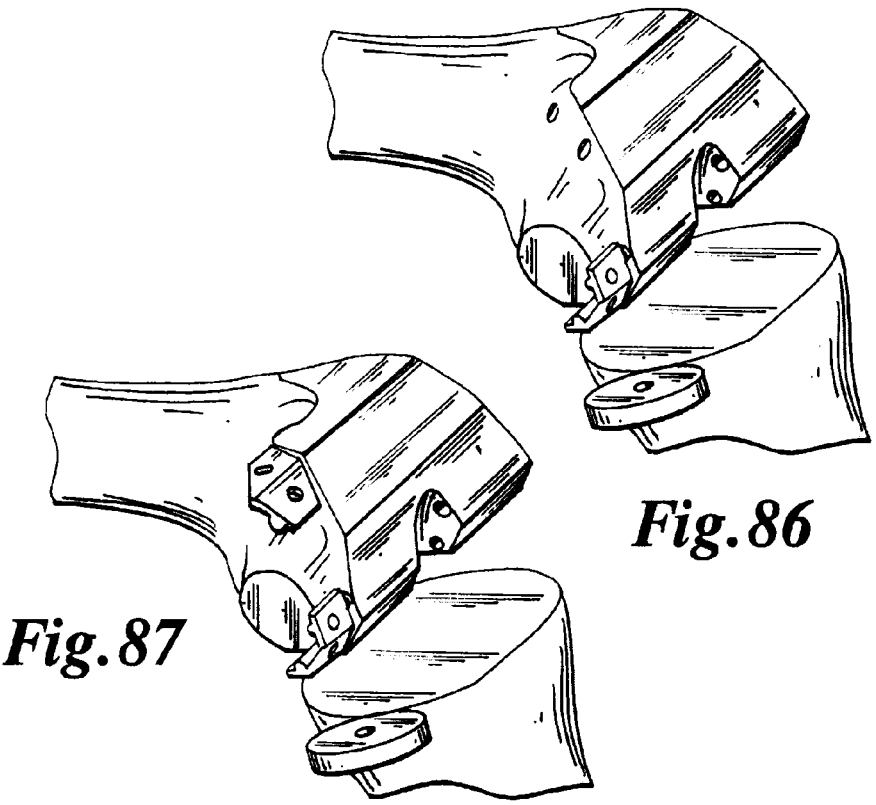
*Fig. 86*
*Fig. 87*
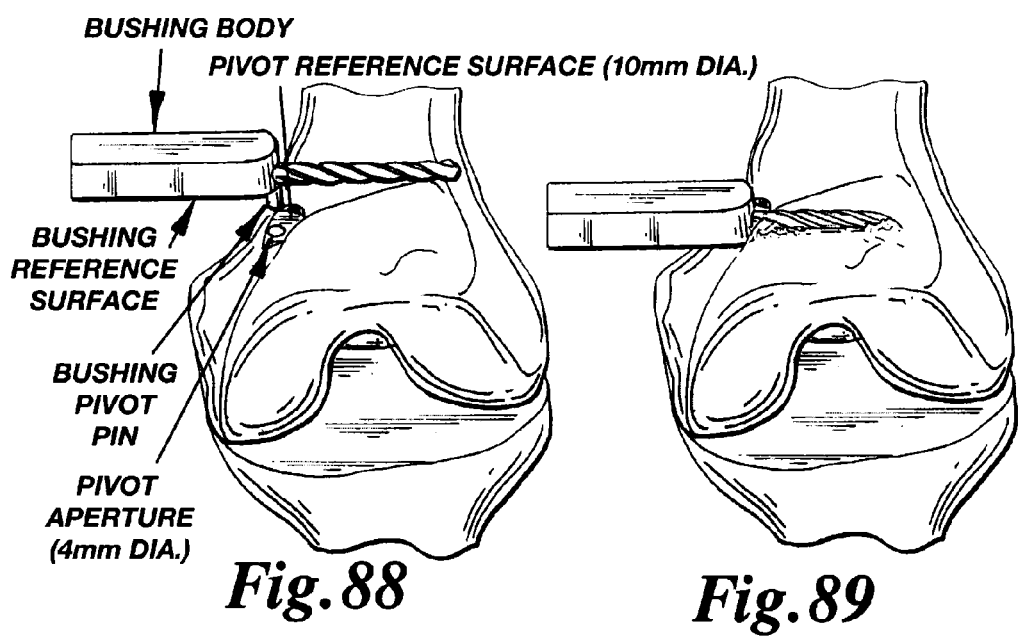
*Fig. 88*  *Fig. 89*

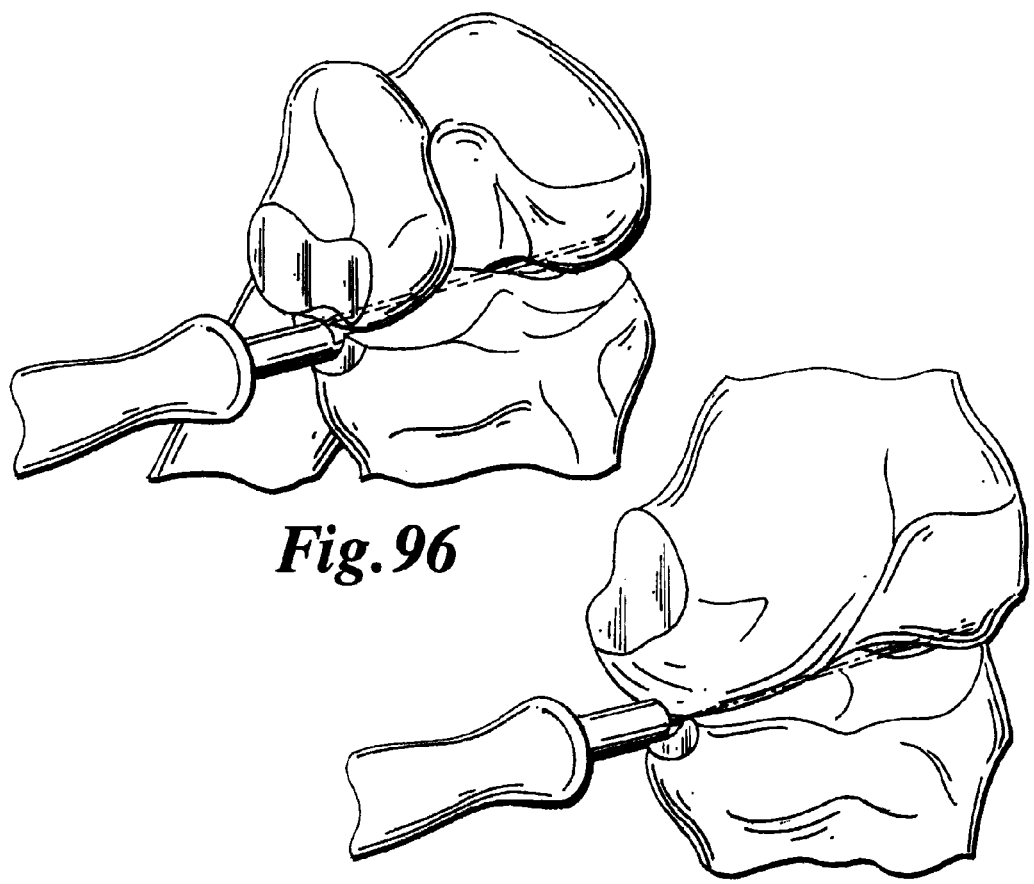
*Fig. 96*
*Fig. 97*
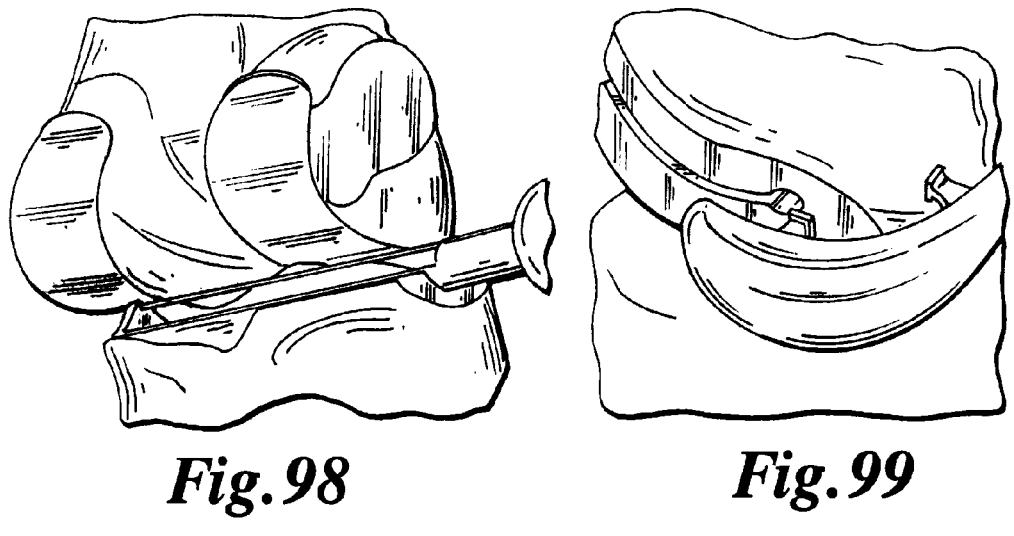
*Fig. 98*  *Fig. 99*

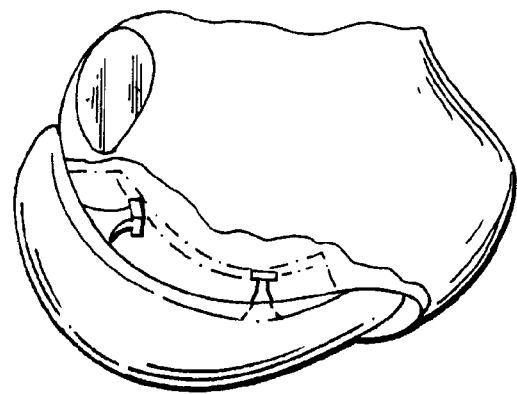
*Fig.100*
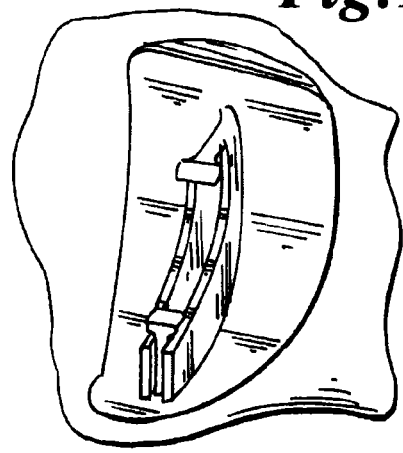 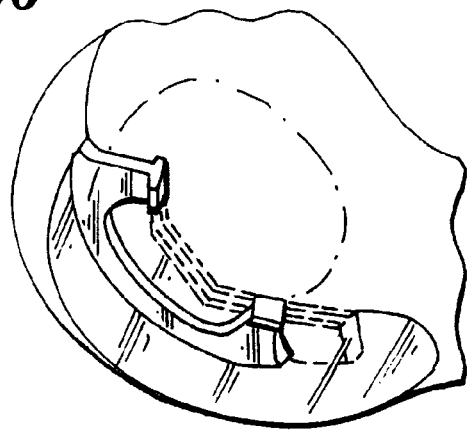
*Fig.101*  *Fig.102*
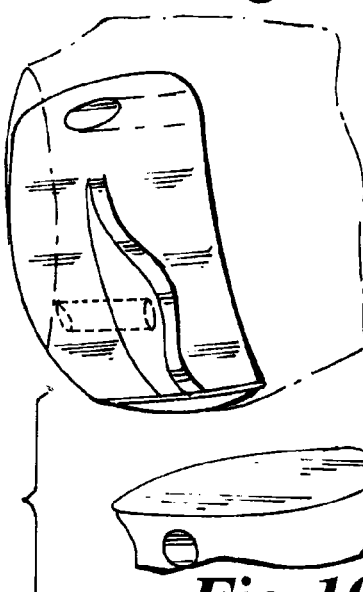 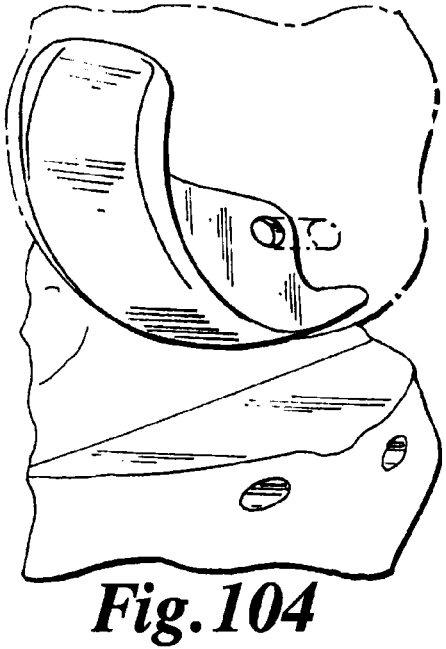
*Fig.103*  *Fig.104*

CROSS PIN

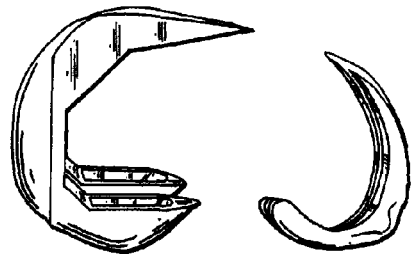
Fig.117
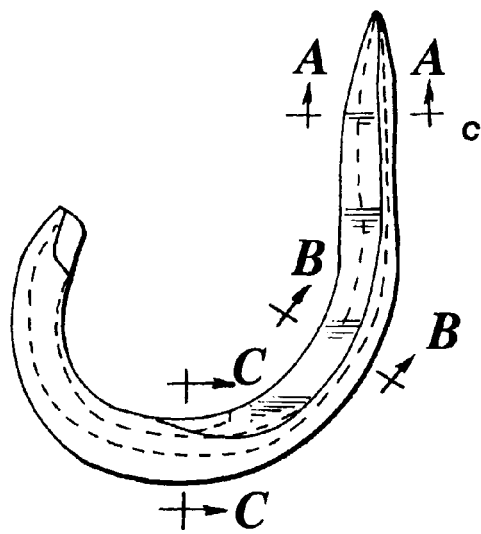
Fig.118
CONDYLAR IMPLANT RESECTION SURFACE
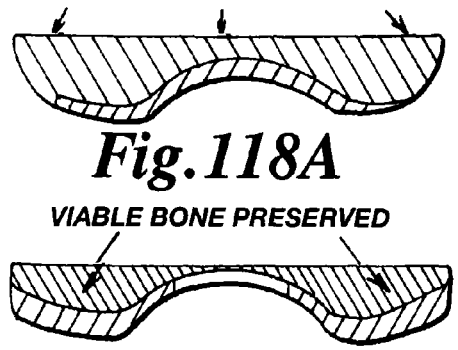
Fig.118A
VIABLE BONE PRESERVED
Fig.118B
Fig.118C
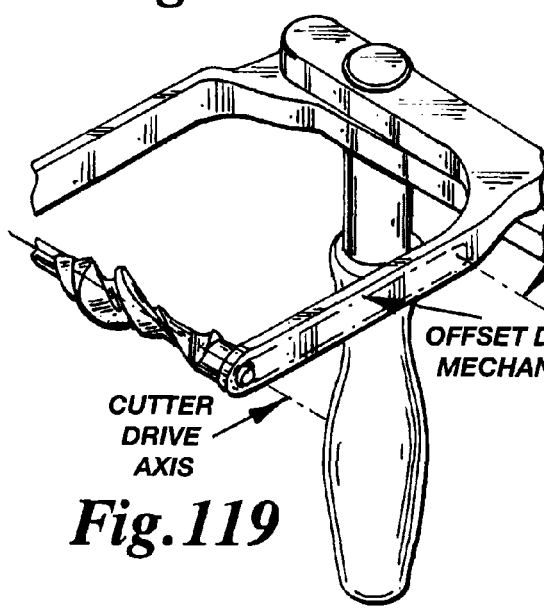
DRIVE INPUT AXIS
OFFSET DRIVE MECHANISM
CUTTER DRIVE AXIS
Fig.119
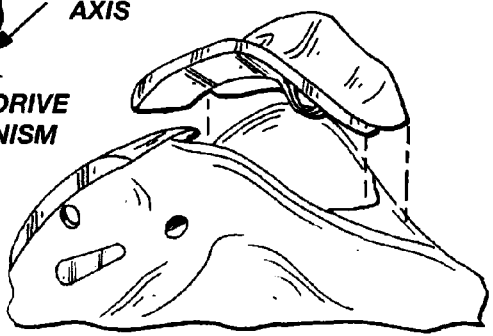
Fig.120

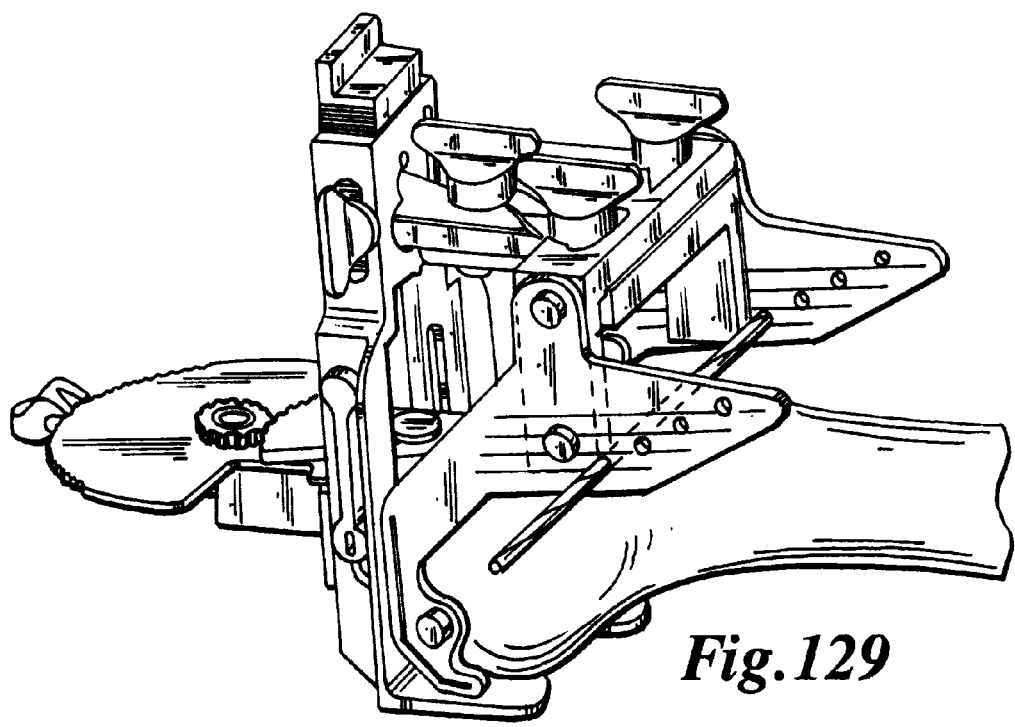
*Fig.129*
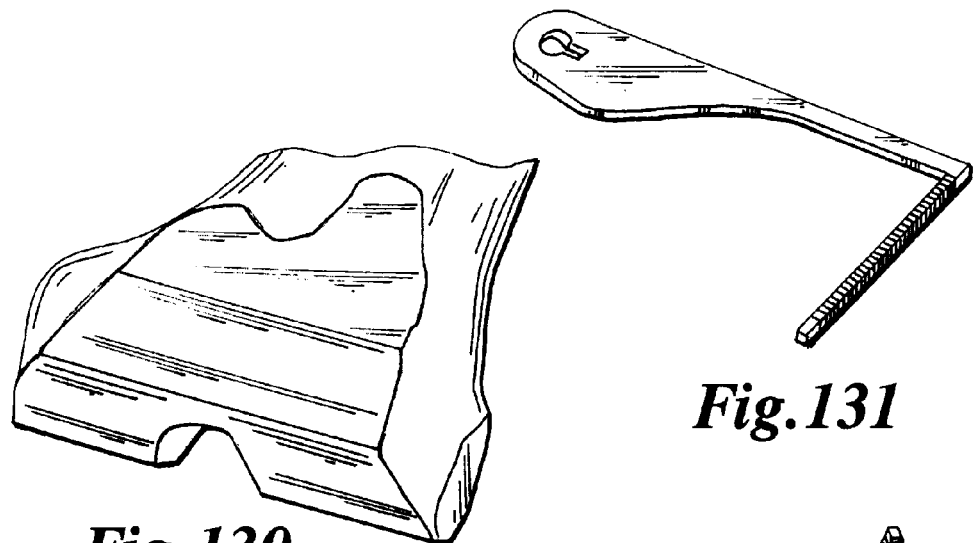
*Fig.130*
*Fig.131*
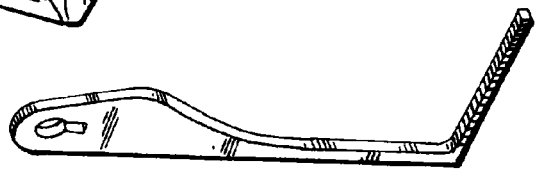
*Fig.132*

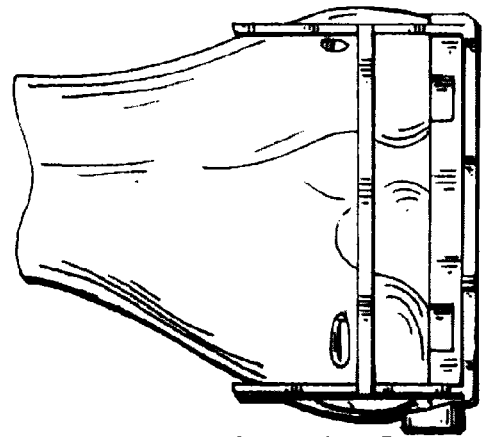
*Fig.152*
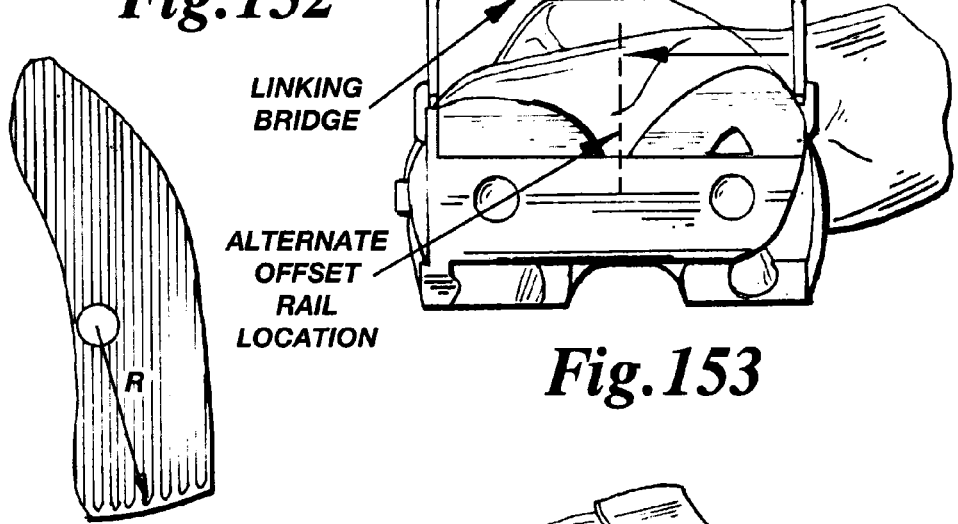
LINKING BRIDGE
ALTERNATE OFFSET RAIL LOCATION
*Fig.153*
*Fig.154*
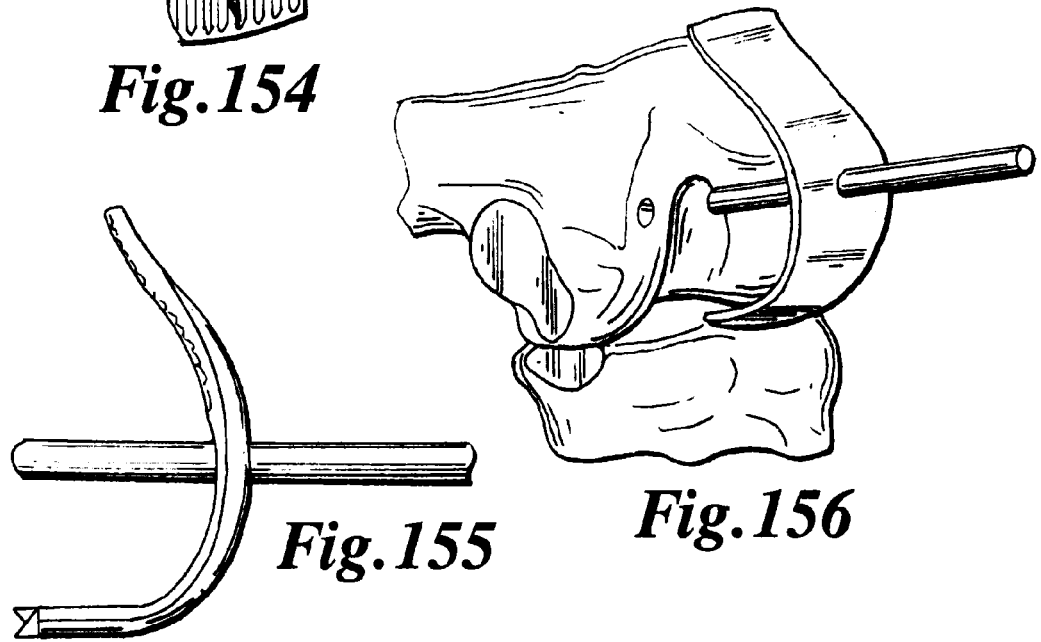
*Fig.155*
*Fig.156*

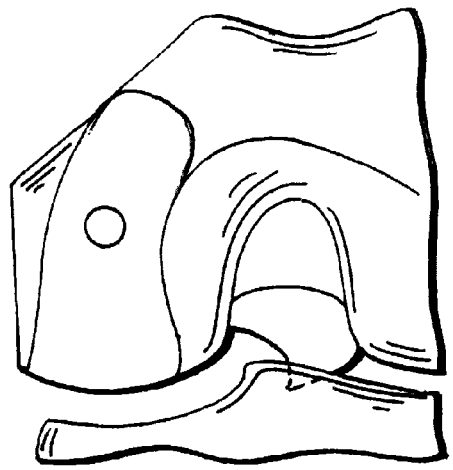
Fig.161
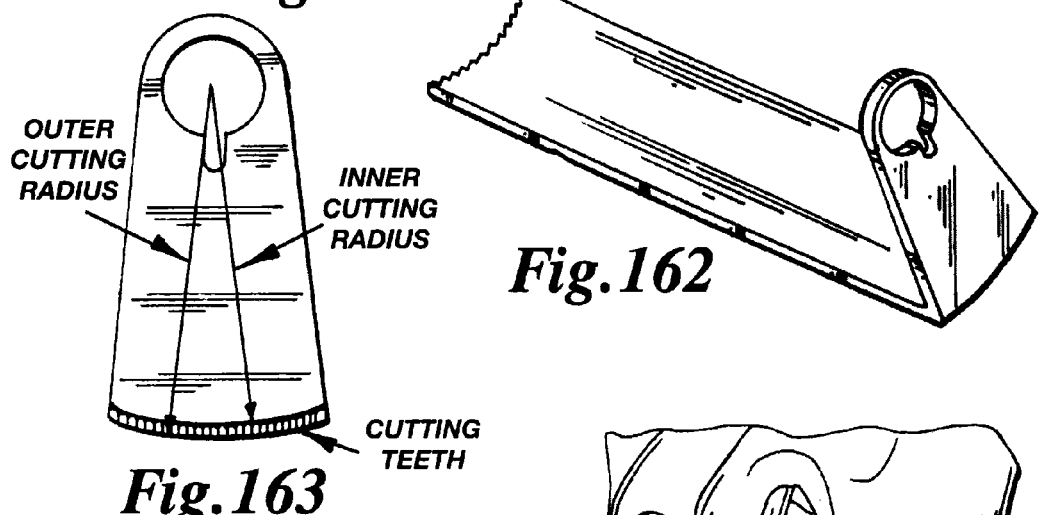
Fig.162
Fig.163
OUTER CUTTING RADIUS
INNER CUTTING RADIUS
CUTTING TEETH
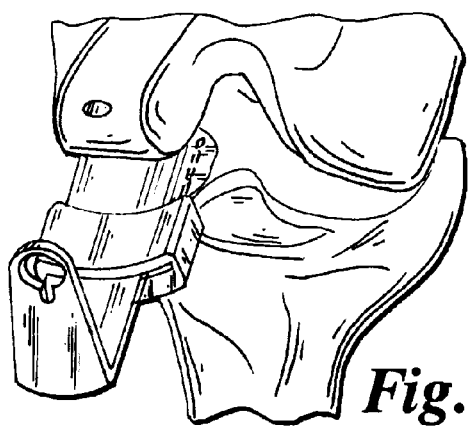
Fig.164
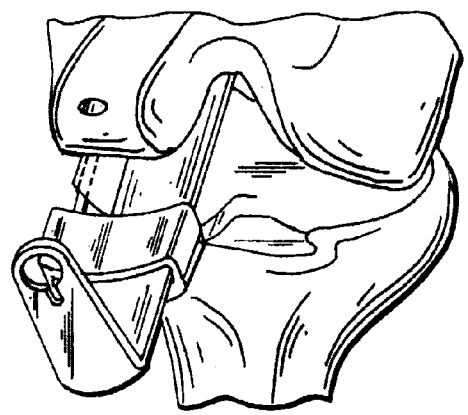
Fig.165

METHODS AND APPARATUS FOR IMPROVED PROFILE BASED RESECTION

CLAIM TO PRIORITY

The present invention is a divisional of U.S. application Ser. No. 11/075,553, filed Mar. 8, 2005, now abandoned, METHODS AND APPARATUS FOR IMPROVED PROFILE BASED RESECTION, which claims priority to U.S. Provisional Application No. 60/551,160, filed Mar. 8, 2004, entitled, "METHODS AND APPARATUS FOR IMPROVED PROFILE BASED RESECTION," and U.S. Provisional Application No. 60/551,080, filed Mar. 8, 2004, entitled, "METHODS AND APPARATUS FOR PIVOTABLE GUIDE SURFACES FOR ARTHROPLASTY," and U.S. Provisional Application No. 60/551,078, filed Mar. 8, 2004, entitled, "METHODS AND APPARATUS FOR MINIMALLY INVASIVE RESECTION," and U.S. Provisional Application No. 60/551,096, filed Mar. 8, 2004, entitled, "METHODS AND APPARATUS FOR ENHANCED RETENTION OF PROSTHETIC IMPLANTS," and U.S. Provisional Application No. 60/551,631, filed Mar. 8, 2004, entitled, "METHODS AND APPARATUS FOR CONFORMABLE PROSTHETIC IMPLANTS," and U.S. Provisional Application No. 60/551,307, filed Mar. 8, 2004, entitled, "METHODS AND APPARATUS FOR IMPROVED CUTTING TOOLS FOR RESECTION," and U.S. Provisional Application No. 60/551,262, filed Mar. 8, 2004, entitled, "METHODS AND APPARATUS FOR IMPROVED DRILLING AND MILLING TOOLS FOR RESECTION," which is a divisional of U.S. patent application Ser. No. 11/036,584, filed Jan. 14, 2005 now U.S. Pat. No. 7,815,645, entitled, "METHODS AND APPARATUS FOR PINPLASTY BONE RESECTION," which is a divisional of U.S. patent application Ser. No. 11/049,634, filed Feb. 3, 2005 now abandoned, entitled, "METHODS AND APPARATUS FOR WIREPLASTY BONE RESECTION," which claims priority to U.S. Provisional Application No. 60/536,320, filed Jan. 14, 2004, and U.S. patent application Ser. No. 11/049,634, filed Feb. 3, 2005 now abandoned, entitled, "METHODS AND APPARATUS FOR WIREPLASTY BONE RESECTION," which claims priority to U.S. Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for bone resection to allow for the interconnection or attachment of various prosthetic devices with respect to the patient. More particularly, the present invention relates to methods and apparatus for improved profile based resection techniques for arthroplasty.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in total knee replacement and other forms of bone resection for over 30 years. Unfortunately, present approaches to using existing planar or non-planar saw blade instrumentation systems all possess certain limitations and liabilities.

Perhaps the most critical factor in the clinical success of any bone resection for the purpose of creating an implant surface on the bone is the accuracy of the implant's placement. This can be described by the degrees of freedom associated with each implant. In the case of a total knee arthroplasty (TKA), for example, for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems for TKA, the distal resection cutting guide is positioned by drilling two long drill bits into the anterior cortex across the longitudinal axis of the bone. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking" inherent in the use of multiple alignment guides and cutting guides.

Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA and other bone resection procedures for more than 30 years, there are still reports of incidences where poor cuts result in significant gaps in the fit between the implant and the bone. Improvements in the alignment and operation of cutting tools for resecting bone surfaces are desired in order to increase the consistency and repeatability of bone resection procedures as is the improvement of prosthetic stability in attachment to bone.

One technique that has been developed to address these challenges has been the profile based resection (PBR) techniques taught, for example, by U.S. Pat. Nos. 5,514,139, 5,597,397, 5,643,272, and 5,810,827. In a preferred embodiment of the PBR technique, a side cutting tool such as a milling bit or side drill bit is used to create the desired resected surface. While the PBR technique offers many advantages over conventional resection and arthroplasty techniques, it would be desirable to provide enhancements to the PBR technique that improve the ability to address soft tissue management and minimally invasive surgical techniques.

SUMMARY OF THE INVENTION

The present invention provides for embodiments of alignment guides, cutting guides, cutting tools and soft tissue management techniques for profile based resection (PBR) arthroplasty facilitating intraoperative and postoperative efficacy and ease of use. In one embodiment, a manual alignment guide is provided that permits less invasive incisions by providing soft tissue accommodating contours or reliefs. In another embodiment, a single medial drill guide plate is used for the PBR arthroplasty.

The present invention utilizes a number of embodiments of cutting tools to remove boney material to create cut surfaces for prosthetic implant attachment and fixation. The overriding objects of the embodiments are to provide the ability to perform resection in very small incisions, the creation of precise and accurate cut(s), and to provide for soft tissue protection characteristics and features preventing the tool from accidentally harming soft tissue. Specifically, many of the cutting tool embodiments disclosed are either incapable or highly resistant to damaging soft tissue, or are by means disclosed prevented from coming into contact with soft tissue in the first place.

The present invention utilizes a number of embodiments of cutting guide technologies loosely or directly based on Profile Based Resection (PBR). The overriding objects of PBR technologies are to provide for significantly improved reproducibility of implant fit and alignment in a manner largely independent of the individual surgeon's manual skills, while providing for outstanding ease of use, economic, safety, and work flow performance.

The present invention utilizes a number of embodiments of alignment or drill guides to precisely and accurately determine the desired cutting guide location/orientation, thus cut surface location(s)/orientation(s), thus prosthetic implant location and orientation. The overriding objects of the embodiments are to precisely and accurately dictate the aforementioned locations and orientations while optionally enabling ease of use in conjunction with manually or Computer Assisted techniques, and while optionally enabling ease of use in minimally invasive procedures where surgical exposure and trauma are minimized.

The present invention utilizes a number of methods and apparatus embodiments of soft tissue management techniques and the devices supporting said techniques. The overriding object of these embodiments is to take advantage of the anatomy, physiology, and kinematics of the human body in facilitating clinical efficacy of orthopedic procedures.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that decreases risk to soft tissue, incision or exposure size requirements, manual skill requirements, and/or visualization of cutting action.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which:

FIGS. 1, 2, and 3 are pictorial representations standard incision sizes or exposure required by the prior art, while

DETAILED DESCRIPTION OF THE PREFERRED EMBODIMENTS

It should be noted that, in many of the figures, the cut surface created by the cutting tool in accordance with the techniques of the present invention are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity FIGS. 1 through 4

Figure 1:
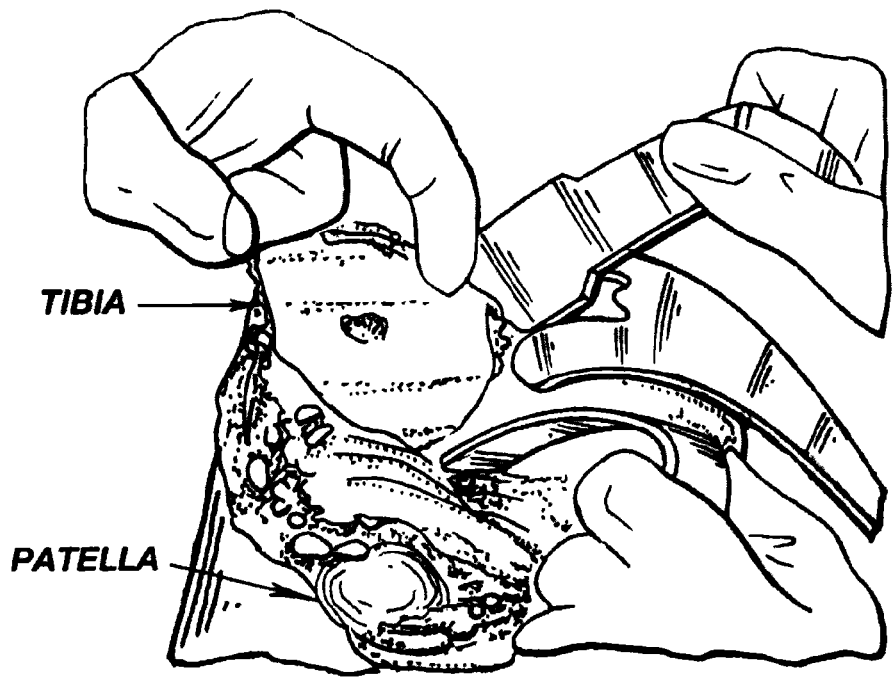
Figure 2:
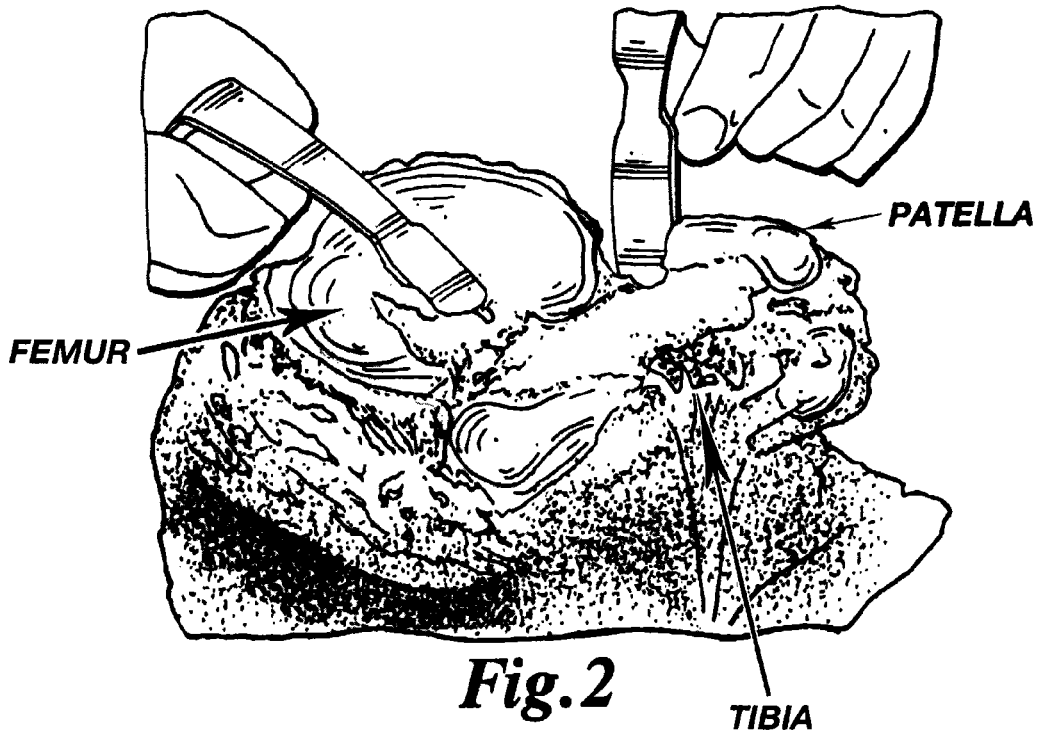
Figure 4:
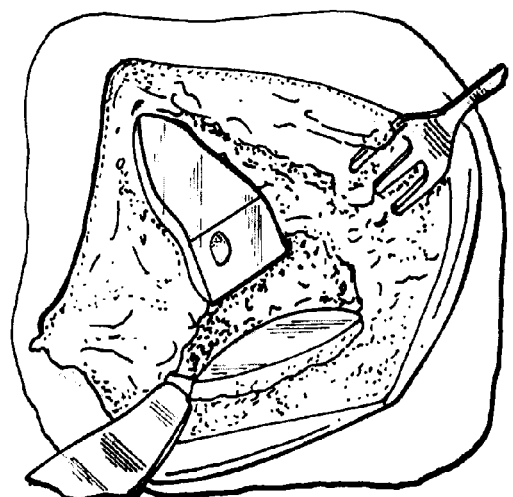
FIG. 4 is a pictorial representation or approximation of one form of surgical exposure that is desired.

FIGS. 1 and 2 show conventional surgical exposures and instrumentation being utilized. FIG. 4 shows a reduced incision currently utilized in performing the current state of the art in 'minimally invasive' Unicondylar Knee Replacement.

FIGS. 5 through 11

Figure 5:
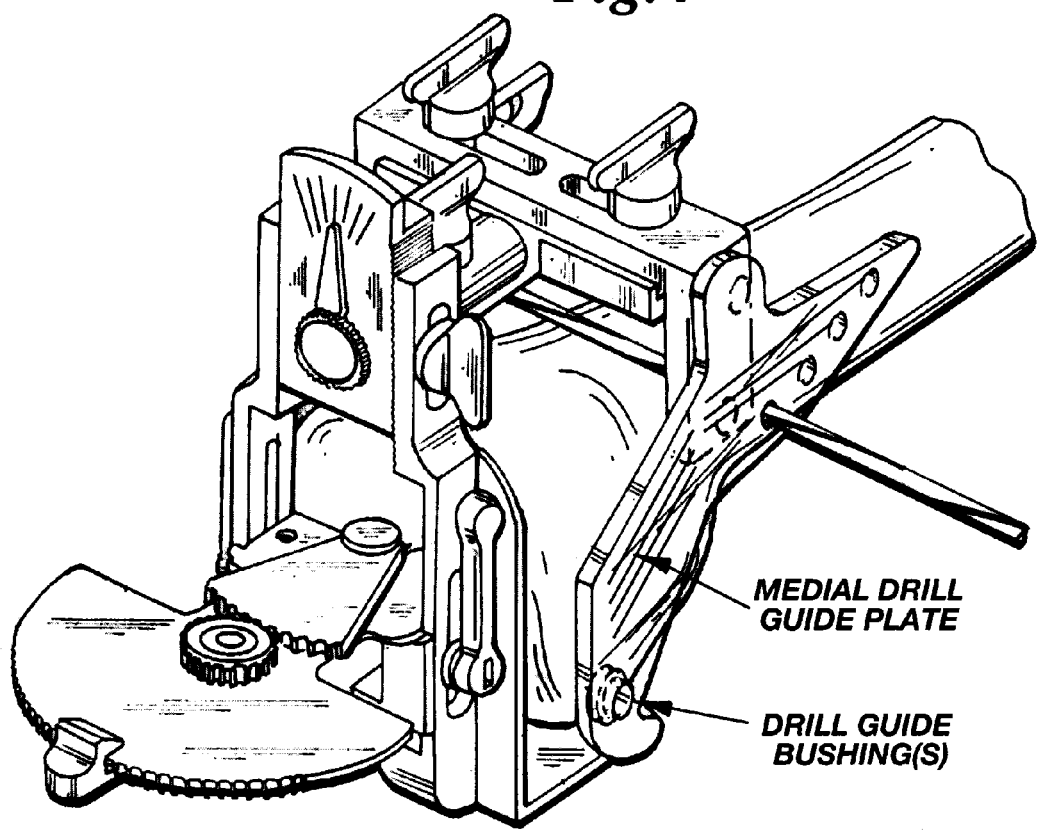
FIGS. 5-168 show various depictions of embodiments and methods in accordance with alternate embodiments of the present invention.
Figure 7:
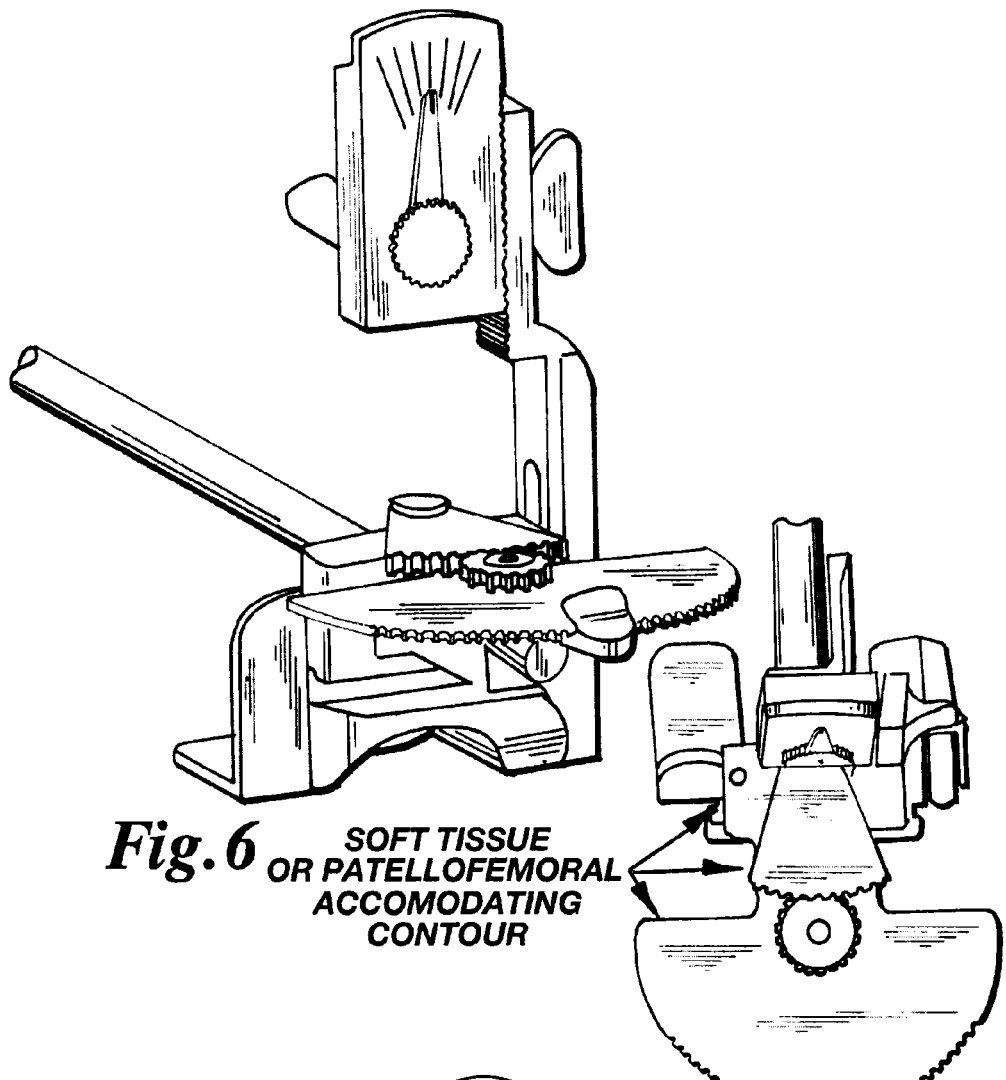

FIGS. 5 through 11 concentrate on alignment guide and/or drill guide techniques. FIG. 5 shows a manually operated alignment guide suitable for use with surgical exposures similar to that shown in FIG. 2 (it should be noted that surgical navigation sensors could be used to assist in determining final drill guide location and orientation). FIGS. 6 and 7 show an improvement upon the embodiment shown in FIG. 5 for enabling manual alignment guide use in less invasive incisions by providing soft tissue accommodating contours or reliefs. In other words, for a medial parapatellar incision, the alignment guide is configured to allow for appropriate contact and referencing of the distal and posterior femoral condyles, the IM canal (when not relying on an extramedullary reference or inference of the mechanical axis) or IM Rod, the anterior cortex or anterior runout point of a given or proposed implant size (via a stylus not shown), and the epicondylar axis via palpitation or visual reference while the patellar tendon, patella, and/or quadriceps tendon is draped over the lateral side (right side as shown in the figures) of the alignment guide allowing insertion of the guide when the patella is neither everted not fully dislocated as in conventional techniques.

It should be noted that initial alignment indicated by reference of the distal femur can be further adjusted in all six degrees of freedom as a fine tuning for final cut location and orientation. This simply calls for the inclusion of additional adjustment of the location and orientation of the crossbar mechanism and/or rotational alignment arm, with respect to the initial reference provide for by contact between the body of the guide and the bone (optionally including the IM Rod), in flexion-extension angulation, varus-valgus angulation (rotational angulation and Anterior-Posterior location are already shown), mediolateral location (represented in this embodiment of the current invention by the cross bar mechanism in FIG. 5 where drill guide mediolateral location is shown as being independently and infinitely adjustable), and proximal-distal location (as shown in FIGS. 5, 6, and 7—it should be noted that this adjustment might be best embodied in an infinitely adjustable slide as opposed to the incrementally adjustable slide shown, and that simple marking would be present indicating the relative movement of the slide with respect to the body). It may be desirable to only utilize only a medial drill guide plate with multiple drill guide bushings to create holes extending partially or completely across the femur depending upon the manner in which the guides are to be connected to the femur.

Figure 8:
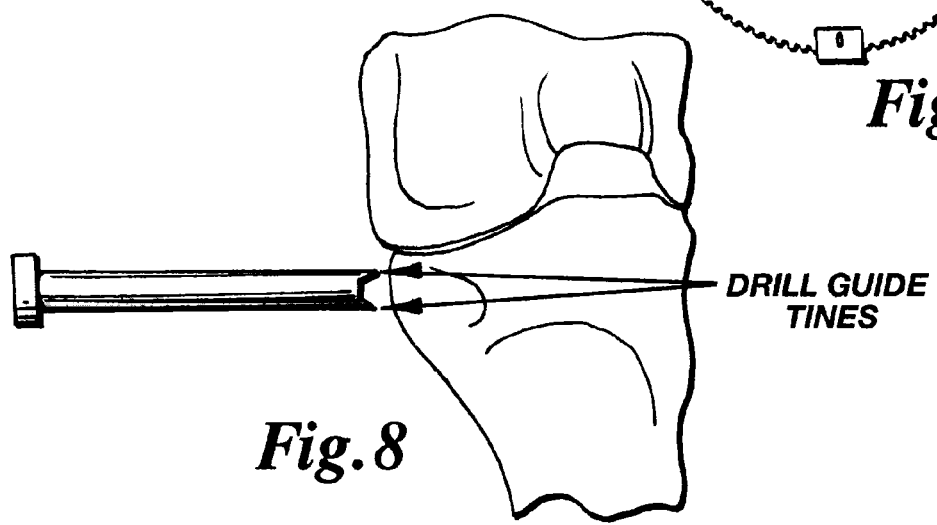
Figure 9:
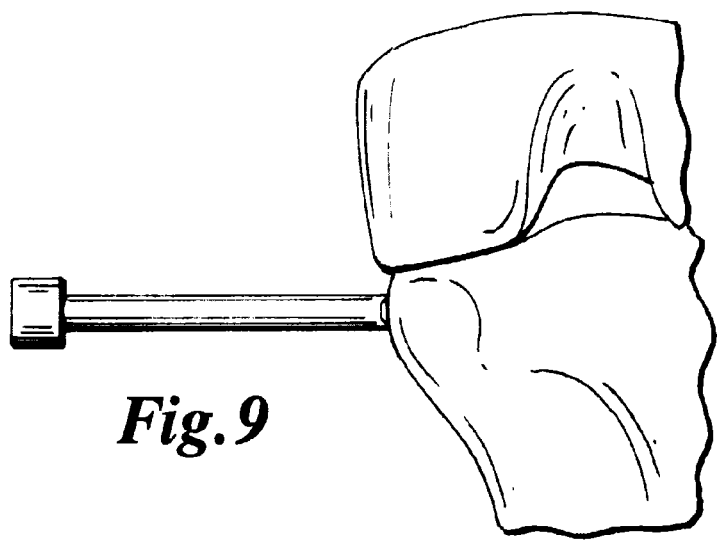
Figure 10:
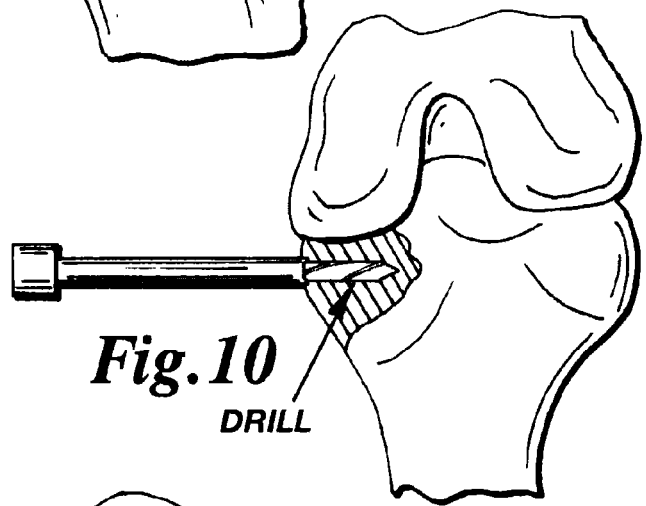
Figure 11:
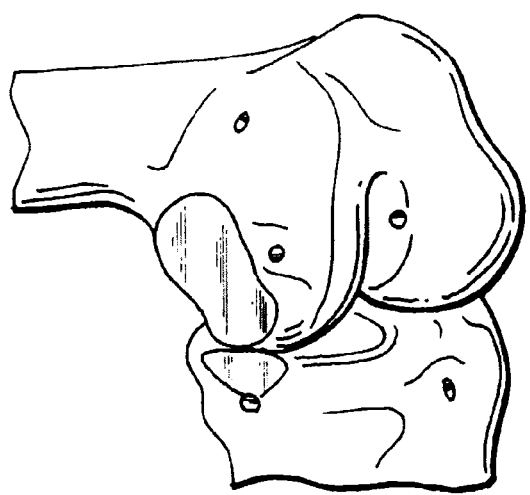
Figure 12:
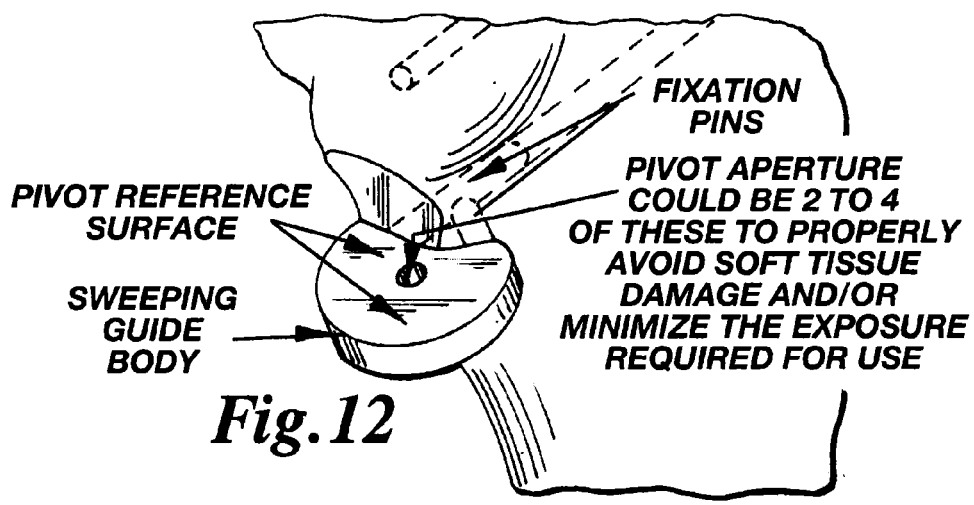
Figure 13:
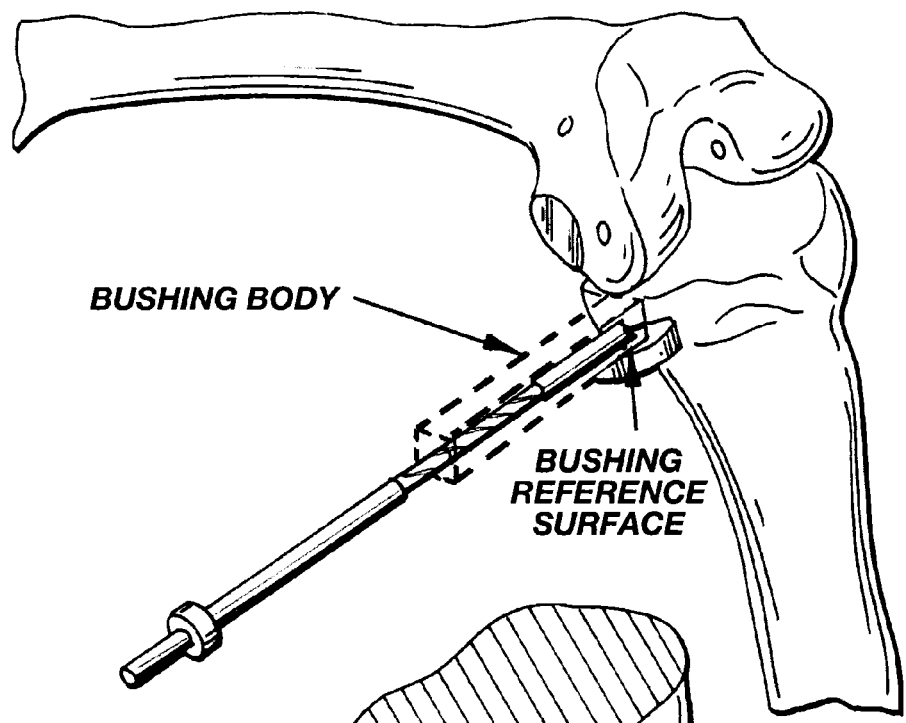
Figure 14:
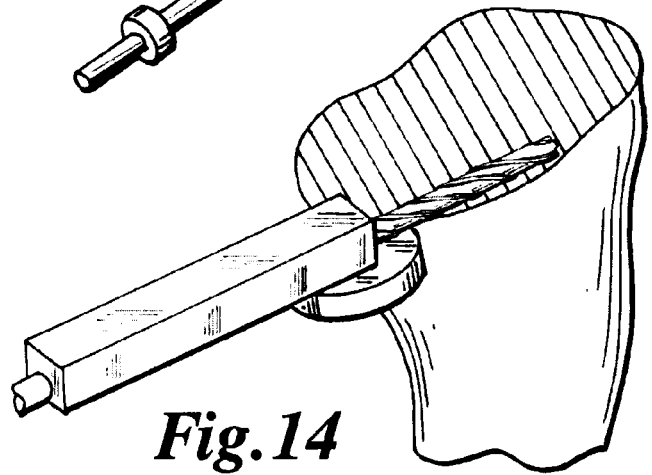

FIGS. 8, 9, and 10 show an alternative alignment/drill guide embodiment of the present invention wherein a cannulated surgically navigated handle/drill guide is used to create fixation apertures in the bone for direct or indirect fixation of a cutting guide. As shown in FIG. 8, it may be advantageous to include tines for penetrating the bone to obtain initial stabilization of the handle in the location and orientation indicated by the surgical navigation system ("Surg Nav"—this term shall be used interchangeably with Computer Aided Surgical System or Image Guided Surgical System throughout this disclosure) prior to extending the drill, represented in FIG. 10, into the bone to create the aperture. It should be noted that the aperture, or hole, thus created could be blind or extended to a specific depth, or optionally extended entirely through the bone and out the furthest side of the bone. Importantly, this process could be utilized transcutaneously through a small stab wound (perhaps 4 mm in length) through the skin to the bone surface, or through a preformed incision through which other instrumentation of the present invention or other devices may be introduced during a procedure. Further, although only one cannulation is shown, a single handle may desirably contain multiple cannulations, some or all of which could be adjustably extended into contact with the bone to reduce any wandering of the drill contacting oblique bone surfaces and improve the precision and accuracy of aperture creation (thus allowing for the creation of apertures in the medial side of the femur, represented in FIG. 11, with a single Surg Nav Handle. Also, the apertures may be configured such that the femoral and tibial apertures shown in FIG. 11 are all created using a single positioning step for the handle). As represented in FIG. 9, there is very little distance over which the drill is cantilevered between its guidance within the cannulations and its point of initial contact with the outer surface of the bone. This aspect of this embodiment of the current invention is critical in preserving the potential accuracy of Surg Nav systems, i.e.; the navigation system (the computer and the sensors) may be capable of determining appropriate location and orientation to +/−0.1 mm and +/−0.5 degrees, but if the location and/or orientation of the aperture created represents some path of least resistance in bone which is followed by the drill, the resultant location and orientation of cut surfaces, and thereby the location and orientation of the prosthesis attached thereto, will likely be seriously in error.

It should also be noted that the methods described herein are applicable to the methods demonstrated in Provisional Patent Application Ser. No. 60/536,320, entitled "Methods and Apparatus for Pinplasty Bone Resection" and Ser. No. 60/540,992, entitled "Methods and Apparatus for Wireplasty Bone Resection," the disclosures of each of which are hereby incorporated by reference.

FIGS. 12 through 34

FIGS. 12-34 disclose embodiments of the present invention for creating planar and/or curvilinear resection surfaces on or in the proximal tibial and other bones and embodiments of the present invention for prosthetic implants.

FIGS. 12-15 represents an embodiment of the present invention for cutting guides and cutting tools which substantially comprises a guide with guide pivot aperture(s) and a guide pivot reference surface(s) for mating with a bushing controlling a cutting tool, wherein the bushing possess a bushing reference plane (which mates with the pivot reference surface(s) of the guide), a bushing pivot pin, best represented in FIG. 88 (which mates with the guide pivot aperture (s) of the guide), and a cannulation for articulated and/or axial guidance of the cutting tool.

There are a number of optional features that are highly desirable depending on the preferred method of use utilized for these embodiments of the present invention. The soft tissue protection tip of the cutting tool and the integral soft tissue retractor feature of the bushing body are two principal examples represented in FIG. 20. The soft tissue protection tip can be integrally formed as a part of the cutting tool during its manufacture, be a separate component attached to it, and may, in one preferred embodiment, be free to rotate with respect to the cutting tool (which would be useful in preventing rotating bearing contact between the tip and soft tissue). The integral soft tissue protector in beneficial in preventing or mitigating contact between soft tissue near the area where the cutting tool enters, cuts, and exits the wound (in other words, to the right and left of the bushing body shown in FIG. 13). If the incision is pictured as being a window into the joint which is somewhat elastically moveable from side to side, the integral soft tissue retractor would act to shift that window to mitigate or prevent contact between the soft tissue (specifically the patella tendon, medial or lateral collateral ligaments, the capsule, skin, fat, etc.) and the cutting surfaces of the cutting tool.

Figure 15:
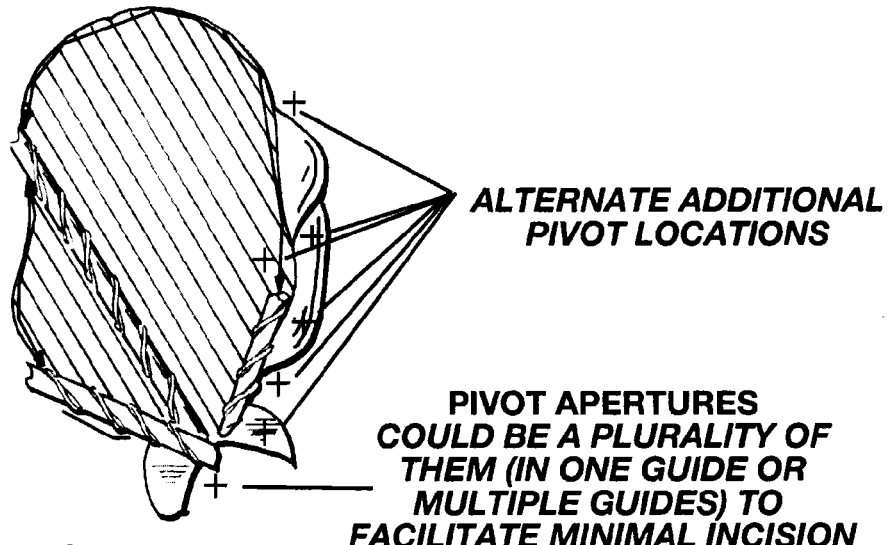

In operation, the guide is properly positioned with respect to the proximal tibia and the cut to be created thereon and robustly fixed with respect to the tibia or directly to the tibia. This can be accomplished by manual alignment means outlined in U.S. Pat. No. 5,643,272 for manually positioning guides then fixing them in place, or use the '272 apparatus and methods to create the fixation apertures shown in FIG. 11 or 12, or use the Surg Nav techniques described herein as shown or in conjunction with the methods described in the '272 patent. The bushing body is then engaged with the guide. Three primary methods of initiating cutting of the proximal tibia are preferred. The first, or 'Tangent Method', is initiated by extending the side cutting drill through the bushing body cannulation and into contact with a side of the tibia and then sliding the optional non cutting tip along the face of the bone until the cutting surfaces of the cutting tool were first in contact with the side of the bone. At this point, the cutter could be actuated to begin cutting the boney tissue to create the cut surface. As the non-cutting tip cannot cut bone, its edges would remain at all times immediately beyond and adjacent to the boundary of the cut surface being created. The diameter or size may be greater or less than the diameter or size of cutting surfaces of the cutting tool. Note that although the embodiment of the cutting tool shown is a side cutting drill, a modified rat tail rasp driven by a reciprocating driver could also work well—any cutting tool capable of cutting in a direction orthogonal to its long axis is considered to be within the scope of the present invention. As best represented in FIG. 15, the entirety of the resected surface may be prepared in this manner.

The second primary method is the 'Plunge Then Sweep' method. In this method, the cutting tool or optionally a pilot drill would be plunged completely or partially across the surface to be cut. Then the cutting tool could be swept back and forth in clockwise and counter-clockwise directions while being axially manipulated to complete the cuts.

The third primary method is the 'Chop Then Sweep' method represented in comparing FIGS. 88 and 89. In this method, the cutting surfaces of the cutting tool are positioned over and at least partially across the uncut bone, then chopped down into it by manipulating the bushing. In other words, the bushing pivot pin is engaged with the pivot aperture with the cutting tool positioned over the bone which positions the bushing reference surface at a distance above the pivot reference surface, then the bushing is moved downward along the axis of the bushing pivot pin while the cutting tool is under power until the cutting tool reaches the cut surface to be created (if the cutting tool is a side cutting drill, the cutting surfaces would be tangent to the desired cut surface at that time). The bushing is then manipulated as described hereinabove to complete the cuts. Importantly, the pivot reference surface and pivot aperture could be slidably mounted to a base component fixed with respect to the tibia so that the surgeon may manipulate the bushing body to simultaneously create the cut and move the pivot aperture with respect to the tibia. This embodiment will enable the surgeon to easily compensate for any soft tissue condition encountered clinically while preserving the benefits of the present invention. Methods combining the aforementioned primary methods are considered to be within the scope the present invention. Importantly, most standard or prior art tibial resection cutting guides may be simply modified to include the pivot apertures described herein.

Figure 16:
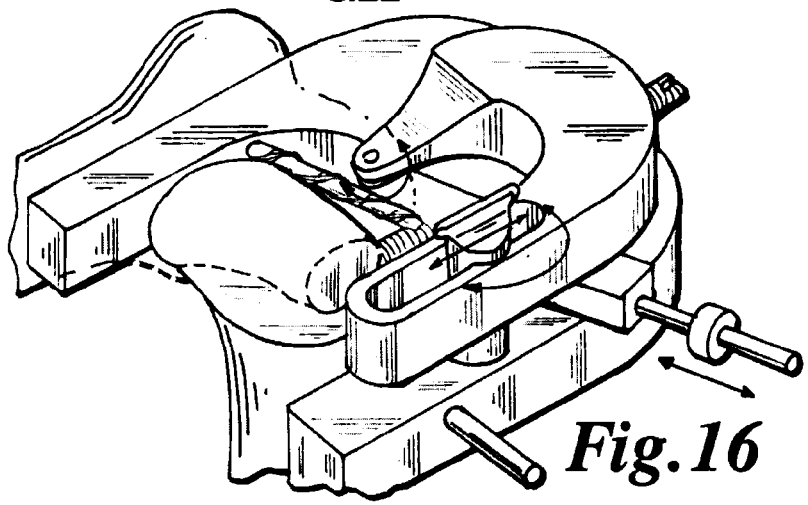
Figure 17:
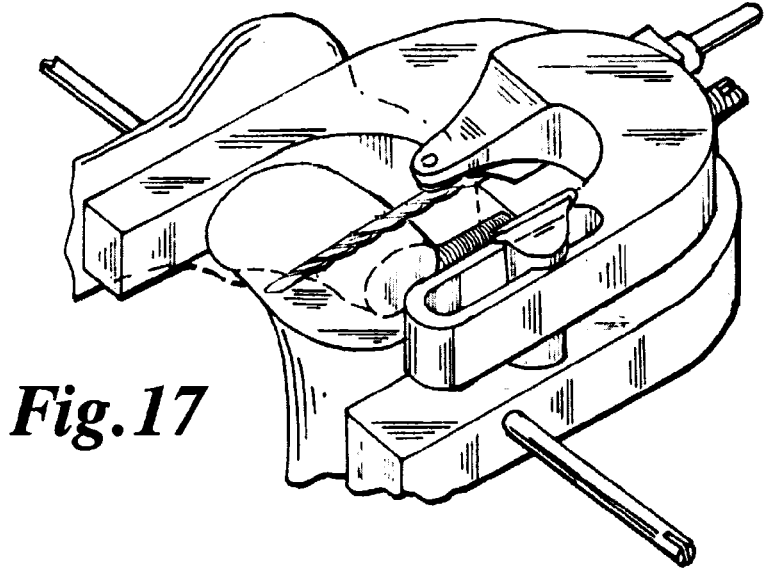
Figure 21:
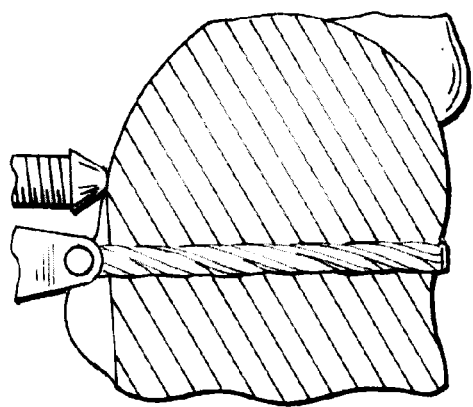
Figure 22:
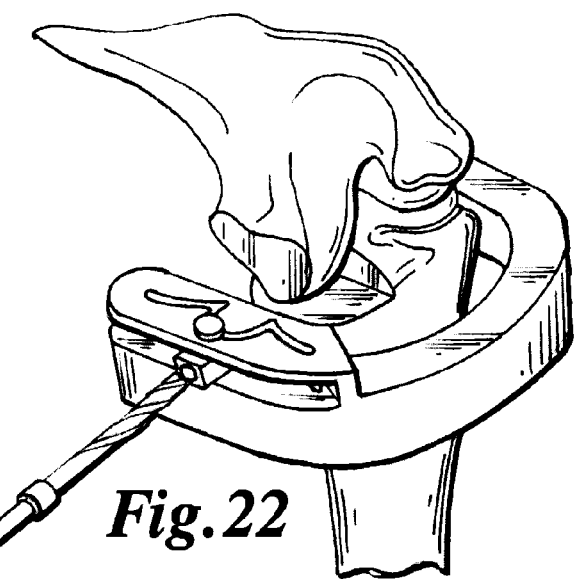
Figure 23:
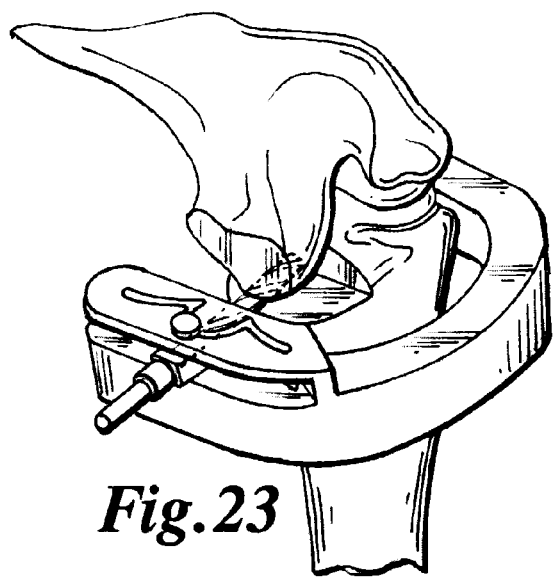
Figure 24:
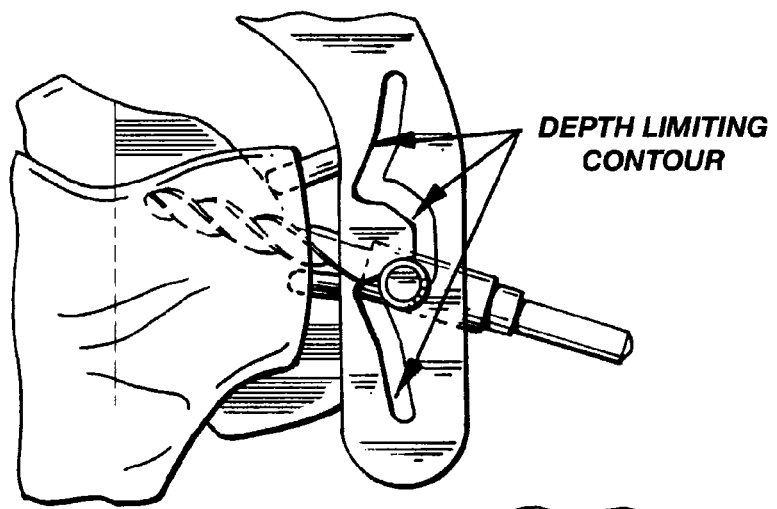
Figure 25:
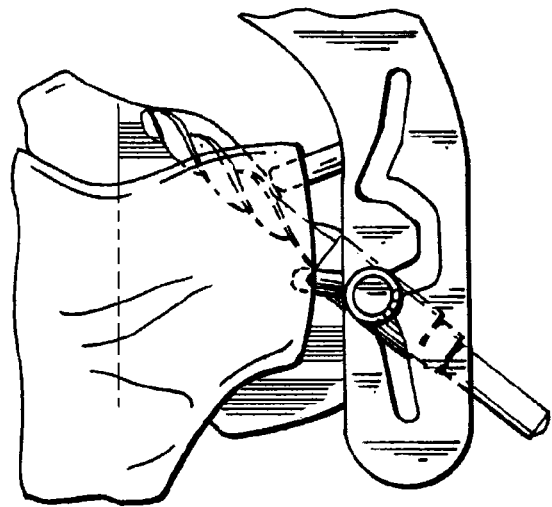
Figure 26:
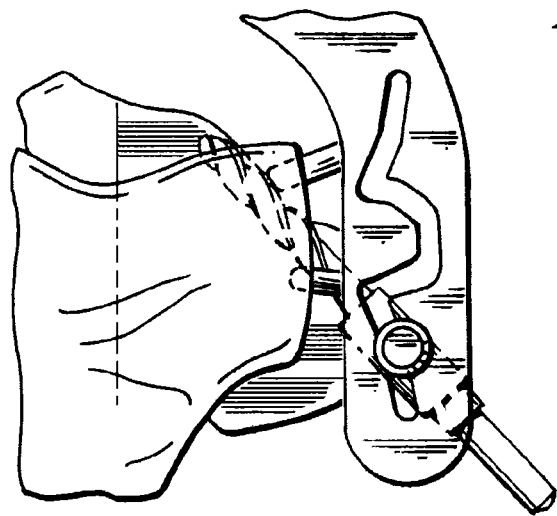

FIGS. 16 through 21 describe another embodiment of the present invention. As shown in FIG. 16, this embodiment includes a Base and a Rotational/Translational Pivot Arm coacting to allow for infinite manipulation of the bushing pivot pin location within a desired plane during the process of removing material from the proximal tibia or other bone. Movement of the Rotational/Translational Pivot Arm in both rotational and translational degrees of freedom within a desired plane allows for any combination of rotational and translational movement of the axis of the bushing pivot pin within its desired plane. In other words, this embodiment of the present invention allows for infinite and continuous adjustability of cutting tool location and orientation with respect to the bone or bones being cut while providing for accurate and precise cut surface creation.

FIGS. 22 through 28 represent another embodiment of the present invention whose principal of operation are similar to previous embodiments, with the exception of including a depth limiting contour which acts as either a definitive limitation for cutting tool depth or as a general guideline for a surgeon to follow as the patient's clinical presentation and the surgeon's judgment dictate. Although the embodiment shown is directed toward Unicondylar tibial preparation, it should be noted the any clinical application where such definitive or guideline type depth guidance is desirable.

Figure 30:
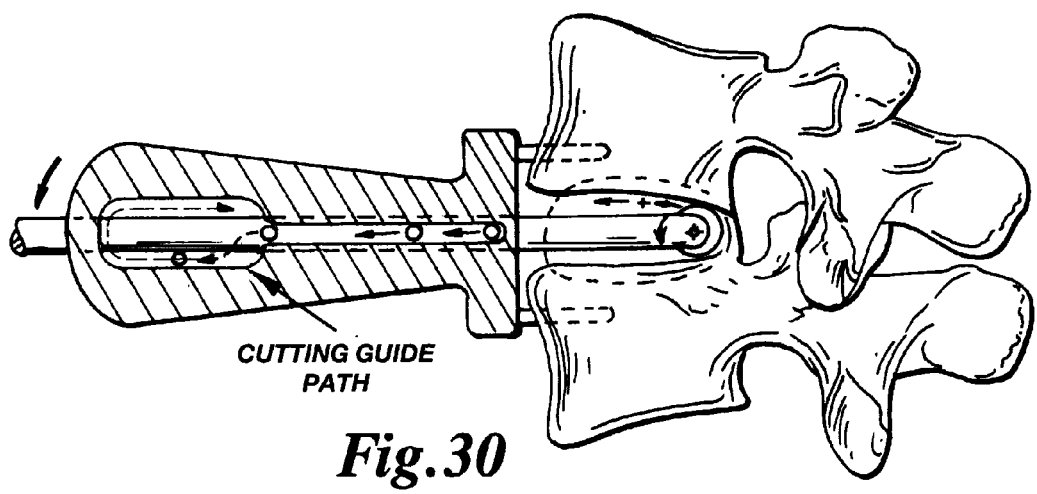
Figure 31:
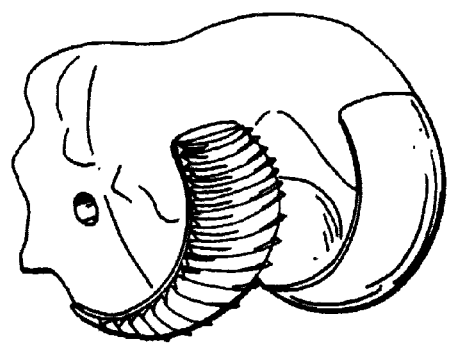
Figure 32:
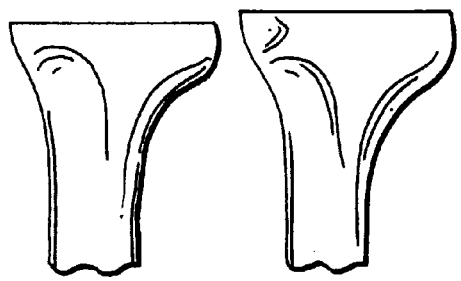
Figure 33:
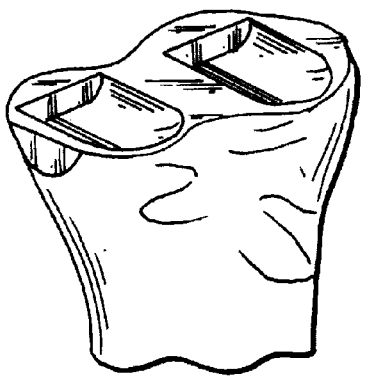
Figure 34:
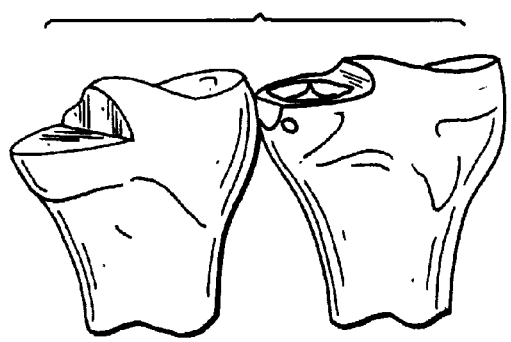

FIGS. 29 and 30 show an embodiment of the present invention directed toward endplate preparation in spinal reconstruction where the endplates are prepared to receive a prosthetic implant. It is interesting to note that the profile of the cutting path of the guide represented in FIG. 30, in this embodiment, is geometrically identical to the cutting path of the resected surface created by the passage of the cutting tool shown. This could be very helpful in clinical application where such a device where inserted into a wound such that, while the surgeon could not visually observe the cutting tool while it removes boney material, he could, by way of the guide geometry, observe where the cutting is with respect to the bone being cut by looking at the position (represented by "POS 1" and "POS 2") of 'Pivot 2', represented in FIG. 30, with respect to its location in contact with the guide as it traverses the cutting path of the cutting guide. This embodiment is also highly applicable to tibial resection and could allow for cut geometries that are anatomically curved in both AP and ML profiles to both preserve bone and improve fixation quality and load transfer characteristics between the implant and the bone by converting the shear component load of conventional planar tibial components into compressive loads via geometrically normal or transverse abutment of bone and implant surfaces in the direction of A-P and/or M-L and/or torsional shear loading. An implant design embodying fixation geometries for mating with such cut surfaces is highly desirable. In one embodiment of such a tibial prosthesis design, the fixation surfaces would be intended to mate, directly or indirectly, with cut surfaces represented in FIG. 33 and/or 34 (the tibia in the right side of the FIG. 34). In essence, the tibial implant would possess a planar or gently curvilinear 'rim' for contacting the 'cortical skim cut' surface (represented in FIG. 32), and convex fixation surfaces for direct or indirect fixation to the concave tibial cuts represented in FIGS. 33 and 34. Direct fixation to such surfaces could be achieved by high precision resection of both the cortical rim, for attachment of the rim of the tibial prosthesis, and the concave surface(s), for intimate apposition to the convex implant surfaces. Such fixation, specifically of the concave bone cuts to the convex implant surfaces, could be achieved by way of an interference fit between the cuts and the implant along one axis (for instance, a front to back—AP—axis or direction), or along two axes (for instance, AP and Side to Side—ML—axes), or circumferentially (in other words a bit like a pin of a given diameter being forced into a hole of a lesser diameter), or both circumferentially and along an axis at roughly a 90 degree angle or normal to the skim cut surface when viewed in one or two orthogonal planes (an "up and down axis" or superior-inferior or proximal distal direction). It should be noted that an interference fit in a roughly superior-inferior direction may call for a textured surface on the bottom most surface of the convex fixation surfaces presents a small surface area of contact at initial contact with the bottom of the concave cut to allow the implant to compact a reduced area of cancellous bone as the implant is impacted in a superior to inferior direction until it reaches its desired superior-inferior location and/or contact between the rim of the implant and the skim cut of the cortices. As compared to previous methods of achieving implant fixation, these embodiments of the present invention yield superior stability of implant fixation to bone to an extent reminiscent of the difference between riding a horse wearing a deeply dished saddle and riding a very sweaty horse bareback.

An alternative fixation paradigm allows for less intensive demands for the precision of the fit between concave tibial cuts and convex fixation surface. In essence, the concave surface may be 'excavated' in any desired manner (such as the Cutting Trials shown in FIG. 31 which cut the proximal tibia while the tibia is moved through at least a portion of its range of motion about the femur), and a morselized or granular osteobiological substance, perhaps tricalcium phosphate, HATCP, or other substances generally described as 'bone substitutes' or autograft or allograft cancellous or cortical bone (it would be very useful to use the bone which was removed from the tibia or other patient bone during the creation of the cut(s) in that it is readily available and completely avoids the issues of disease transmission or immune response), is then impacted into the concave surface using a 'form' to create a surface of impact material (referred to herein as the "Impacted Surface") of specific shape and location/orientation with respect to the cortical skim cut and/or the tibia or femur. This form is beneficially shaped in a manner related to the shape of the convex implant fixation surface shape so as to create a specific geometric relationship between the implant fixation surfaces and the Impacted Surface geometry. In one embodiment of the present invention, the fit between the implant and the Impacted Surface would be an interference fit or press fit. As properly impacted morselized cancellous bone is known to achieve stiffnesses (or modulus of elasticity) which approach as much as 80% of the stiffness of cortical bone in compression, robust intraoperative fixation may be achieved in this manner.

In another embodiment, the fit would leave a significant gap, perhaps 0.2 mm to 4.0 mm in width, between portions or all of the convex fixation surfaces of the implant and the convex cut(s), into which bone cement or other substance would then be injected or impacted achieving interdigitation with both the surfaces of the prosthesis and the material of the Impacted Surface. This results in what could be described as composite interface of both biologically active and non-living but structurally robust materials to facilitate both immediate intraoperative stability by way of simple mechanics and long term stability by way of improved load transfer between the implant and the bone eliciting a beneficial biological response by the bone to said loading resulting in intimate and mechanically robust apposition between the composite interface and living tissue. It should be noted that such a method prevents excessive micromotion or strain at the interface between the implant (and/or the composite interface) and living tissue during the postoperative healing process, which, in essence, gives the bone a chance to further stabilize its fixation to the implant by way of bone modeling or remodeling in response to load transfer. Specifically, it is highly beneficial to maintain the strain state within living bone at and/or in the general vicinity of the bone implant interface within a range of 50 microstrain to 4000 microstrain so as to elicit the formation of bone tissue at and around the interface—strain levels in excess of 4000 microstrain or less than 50 microstrain are very likely to elicit the formation of fibrocartilagenous tissues at the interface which may lead to aseptic loosening of the implant.

Figure 111:
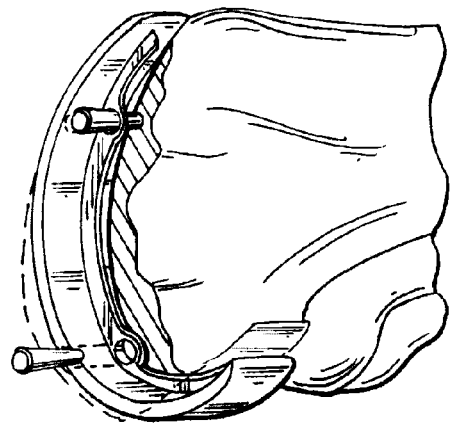
Figure 112:
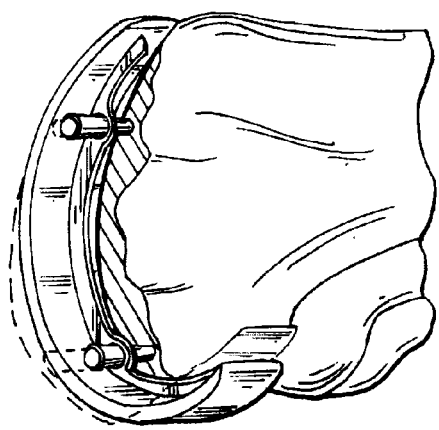

In the embodiment where the bone cement is injected, a small hole located at or beneath the skim cut allows for the injection of the material beneath the implant to achieve intimate and controlled interdigitation. Alternatively, the implant could be seated 'over' the freshly cut concave surfaces, and a slurry of biologically active and/or mechanically robust material(s) injected into the gaps between the implant and the bone under controlled pressure. Injection could be achieved via the portal shown in FIG. 34. Such a slurry may comprise a mixture of substances such as morselized patient bone and bone cement, but alternative or additional materials including bone substitutes, osteobiologicals such as bone morphogenic proteins, antibiotics, or even living cells such as T cells known to promote post-operative healing and long term implant fixation. Beneficially, a fin feature may be added to these embodiments to facilitate additional mechanical stability, and said stem feature could beneficially possess an aperture for cross-pin fixation as described below for use in conjunction with the cross pins represented in FIG. 111.

Importantly, it is an objective of the embodiments of the present invention to preserve living, structurally viable bone tissue to facilitate the efficacy of any subsequent revision procedures. Further, the location and geometry of the concave tibial cut allows for the use of a bearing insert (conventionally made of materials such as polyethylene or other materials capable of 'whetting' or mimicking the benefits of 'whetting' during bearing contact; mimicking constituting, in one embodiment, the absence or mitigation of wear debris generation despite the application of significant bearing forces, in TKA in excess of 200 lbs and often as much as 500 lbs or more) whose 'underside' is convexly shaped to mate with a concavely shaped mating or accommodating surface in the upper surface of the tibial implant or 'baseplate' as it is sometimes referred to. This allows for a tibial insert(s) whose thickness, in the areas beneath where the femoral implant bears against the tibial insert, may be equal to or greater than those insert thicknesses used in the past (those associated with predominantly planar tibial cuts) while require removal of significantly less structurally viable bone from the cortical rim of the proximal tibia than past efforts. Determination of the geometry and location of the baseplate's concave surface and therefore the areas of greatest insert or bearing surface are easily determined by analysis of the wear patterns of retrieved tibial inserts. These embodiments of the present inventions also facilitate significant clinical benefits when applied to meniscal or rotating platform TKA designs as a high degree of conformity may be achieved while constraint is mitigated while preserving significantly more bone than prior art devices. Further, the reproducibility of the methods and apparatus described herein enable independent attachment of single compartment implants to bone to achieve Unicondylar, Bicondylar, Bicondylar and Patellofemoral, or Unicompartmental and Patellofemoral replacement of damaged bone surfaces while achieving the objectives of bone preservation, robust immediate and short and long term fixation, reproducibility of implant fixation and resulting location and orientation, and intraoperative ease of use.

It should be noted that the cutting profile of the cutting tool shown in FIG. 29 is curved in manner beneficial to endplate preparation in intervertebral fusion, dynamic disc replacement, and/or nucleus replacement as the cutting profile closely approximately the natural geometry of the endplates and provides for intimate fit with such prostheses fixation surfaces. In adapting this embodiment to tibial resection in either partial or complete knee replacement, the cutting profile of the tool would be shaped as desired to create the aforementioned cut surfaces in either one continuous movement of a single cutting tool, or incremental use of one or more cutting tools to cut bone to the desired shape and in the appropriate location and orientation, in all degrees of freedom, with respect to the tibia and/or femur and/or patella and/or soft tissues of the knee joint.

Figure 35:
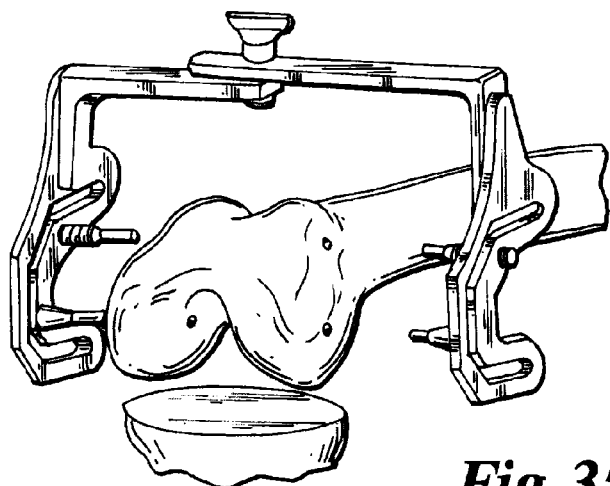
Figure 36:
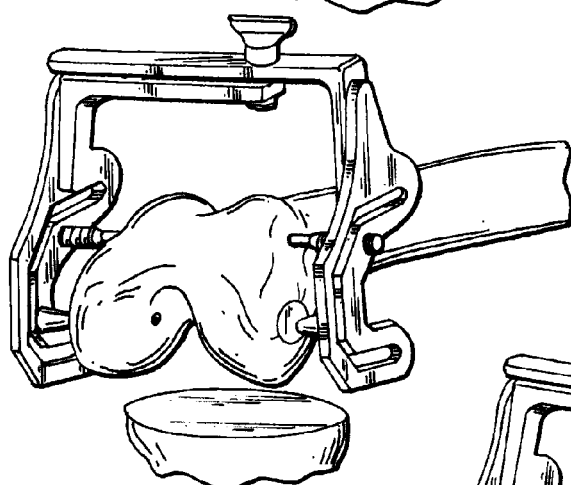
Figure 37:
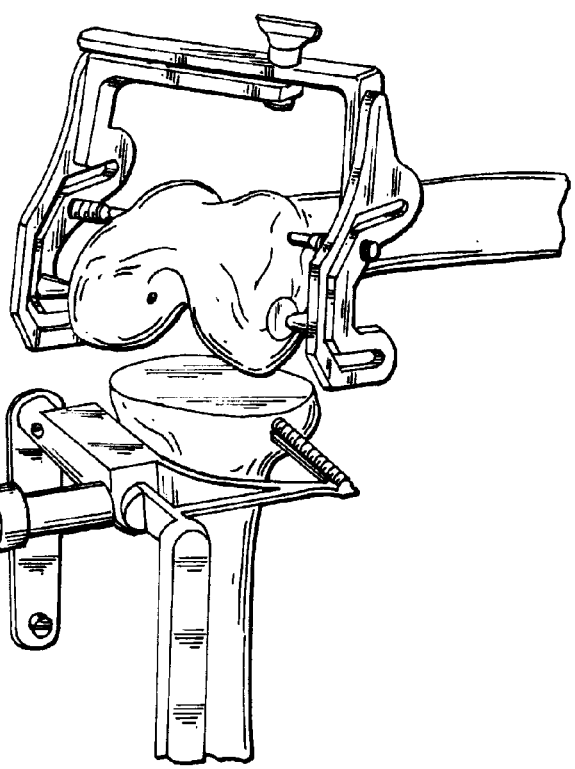
Figure 41:
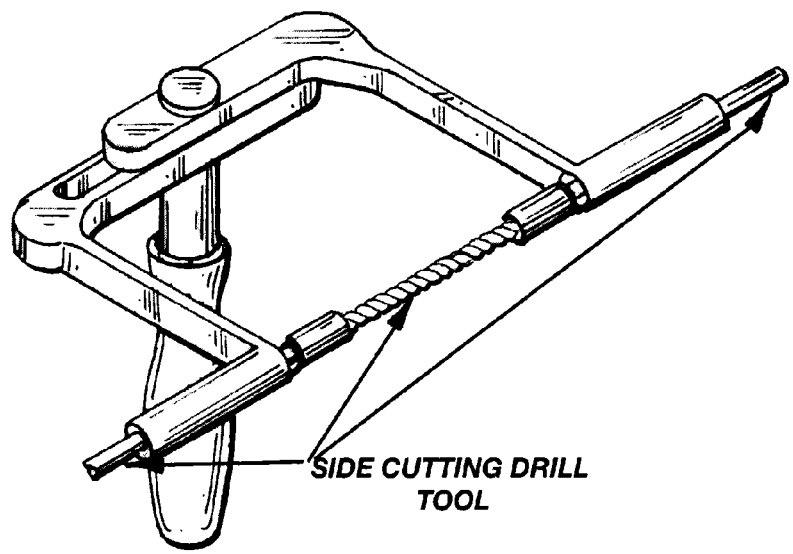

In many applications of the tibial resection embodiments and methods described herein it is desirable that the Superior-Inferior thickness or diameter of the cutting tools used be less than the thickness of the bone to be removed in the creation of the cut surfaces so that the cutting surfaces of the cutting tool not contact soft tissue surface and bone surfaces located above the bone being removed. Alternatively, the cutting tool could be of such a thickness or diameter as to allow for the resection of both the femur and the tibia, or any such contiguous bones, to be prepared simultaneously with the passage of the cutting surfaces of a single tool across or along cut surfaces being created on both bones. Maintaining the desired geometric relationships between the contiguous or adjacent bone ends would be key in this embodiment of the present invention and could easily be obtained and maintained by use of a bracket fixed to the bones to establish and maintain the geometric relationship between said bones (see FIG. 30 for one embodiment of such a bracket employed to establish and maintain alignment between adjacent vertebral bodies.
FIGS. 35 through 98

FIGS. 35 through 98 show embodiments of the present invention for femoral resection. For the sake of clarity, it should be noted that any combination of the forms of the present invention disclosed herein may be modified or combined to form constructs not specifically disclosed herein, but still within the scope of the present invention. The embodiments represented in FIGS. 29 and 30 are outstanding examples of this, as one of ordinary skill in the art would clearly recognize the applicability and benefits of this embodiment for tibial and/or femoral resection in Unicondylar or Bicondylar procedures, for bone resection in ankle replacement or arthrodesis (fusion), mandibular advancement procedures, high tibial osteotomy procedures, proximal femoral and acetabular preparation in Hip Arthroplasty, and a list of other applications too long to list in detail where reproducible and safe removal of living tissue during surgical intervention is beneficial.

FIGS. 35-40 show embodiments of the present invention for use in a manner similar to that described in previously-referenced co-pending provisional application, entitled "METHOD AND APPARATUS FOR WIREPLASTY BONE RESECTION."

FIGS. 35-40 shows an embodiment of the present invention wherein the guide plates and guide surfaces are located entirely outside the wound, but the side cutting drill and handle construct are not passed through mediolateral soft tissue portals described hereinabove. The side cutting drill controlling portion of the handle is essentially 'snaked' into the less invasive wound/exposure/approach/incision and the guide engagement features are engaged to the cutting guide at a location entirely outside the wound. As long as the axis of the engagement feature is maintained as coaxial with the side cutting drill, the desired cut geometries will be attained despite manipulation of the handle with respect to the guide. This method can be utilized to complete some or all of the desired cuts. Also, this embodiment of the current invention can be used to perform the posterior cut, posterior chamfer cut, and distal cut optionally using kinematic resection to reduce exposure requirements, and then removed from the wound and guide, flipped over 180 degrees from the orientation shown in FIG. 39, reinserted into the wound and into engagement with the guide to cut the anterior chamfer cut and anterior cut with or without implementation of a kinematic resection technique and, optionally, with the knee in 15 degrees to 45 degrees to facilitate the soft tissue laxity and ease of use previously described. It should be noted that the mechanism for driving the side cutting drill is not represented in these figures and that a number of different options may be used.

Figure 116:
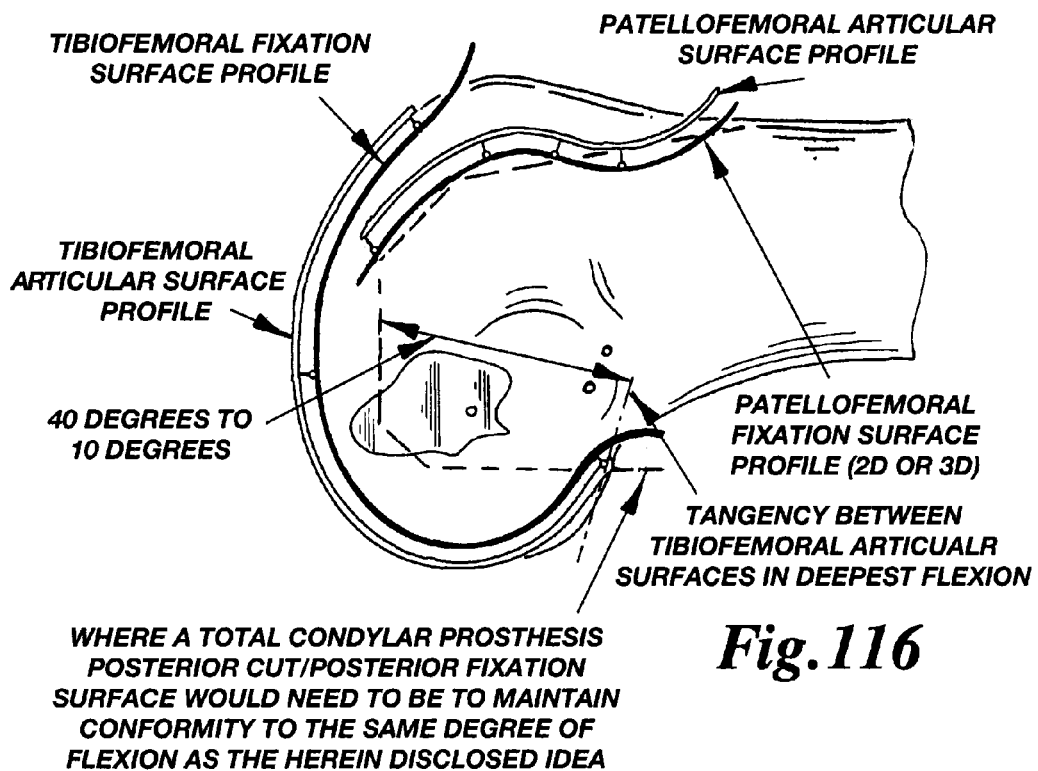
Figure 121:
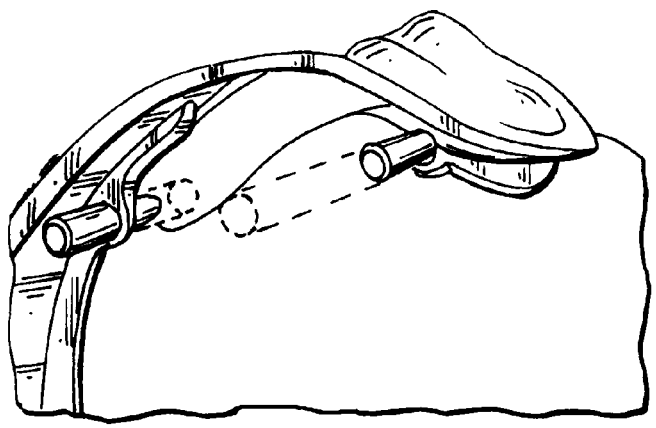
Figure 122:
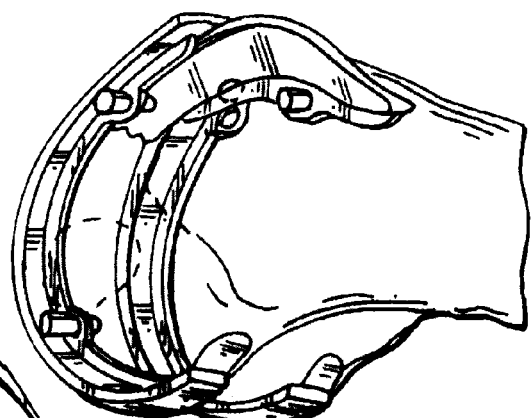
Figure 125:
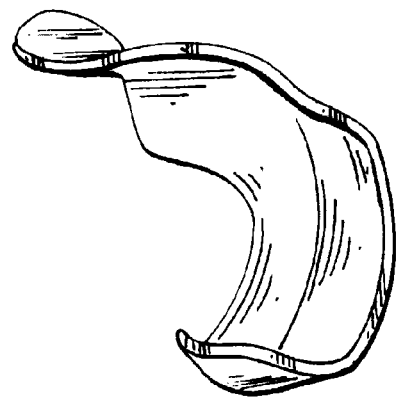
Figure 126:
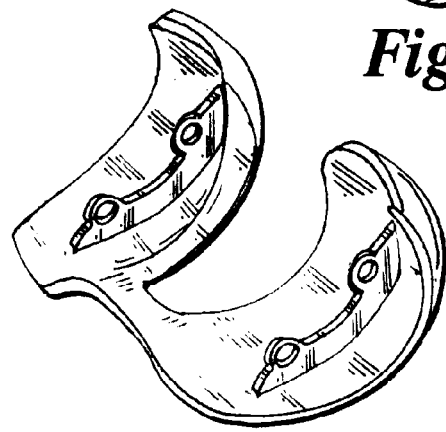
Figure 127:
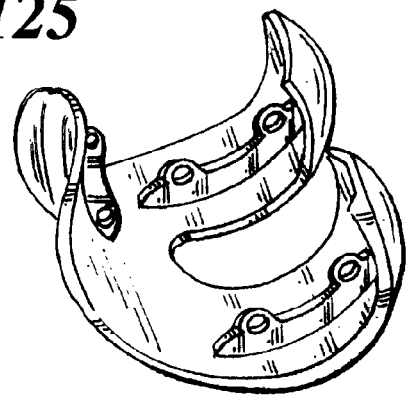

One way to accomplish drive input is generically represented in FIG. 40, where a flexible drive shaft or bevel gear arrangement may be utilized to drive the side cutting form drill shown. Alternatively, chain, belt, or pneumatic drive mechanisms may also be used. FIG. 40 also represents an embodiment of the present invention which allows for the accurate and precise preparation of curvilinear cut surfaces, beneficially used in conjunction with guides containing curvilinear guide surfaces as represented in FIGS. 61 and 62, to create cut surfaces for intimate attachment and fixation to implants represented in FIGS. 125, 126, and/or 127. FIGS. 116, 117, and 118 show representations of the cutting paths of cuts for seating conventional total condylar implants compared with the cutting paths of this embodiment of the present invention. These figures also demonstrate the dramatic degree to which viable bone preservation may be achieved while simultaneously providing for superior fixation and Range of Motion with articular conformity. This improvement in articular surface conformity in the deepest ranges of motion of the knee joint is especially critical for physically active patients and in cultures where deep knee flexion is needed to squat or kneel. As is noted in the figure, conformity between the tibiofemoral articular surfaces of the femoral component and the tibial bearing surface may therefore be maintained in deepest flexion to as much as 140 degrees of flexion to 170 degrees of flexion depending on the activities of the patient. Prior Art implants, such as the one shown in the radiograph ("xray") FIG. 113, do not offer such benefits.

Figure 42:
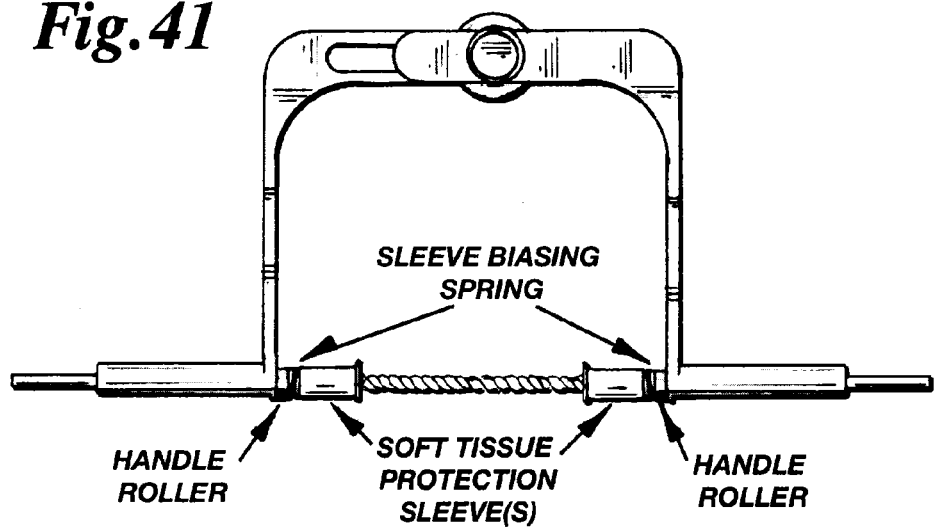
Figure 43:
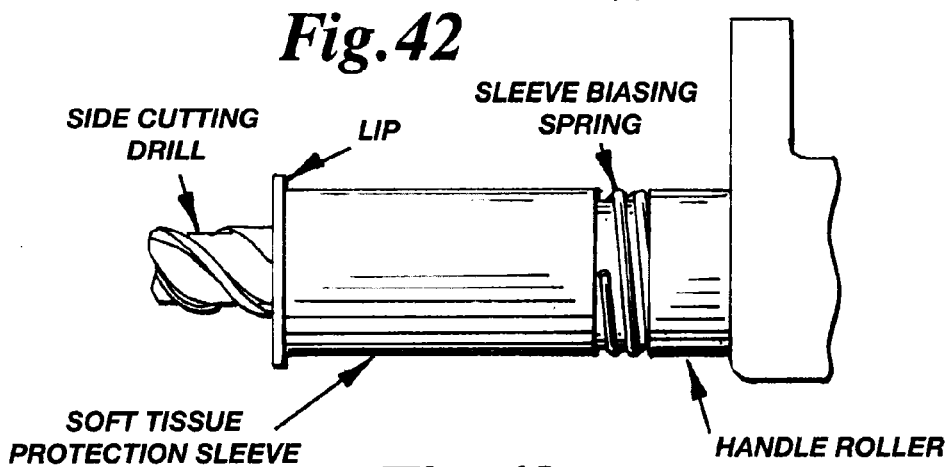
Figure 48:
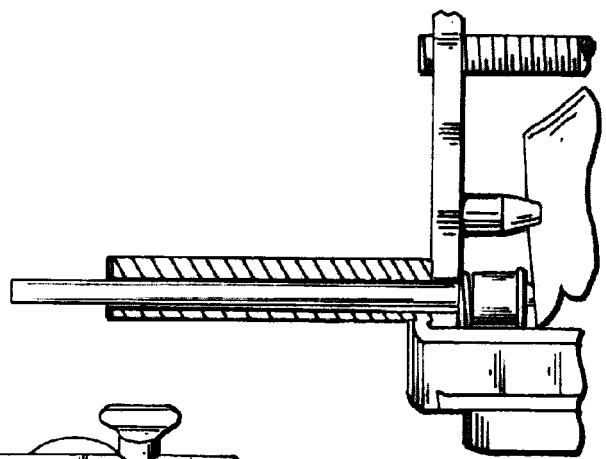
Figure 49:
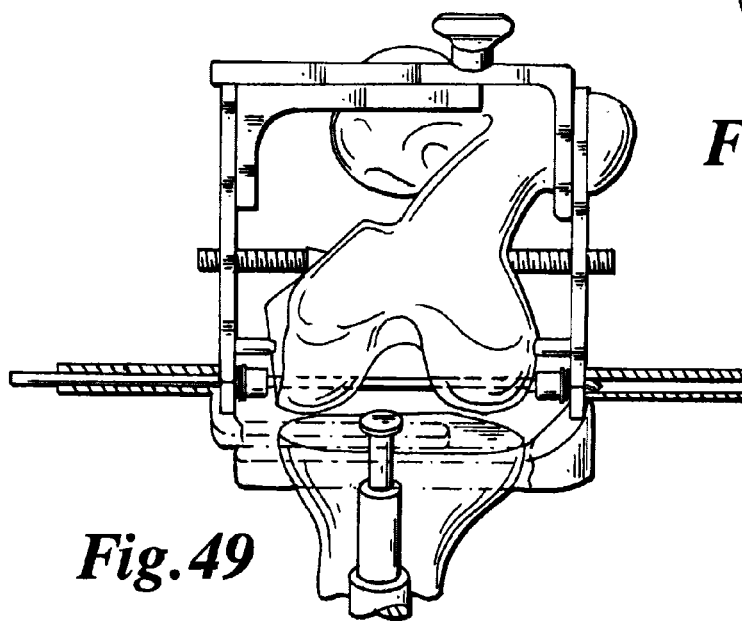
Figure 50:
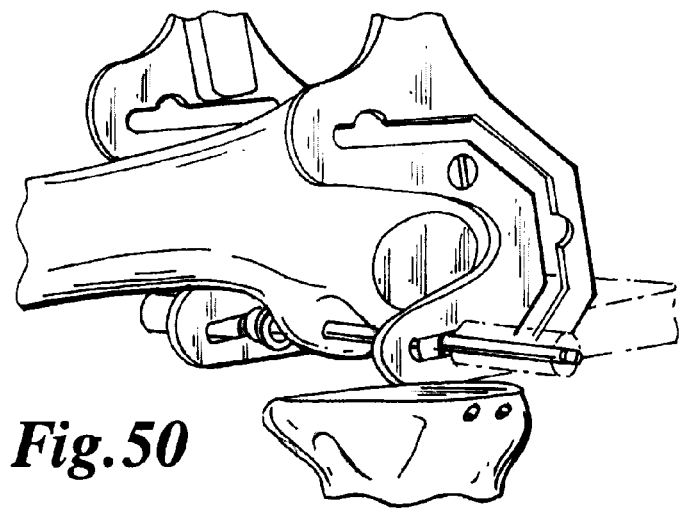
Figure 53:
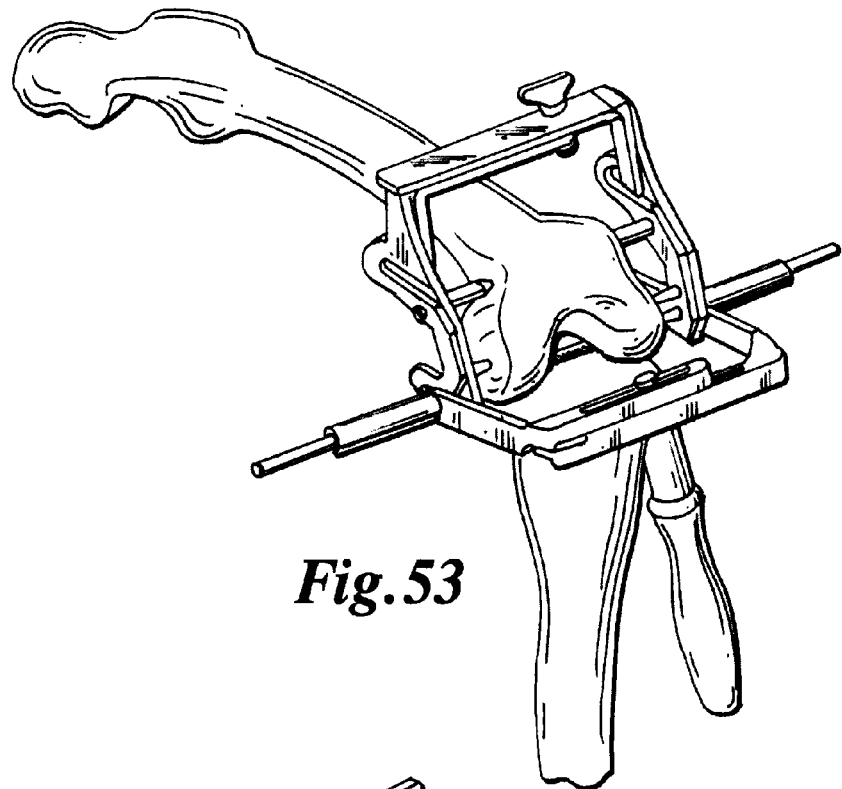
Figure 54:
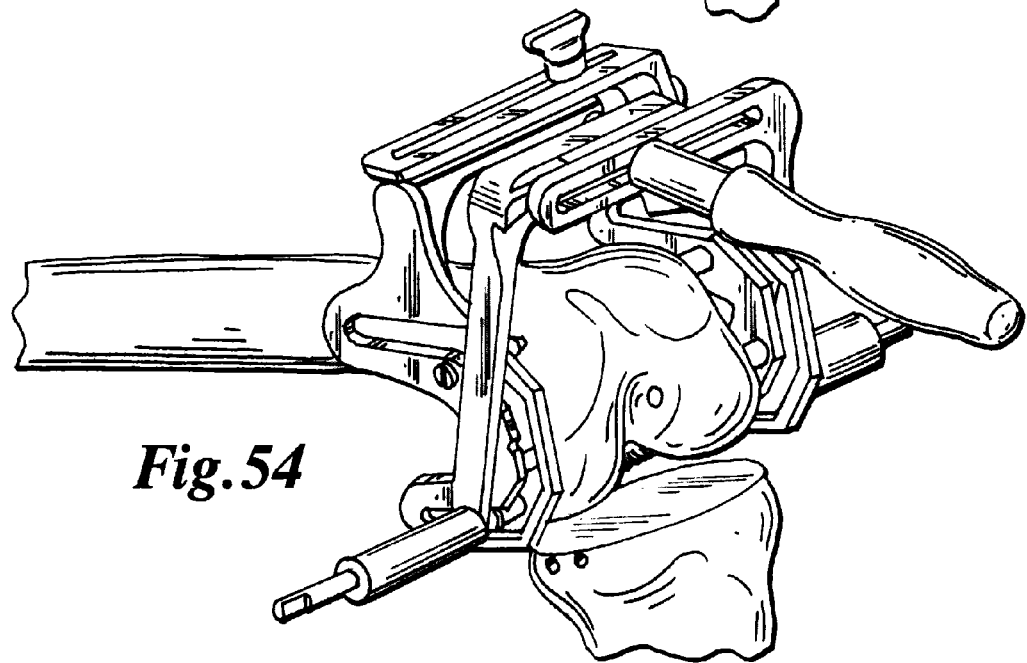
Figure 55:
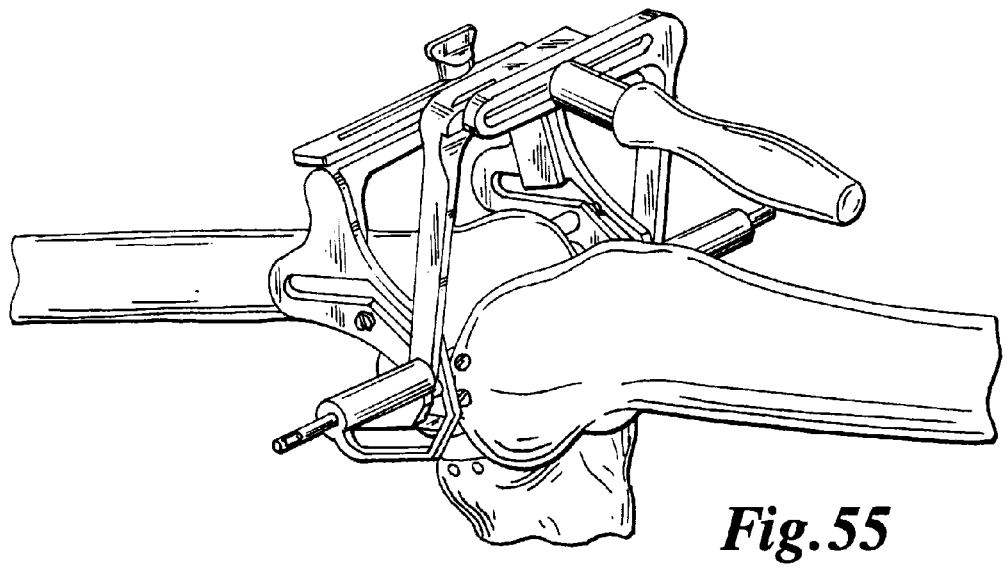
Figure 56:
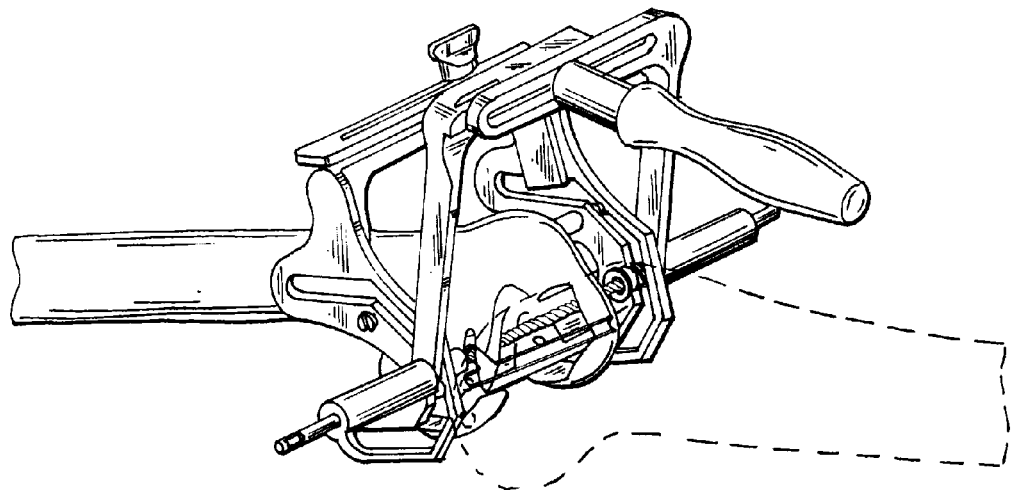
Figure 57:
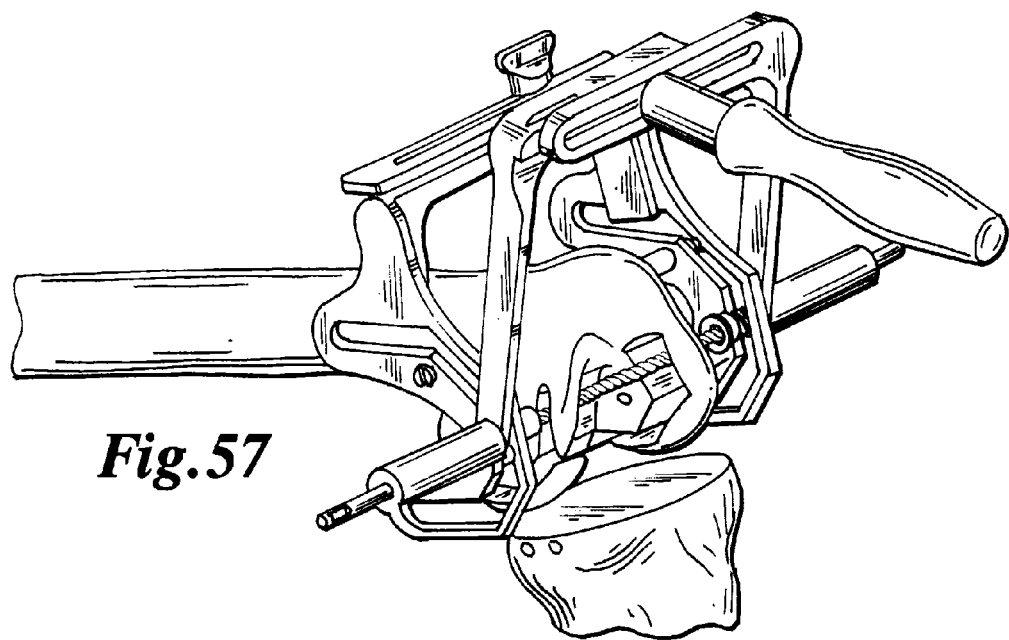
Figure 58:
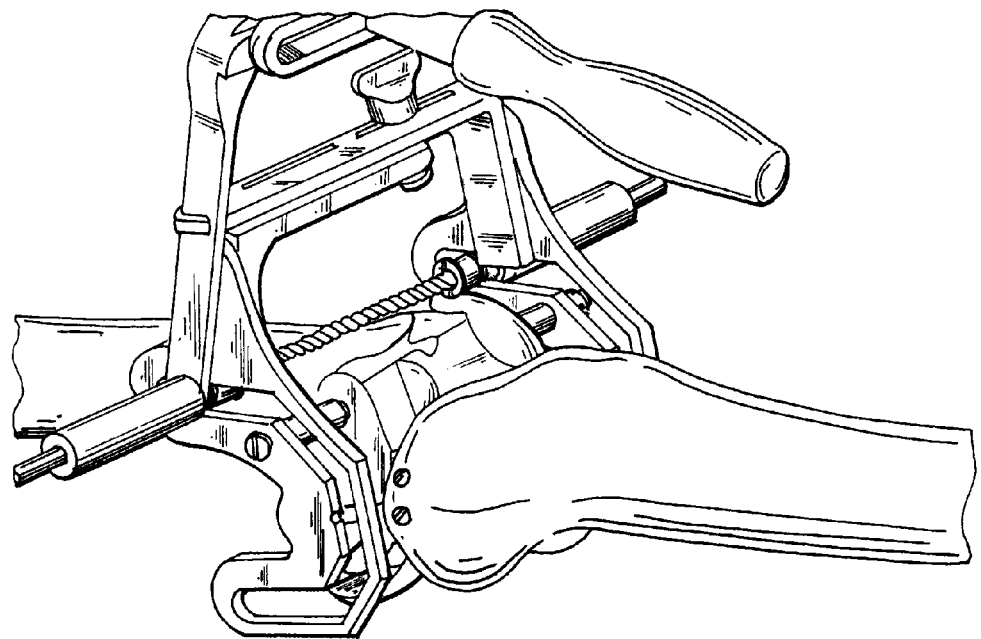
Figure 59:
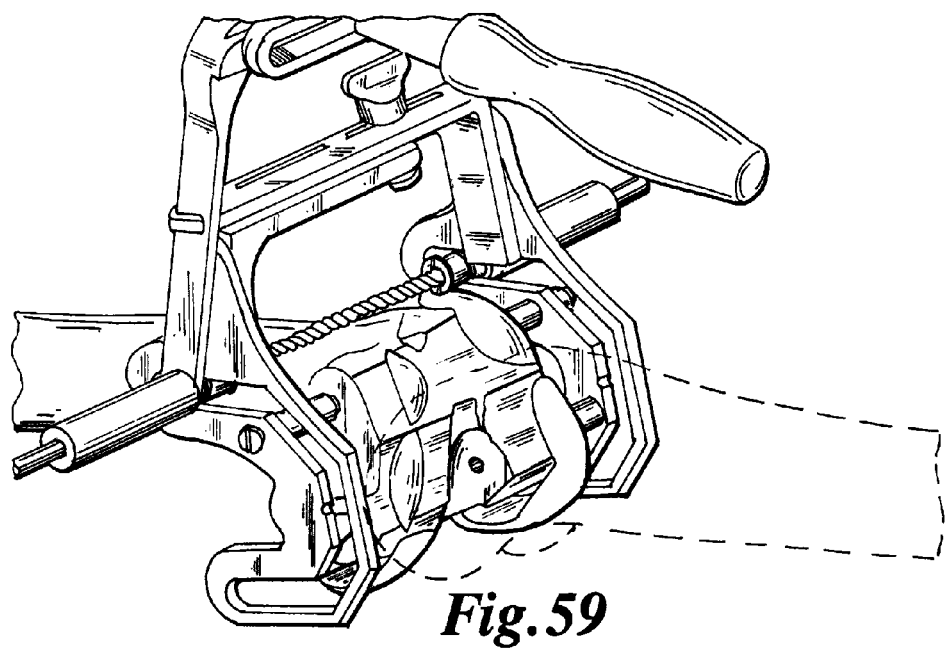
Figure 60:
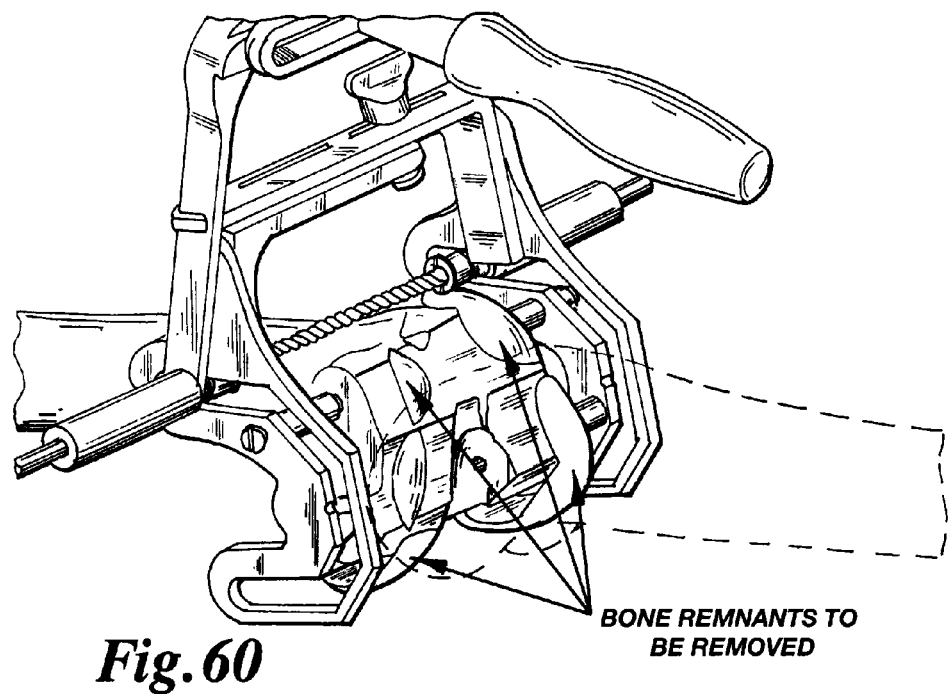

FIGS. 41 through 60 represent an embodiment of the present invention for Triple TKA, similar to that described in the previously-referenced application entitled, "METHOD AND APPARATUS FOR WIREPLASTY BONE RESECTION". As noted in that provisional application, an additional feature that may be desirable to add to different embodiments of the present invention are the soft tissue protection sleeves shown in FIGS. 42 and 43. One clinical application calling for the benefits of this feature would be Transcutaneous Transarticular TKA ("TTTKA" or "Triple TKA" or "T Cubed" or "$T^3$" Procedures) where a PBR cutting guide, as generally shown in FIG. 35 is positioned completely outside of the wound with the exception of fixation features which extend from the externally located guides through skin incisions and into holes or apertures created in bone. As shown in FIGS. 52 and 53, the cutting tool, in the case of the present invention a side cutting drill, is extended through the handle, the guide, the skin, fat, capsule, etc (soft tissue), across, across and in front of, through, or beneath the articular surfaces of the joint, and through the soft tissue, guide, and handle on the opposing side of the bone. The soft tissue protection sleeves may be extended through the soft tissue and into contact with the sides of the bone. The retaining lip can be used to maintain the sleeves in contact with the bone and are held there by the edges of the incision through the capsule during cutting. The springs shown in FIG. 43 can further bias the sleeves into contact with bone in a manner that would maintain that contact as the width of the bone changed along the cutting path of the resected surface.

One skilled in the art will note that the thicknesses for the soft tissue through which the sleeves extend change significantly from patient to patient thus requiring the proportions of the sleeve, spring and other components of the present embodiment of the invention to change accordingly. For example, in an obese patient, the fat layer through which the cutting tool extends can be 5 inches thick per side or more. The diameter of the soft tissue protection sleeve can be significantly reduced with respect to what is shown as the side cutting drill diameter is reduced, thus requiring a smaller capsular or other soft tissue incision or 'stab wound'.

In operation, the handle is manipulated to traverse the cutting path of the cutting guide while the tibia is swung through a range of motion about the femur as shown in comparing FIGS. 54 through 60. This particular principal of operation takes advantage of the fact that the capsule, the patella, and to a lesser or greater extent the skin, moves with the tibia as it moves through a range of motion with respect to the femur. Thus, a small, perhaps 4 mm to 10 mm long stab wound through skin to the medial side of the posterior femoral condyles (roughly in line with the axis of the pilot drill shown in FIG. 51) with the knee bent in flexion, and then looked at the side of the femur (through the portal created by the stab wound) while moving the tibia through a range of motion, the side of the femur would be observed to be passing by/through the portal. In order to complete all of the resected surfaces on the femur necessary to fix a standard femoral prosthesis, it may be necessary in one embodiment to make two passes with the side cutting drill sweeping about the femur with the tibia as represented in FIGS. 54 through 60.

Figure 68:
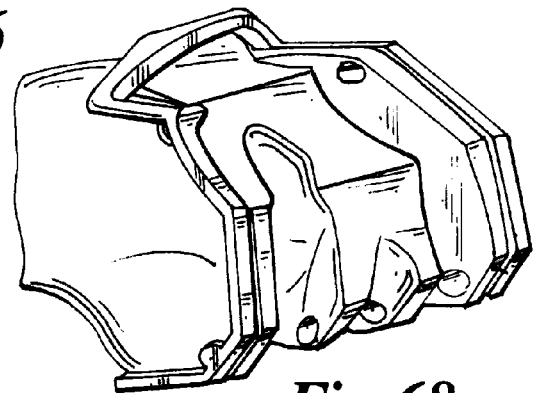

FIGS. 44 through 51 represent an embodiment of the present invention for use in creating pilot holes allowing for introduction of a side cutting drill or other cutting tool in Triple TKA or Unicondylar or Bicondylar procedures. Of particular interest, the pilot drill is designed to eliminate or mitigate any deviations of the drill from its intended location and orientation as it is guided to create portals in living bone. Standard drills tend to follow the path of least resistance into and through bone often resulting in either poor drill placement, and thereby poor cutting guide placement, or improperly located and oriented portals or apertures for fixation of a cutting guide resulting in poor cutting guide placement. As shown in FIG. 44, the pilot drill possesses cutting teeth that are very aggressive in side cutting. This is critical in that it prevents deflection of the cutting tool when it contacts tissue of varying material properties. This area of very aggressive side cutting teeth is relatively short, and is followed by a longer smooth portion of the shaft of the drill which is designed to be incapable of cutting bone, but may beneficially include smooth flutes allowing for removal of chips during the cutting process. A pilot drill of this kind, optionally used in conjunction with the Surg Nav Drill Guide of FIGS. 8 through 11, would be outstanding for use in creating the apertures in bone desired for positioning the cutting guides. Specifically, the pilot drill may provide sufficient accuracy and precision of aperture creation to allow for drilling all the way through or across a bone to which a cutting guide will be attached to bone sides of the aperture as shown in FIG. 68, where the cancellous bone within the cortical shell is not shown for the sake of clarity.

In use with the embodiment of the present invention, with the soft tissue protection sleeves of the milling handle in contact with a bone surface, the pilot drill would be plunged through the bushings of the milling handle and across the joint, as shown in FIGS. 45 through 51. FIG. 51 represents the pilot drill having been plunged entirely across the joint, but with the milling handle not shown for the sake of clarity. Thus, a portal has been created across the entirety of the joint for subsequent insertion of the side cutting drill shown in FIGS. 52 and 53, or any other cutting tool. It should be noted that in embodiments adapted for use in Unicondylar knee replacement, it would only be necessary to create the portal in one side of the joint for extension of the cutting tool across only a single condyle (as is seen in comparing FIGS. 78 and 80). An alternative embodiment and method of the milling handle of the present invention represented in FIG. 54 would be to extend the side cutting drill, or other cutting tool, through a soft tissue portal on one side of the joint, across the entirety of the bone surfaces to be resected or cut, but not extend the tool through the soft tissue on the far side of the joint. As control of the side cutting drill by the milling handle is very robust, even when it supports only one spindle of the side cutting drill, accurate and precise preparation of the distal femur can be performed without necessitating a second soft tissue portal, and the soft tissue trauma associated with it, no matter how minor, on the far side of the joint.

Alternatively, a hybrid embodiment of externally and internally located guide surfaces would allow for high precision, high accuracy cutting without necessitating the creation of soft tissue portals for insertion of the cutting tool. This embodiment of the present invention may be attained by positioning one PBR cutting guide surface(s) in the wound (perhaps looking like the medial guide surface of the cutting guide shown in FIGS. 68 through 70) and interconnecting it with an externally located PBR cutting guide surface(s) (perhaps looking like the laterally located plate in FIG. 60). This would allow for single spindle guidance of the side cutting drill or other cutting tool in a very robust manner, while minimizing the trauma to soft tissues necessary to implement these embodiments. Furthermore, the use of these single spindle embodiments lend themselves to easy manipulation of the cutting tool in pivotally sweeping (see FIG. 85) a cut surface while manipulating the cutting tool axially with respect to the milling handle. Thus the anterior chamfer cut, distal cut, and posterior cut could be completed by sweeping the cutting tool along the cutting path of the cut surface, and the anterior and/or posterior cuts could be completed by pivotally sweeping the cutting tool as mentioned above while maintaining the stability inherent in guiding the milling handle on guide surfaces on opposing sides of the cut being created. This is beneficial in that the internally located guide surfaces could be truncated or shortened significantly allowing for both easier insertion into the surgical exposure and reduction in the exposure necessary to accommodate the embodiments in clinical use.

FIGS. 61 through 62, represent embodiments of the present invention for use in bone preserving resection techniques. As noted in FIGS. 61, 116, 117, and 118, a significant amount of viable bone tissue may be preserved while maintaining all functional paradigms of conventional TKA while improving articular conformity in the deepest ranges of flexion. It is of particular interest to note that this is especially applicable in improving the results of conventional Unicondylar implant performance, as the current state of the art makes minimal planar posterior cuts which prohibit articular conformity in deep flexion. This is something of a 'catch 22' as Unicondylar replacement is most often implemented in younger patients whom place higher functional demands, specifically they bend their knees more deeply than their older counterparts, on their implants, yet in an effort to preserve bone for revision, most uni's don't possess nearly the range of motion with conformity necessary. Thus a Unicondylar design incorporating deep flexion articular surfaces (as shown in FIG. 116) and corresponding fixation surfaces could simultaneously offer articular conformity and bone preservation for these younger or more physically active patients who are more likely to demand higher performance and require revision to TKA.

Figure 64:
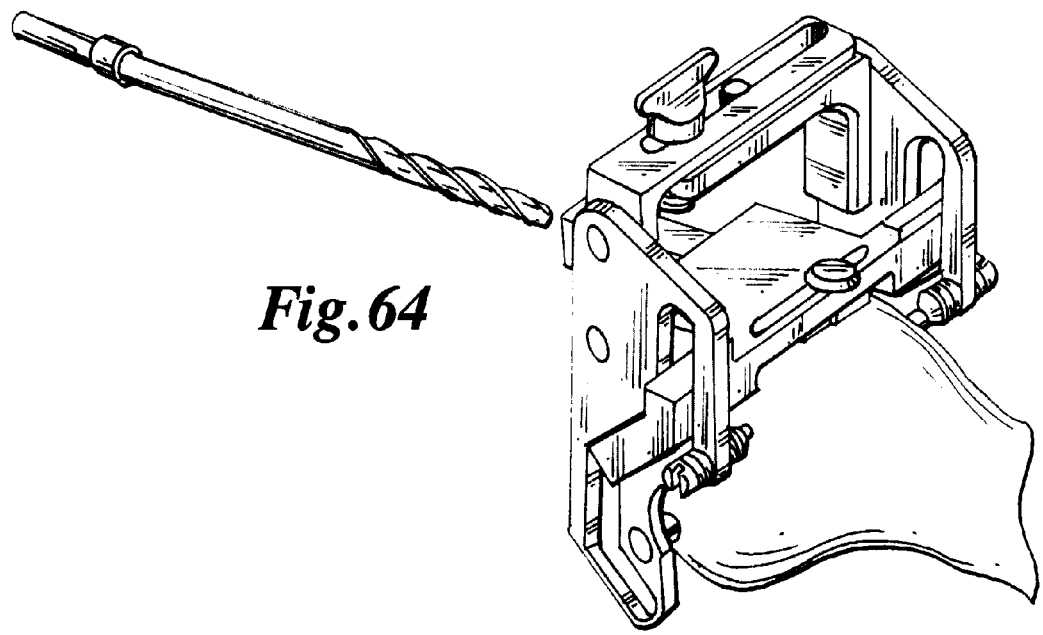
Figure 65:
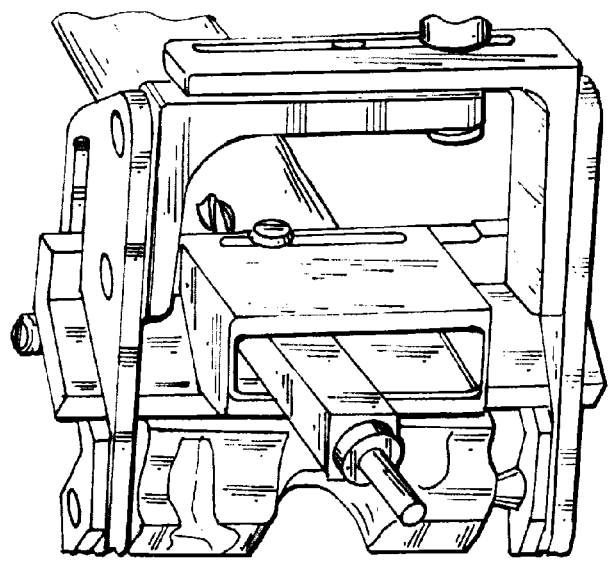
Figure 66:
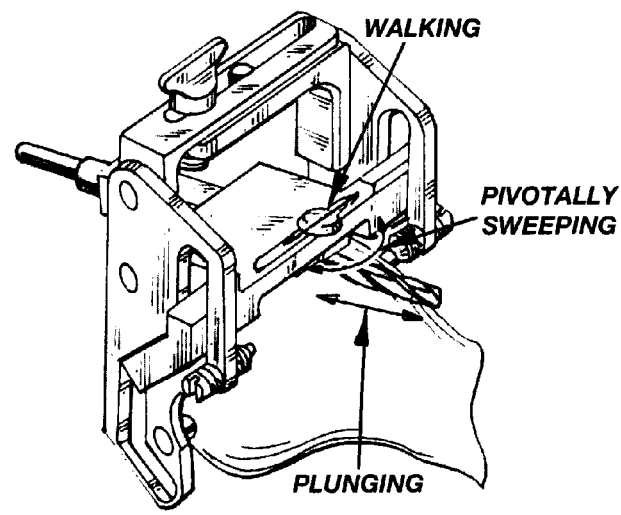
Figure 67:
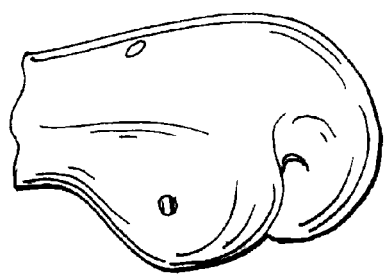

FIGS. 63 through 66 represent an embodiment of the present invention which would facilitate PBR cutting of, in one embodiment, the posterior chamfer cut, distal cut, and anterior chamfer cut, and any combination of plunging, pivotally sweeping, and walking manipulations represented in FIGS. 64 through 66 to complete the remaining cuts.

Figure 69:
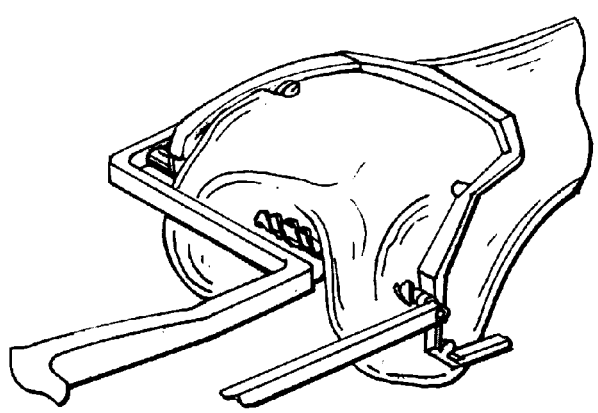
Figure 70:
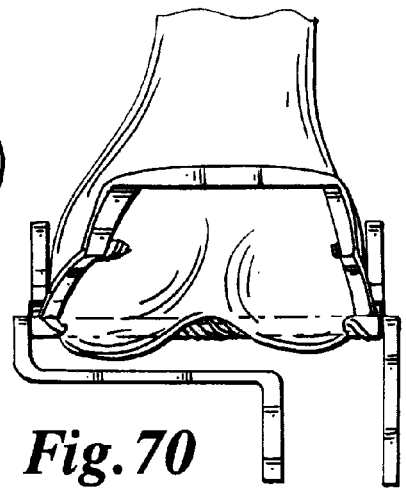
Figure 71:
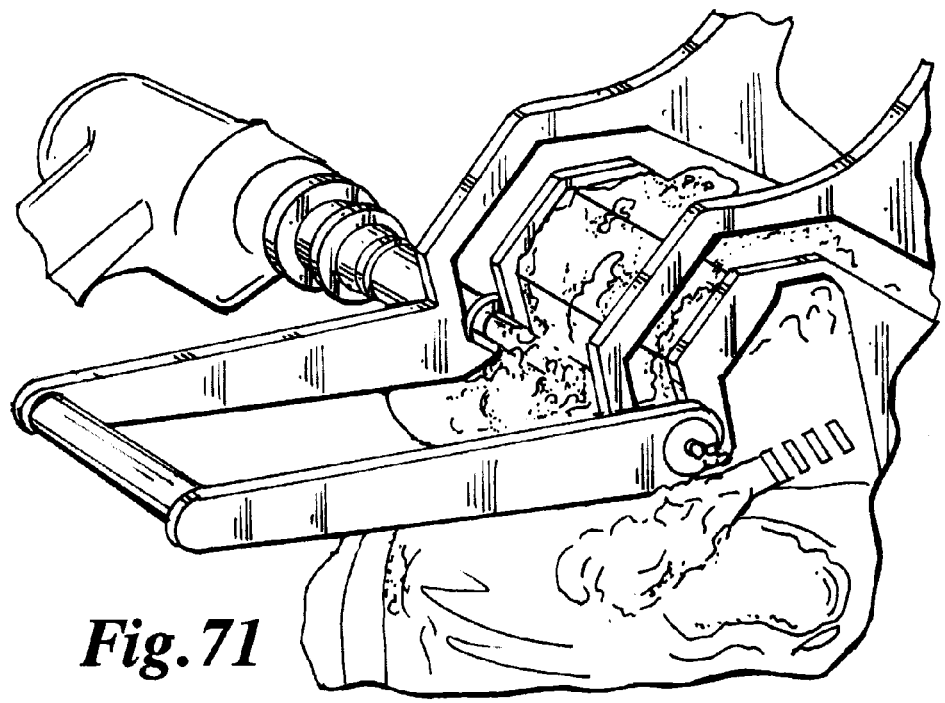
Figure 72:
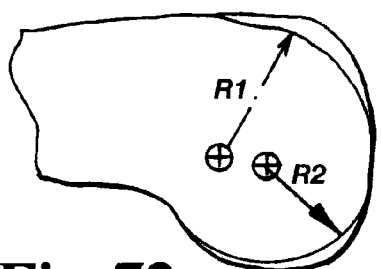
Figure 73:
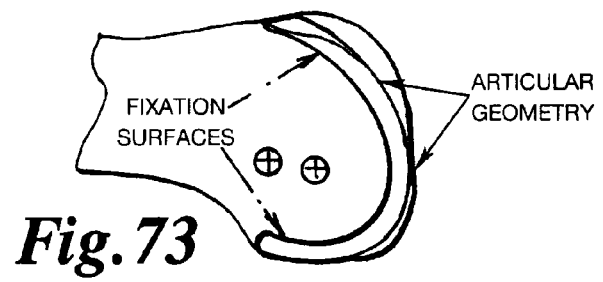
Figure 74:
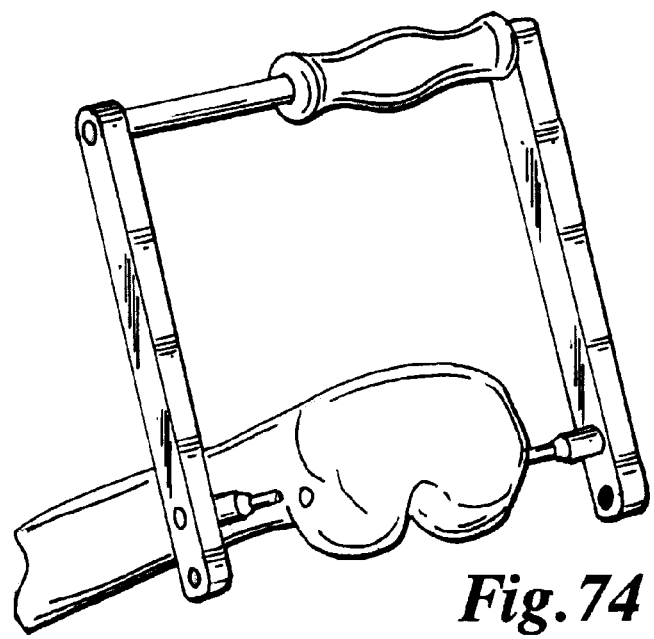
Figure 75:
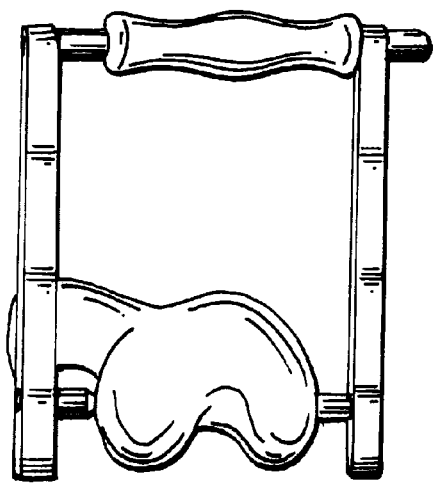

FIGS. 67 through 71 represent ultralow profile PBR embodiments of the present invention, which, as may be seen in comparing FIGS. 69 and 71, lend themselves to minimally invasive implementation while preserving the outstanding clinical performance characteristics of PBR. The embodiment of the milling handle shown utilizes milling handle retaining features of the copending provisional applications referenced herein. As is seen in comparing FIGS. 67 and 68, the cutting guides shown are fixed to bone surfaces located to the sides of bone surfaces to be cut for fixation to the implant. Some surgeons may not want to create such apertures in living tissue that will then have to heal postoperatively. This may be avoided easily by modification of the guide represented in FIG. 68. Instead of creating the apertures in bone to the sides of the cuts, the apertures are formed in bone that will be removed upon completion of the anterior chamfer cut and the posterior chamfer cut. The cutting profile of the cutting guide shown in FIG. 68 would thereby be modified to allow the cutting profile of the cutting tool to traverse a cutting path that, in one embodiment, would complete the anterior cut, a portion of the anterior chamfer cut, the distal cut, and the posterior cut. Completion of any remaining cuts could then be completed in any manner known in the art, such as using the partially cut surfaces as a guide for their completion, attachment of a cutting guide to cut surfaces (such as a conventional chamfer cutting block), or a profiled chisel with cutting surfaces or edge which possessed the exact profile, or resected surface "cutting path", of the cuts to be created and would be plunged across the surfaces being cut in a side to side or mediolateral direction. It should be noted that the profiled chisel embodiment of the present invention would be particularly useful when used in conjunction with the side to side oriented embodiments of Pinplasty style cutting systems, or alternatively, for use with single plate versions of the PBR guides represented herein and/or in the copending applications referenced herein.

Figure 76:
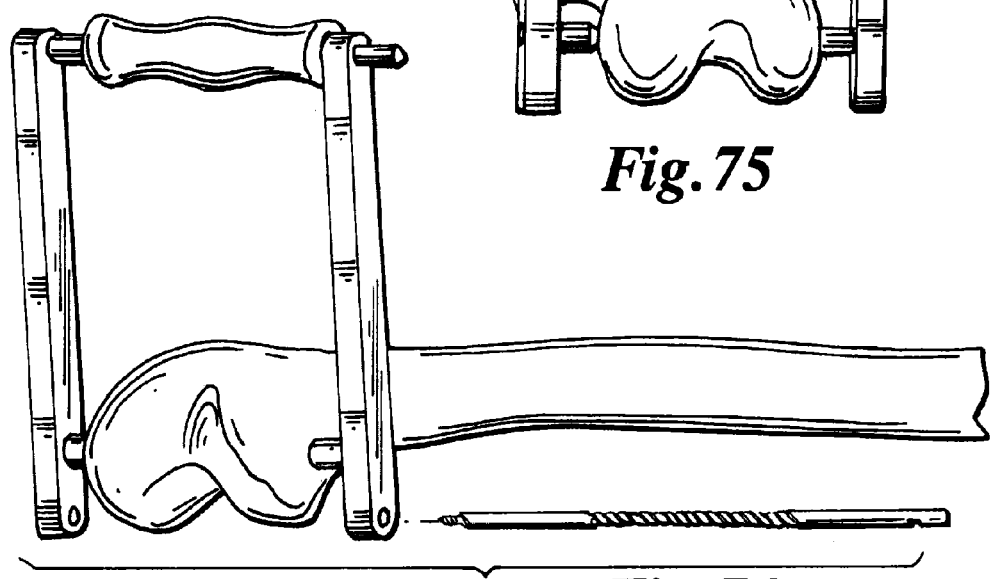
Figure 77:
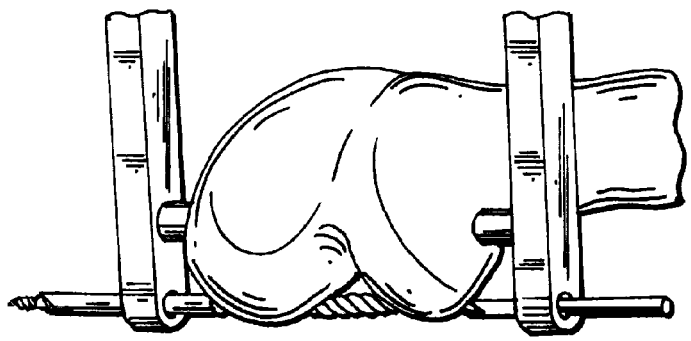
Figure 90:
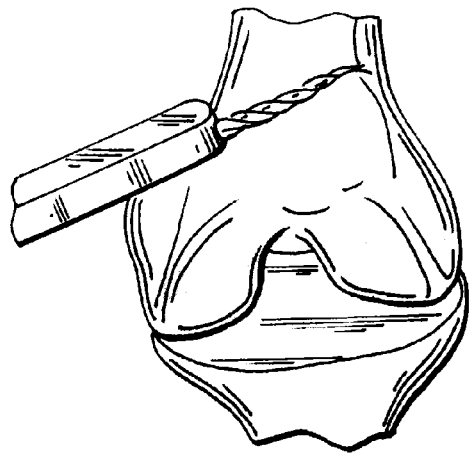

FIGS. 72 through 82 represent embodiments of the present invention for use in Triple TKA or modified Triple Knee Arthroplasty as noted in the copending applications. It is of particular interest to note that the side cutting drill shown in FIG. 80 could be modified to possess and non-linear or curvilinear or curved cutting profile such that it would more closely resemble the side cutting drill shown in FIG. 27 of U.S. Pat. No. 5,810,827. FIG. 76 shows a combination pilot drill and side cutting drill embodiment of the present invention. It is of particular interest to note that although single radius cut per aperture in bone is represented, that multiple radii or even planar cuts are easily generated by modifying the embodiment of the handle shown in FIG. 74 to include a cam or radial displacement mechanism which would continuously or incrementally change the distance from the centerline of the cutter and the centerline of the aperture in response to the angular location of the handle with respect to the bone, as represented in FIG. 79. In other words, the radius changes as a function of angle theta to create the desired cut geometry for fixation of the implant. Any mechanisms enabling precise, controllable axial displacement in response to angular displacement is consider to be within the scope of this embodiment of the present invention.

FIGS. 83 through 92 represent apparatus and methods for use in preparing planar or curvilinear cuts. The embodiments of the sweeping guides (perhaps more precisely described as being "pivotally sweeping guides") shown in FIGS. 83 through 87 were previously described in copending applications referenced herein. Stability of fixation of the cutting guides to the bone is critical in this embodiment as the forces imparted to the bushing must be resisted by the guides lest the resulting cuts vary from their intended location and orientation. One outstanding solution to this issue would be the implementation of a Cam Pin fixation embodiment of the present invention in place of at least one of the fixation nubs shown in FIG. 83. The intent of this cam pin invention is to 'preload' the fixation of the cutting guide to the bone in a manner that allowed the combination of the bone and cutting guide to act as one continuous structure in resisting deflection of the bushing during bone cutting. This desired end result is attained by having at least one of the fixation nubs being rotatably engaged to the cutting guide such that the axis of the cylindrical surface of the fixation nub contacting the guide, and the axis of the cylindrical surface of the fixation nub inserted into the aperture(s) in the bone would NOT be co-axial or collinear, but would instead be parallel but offset by an distance proportional to the preload desired. This offset embodiment of a fixation nub is herein referred to as a "Cam Pin". As an example, FIGS. 83 and 84 show the fixation nubs being inserted into two apertures formed in the bone—lets say these are exactly 0.750 inches apart and 0.158 inches in diameter. In this example, the right most fixation nub shown in FIG. 83 would be integrally formed as part of the cutting guide, but the left most fixation nub is a Cam Pin capable of swinging through an arc of 180 degrees (from a "9 O'clock" direction to a "3 O'clock" direction) with an offset between its guide engagement axis and its bone aperture engagement axis of 0.015 inches. With the cam pin oriented at its 9 O'clock direction, the centerline of the integral fixation nub and the bone engagement axis of the Cam Pin would be exactly 0.750 inches to allow for easy insertion of the guide construct into the fixation apertures. Once inserted, the guide construct is robustly fixed to the bone by turning the Cam Pin to the 3 O'clock position creating a nominal interference condition of 0.030 inches simultaneously preloading the guide construct in tension and the bone in compression. As minor deflection or distortion of the guide construct (and the bone, but to a normally much lesser extent) will result, it may be desirable to design the guide such that its desired configuration is this preloaded or deflected or distorted shape and its nominal, unloading condition is designed accordingly. This Cam Pin embodiment of the present invention is applicable under any circumstances where robust fixation between cutting constructs and bone is desired to ensure accurate and/or precise bone cutting. It should be noted that any degree of preload, in tension or compression modes, could be sought and attained through simple modification of the specific example cited above.

Figure 91:
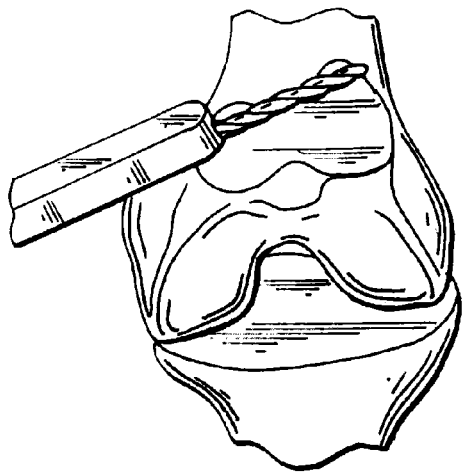
Figure 92:
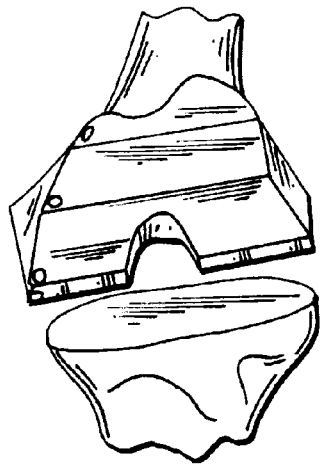
Figure 93:
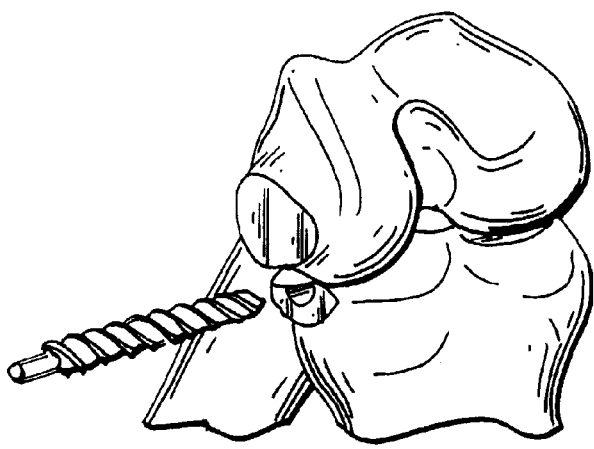

FIGS. 88 through 92 show a technique that will be described as 'guideless cutting' where properly prepared bone surfaces act as the cutting guide. As shown in FIG. 88 and previously described in the herein reference provisional applications, a modified forstner style drill is used, under manual or surg nav guidance, to create the Pivot Aperture and Pivot Reference Surface in the bone. The bushing body is then engaged to these features as indicated in comparing FIGS. 88 and 89 and manipulated to create the cut(s) for attachment to the implant fixation surface(s) as represented in FIGS. 91 and 92. This method is beneficially applied to the application of tibia resection in creating the tibial cut shown in FIG. 92, as well as any other bone surface resection application.

Figure 94:
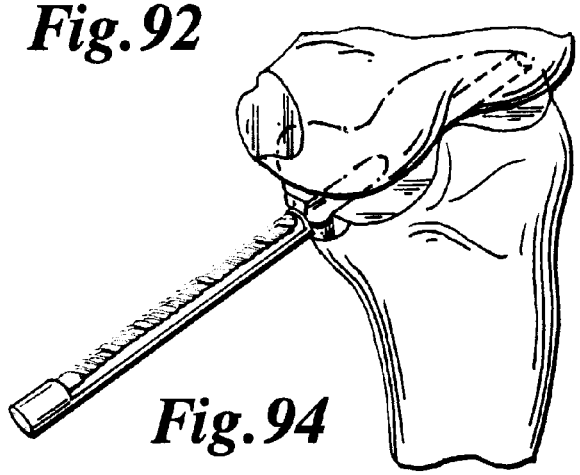
Figure 95:
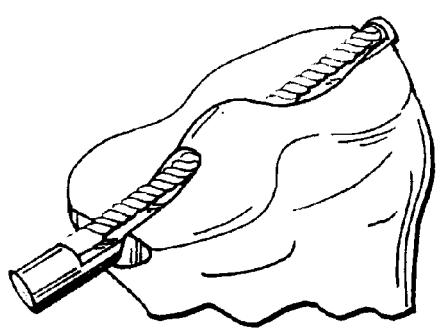
Figure 105:
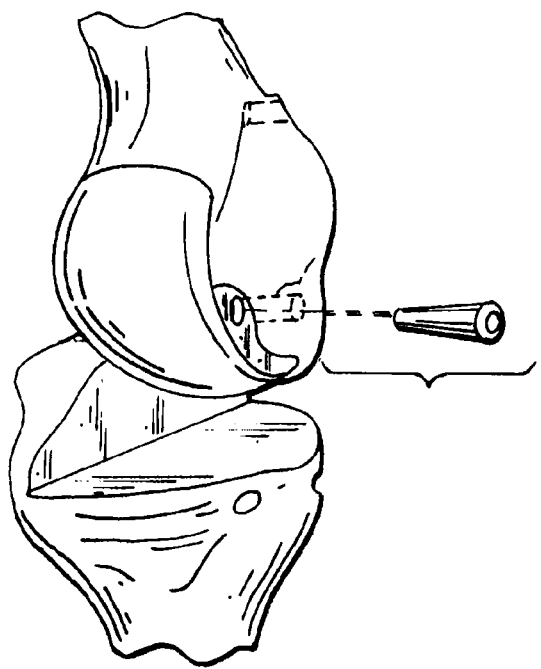

FIGS. 93 through 98 represent a technique previously described in the copending applications, but demonstrating implementation of the side cutting drill embodiment of the present invention for cutting tools. It is of interest to note that the milling handle shown could further be guided by the PBR guides of the present invention to further combine the accuracy and precision benefits of PBR with the soft tissue protection characteristics of tibially embedded femoral cutting tool. It should also be noted that the side cutting drill with a curved cutting profile, similar to that shown in FIG. 119, could also be used to attain cut geometries possessing simultaneously curved or curvilinear cutting profiles and cutting paths. In utilizing such, it would be critical that the side to side location of the cutting profile of the cutting tool be tightly controlled with respect to the desired side to side location of the implant as the side to side location of the implant would be dictated by the cut surfaces generated. Alternatively, a cutting tool with a linear cutting profile, as shown in FIG. 94, could be utilized to create cut surfaces with a linear cutting profile and a curved cutting path, and then a second cutter with a curved cutting profile could be used to create a second, contiguous or noncontiguous, cut with a curved cutting profile and/or path whose mediolateral location was closely controlled to result in proper fit and location of the prosthesis attached to said cut surfaces. It should be noted that the cutting path of the second cutter could be located within a single plane, such as for a bilateral femoral component design, or could be curvilinearly divergent from the plane containing the cutting path of the first cut surface. This would be useful for unilateral femoral component designs (ones which require separate left and right femoral implants) so as to allow for the implant design to reflect out of plane patellofemoral kinematics and/or out of plane tibiofemoral kinematics most accurately. Interestingly, this embodiment of kinematic resection style resection could be modified to allow the cutting tool to be directly or indirectly linked to the movement of the patella with respect to the femur, or directly connected to the patella, to enable cutting of patellofemoral articular surfaces on the femur while moving the tibia and patella through ranges of motion about the tibia. The embodiments of cutting tools for use in attaining this include curvilinear end cutting mills or face cutters, side cutting drills with linear or non-linear cutting profiles, and other cutting tools capable of cutting the femur while engaged, directly or indirectly, to the patella. The side-to-side location of such cutters could be determined by engagement or adjustment with respect to a PBR or other guide, or simply by the natural kinematic path of the patella about the femur during flexion-extension of the knee joint.

FIGS. 99 through 112

FIGS. 99 through 127 generally represent prosthesis and prosthesis fixation feature embodiments for use with the PBR embodiments of the present invention. While there are particular advantages to these implant prosthesis, it will also be recognized that conventional implant prothesis or implant prosthesis of alternate designs can also be used with the PBR embodiments of the present invention.

FIGS. 99 through 102 show representations of a tongue in groove fixation feature applied to a Unicondylar femoral component enabling anterior insertion of one tongue element into a 't-slot' style groove formed in bone and a progressively increasing press fit obtained by forcing the implant posteriorly, as is represented in comparing FIGS. 99 and 100. The t-slot feature, or groove, formed in the femur is easily formed by, in one embodiment, providing a trial component possessing a contoured groove and slot for guiding a t-slot cutter along its length. Such a contour groove would be responsible for controlling the depth of the t-slot in the bone with respect to the cut surface to which the implant fixation surface is attached, while the slot in the trial would dictate the mediolateral location of the t-slot style groove. It is likely necessary to include an aperture in the slot and/or contour groove in the trial component to allow for insertion and plunging of the wider T cutting surfaces prior to sweeping.

Figure 106:
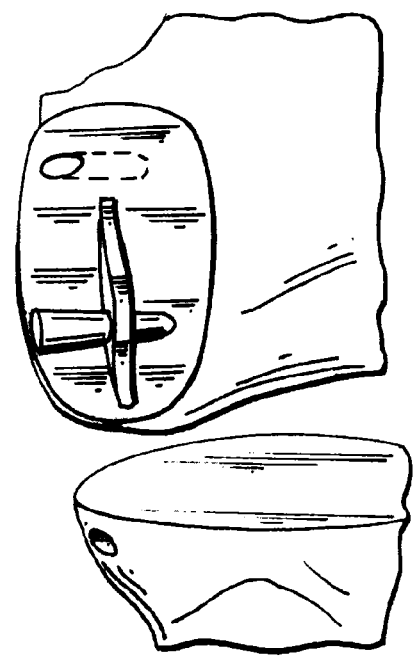

Alternatively, FIGS. 103 through 112 represent combinations of finned and/or crosspinned implants. It should be noted that the AP Fin Profile of the fin may be linear as shown in FIG. 106 (in other words, the fin may be may be planar), or it could be slightly tapered to achieve an interference fit with the walls of the groove as the implant fixation surfaces are forced into contact with the cut surfaces to which they are mated (see FIGS. 107 through 109), or in could be curved as looked at from the viewpoint of FIG. 106 to further provide stability of fixation. Interestingly, the fixation aperture created to fix a cutting guide to the bone could be utilized to cross pin a flange or fin of a femoral prosthesis. It should be noted that although the embodiment shown is a Unicondylar femoral prosthesis, this concept could be applied to tibial, femoral, or patellofemoral prostheses in any application, or in other joint, trauma, spine, or oncology procedures, as is generally represented in FIGS. 120 through 127. In FIGS. 105 through 112, a tapered pin is used to engage the cross pin hole in the fin of the prosthesis. The tapered pin may be utilized to facilitate a resulting press fit between the pin and the fixation surfaces of the implant and/or ease of introducing the pin into the hole in the fin. The pin could be of any known material, but resorbable materials are especially interesting in as they are 'consumed' by the body leaving minimal hardware within the body after a fairly predictable amount of time has passed. PLA/PGA compositions, Tricalcium Phosphate, allograft and autograft bone, bone substitutes, and the aforementioned slurry type compositions may serve well. Alternatively, bone cement or other liquid or semi-liquid material may be injected into the portals/apertures to achieve intimate interdigitation, and the crosspins optionally inserted thereafter, but prior to complete hardening or curing. Alternatively, the crosspin(s) could be hollow with radially extending holes allowing the pins to be inserted and then have bone cement injected into them and up under the implant. Alternatively, the cross pin could be threaded to engage threads in the fin, or to engage the bone (both for short term stability and to facilitate removal) or both. These embodiments hold significant promise in both providing for intraoperatively stable cemented or cementless fixation as well as facilitating long term biological ingrowth. It should be noted that the use of multiple holes, pins, and apertures in the prosthesis could be used and that the holes in the bone need not be fixation holes to which guides are attached. Also it should be noted the condylar sections, and patellofemoral sections of the implant could be wholly separate, modularly joined, be composed of a dual condylar prosthesis and separate patellofemoral prosthesis, or any combination of the above. Although the bone/implant interface shown is curved in two planes, these concepts apply to implants with 3 planar curved geometry (where the cutting path and cutting profiles of the resected surface geometry and therefore the fixation surface geometry do not remain in two planes through the entirety of the cutting path, or where the cutting path is contained within multiple or single curved surfaces), entirely planar geometries, or anything in between.

Figure 107:
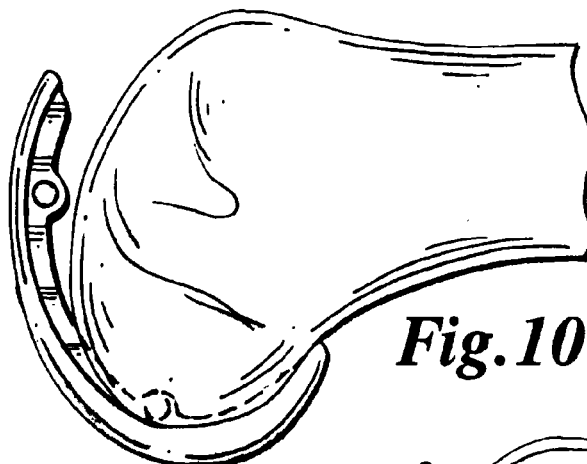
Figure 108:
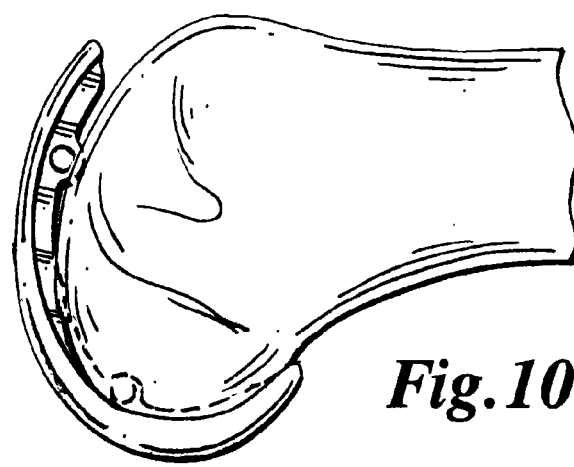
Figure 109:
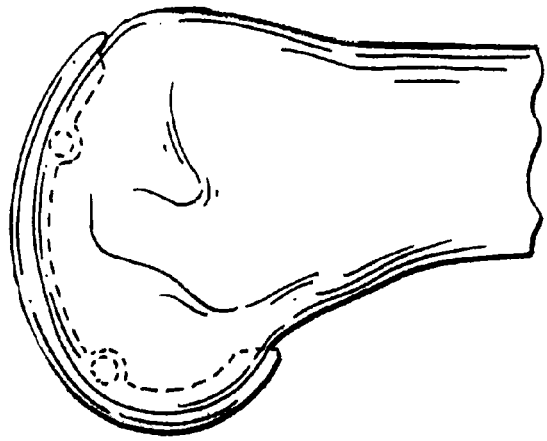
Figure 110:
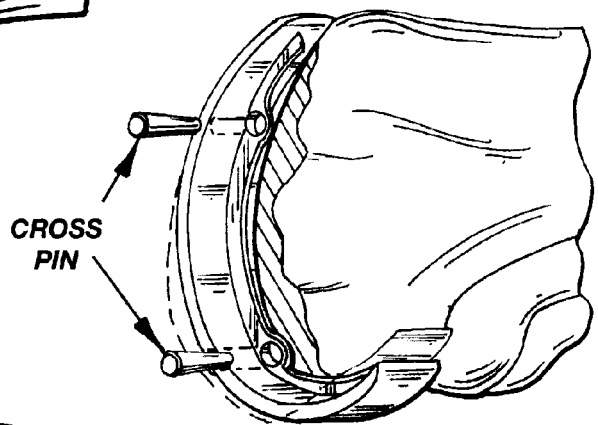

FIGS. 107 through 112 demonstrate another embodiment of an implant prosthesis for use with the present invention allowing for benefits well above and beyond those of the prior art. This will be referred to herein as a BMO Prosthesis or BMO Cortical type implant (Biomechanical Optimization Prosthesis). This embodiment has several applications. For instance, if the resected surfaces are going to vary significantly from the fixation surface geometries, as may be seen in unguided kinematic resection, it may be advantageous to implement fixation surface geometries that can conform to variation in resection geometry. Most implant materials in joint replacement are rigid, and that their rigidity is a desirable characteristic for achieving stable fixation. In the case of surface replacement, however, the present invention recognizes that this is not necessarily the case. Very thin (less than 3 mm thick, probably closer to a range of 1.5 to 0.01 mm thick) sections of many metals, including implant grade metals and alloys cobalt chrome, titanium, zirconium, and liquid metal, can be processed into very thin forms capable of conforming to variations in the resected surface and yet still have bearing surfaces that are highly polished and provide significant contact area, where desirable, for bearing against the bearing or articular surfaces of the opposing implant. The construct or prosthesis resulting from applying this concept to a femoral component in Unicondylar knee replacement may start out being a 1" wide be 3" long strip of 1.5 mm thick material curved in a manner to generally look like the curved cutting path and curved cutting profile of a natural, healthy femur. A process such as Tecotex from Viasys Healthcare of Wilmington, Mass. could be used to remove material from the strip down to a nominal thickness of perhaps 0.1 mm thick (or other thickness determined optimal via investigation) while leaving protruding 'hooks' (almost like the hook and eye concept of Velcro) emerging from the thin fixation surface to engage the bone. One or more fins could be attached or be a continuous part of this construct as shown in FIG. 107. During insertion, the anterior most cross pin could lock that portion of the prosthesis in place, then the prosthesis could be wrapped around the remaining, more posteriorly resected surfaces and the posterior cross pin inserted (see FIG. 111). Alternatively, the fins could be located about the periphery of the articular surfaces of the condyle in the form of tabs and the cross pins or screws or tapered dowels, etc. known in the art inserted through holes in the tabs and into bone to fix the Cortical implant. The combination of fins and tabs may also be useful. In using the tabs it is critical to keep all features of the implanted device ultralow profile to avoid irritating the surrounding soft tissues (perhaps creating recesses in the bone underlying the tabs would be desirable to allow for a form of countersinking of the tabs and/or the pins or screws or other fixation devices). The flexibility of the implant would allow it to conform to the resection surface and the stability of the crosspin fixation would assist in reducing interfacial micromotion known to inhibit bone ingrowth and fixation (this concept could be used with PMMA, but it would be desirable to avoid the tissue necrosis and bone preservation for revisional issues associated with the use of bone cement if the patients health/comorbidities/indications allow). This kind of implant could have some very interesting clinical benefits beyond simple bone preservation. Given how well this kind of implant would impart load to underlying bone, thus avoiding stress shielding, it is possible not only to promote healthy bone ingrowth into and around the interfacial features, but the bearing contact and strains/stresses imparted to the bone could motivate the bone to change its shape (and therefore the shape of the implant—its flexible, remember?) to ideally conform to the tibial component bearing surface such that bearing stresses are carried through the broadest desirable contact area (just like modeling/remodeling in a healthy unmodified joint).

Figure 113:
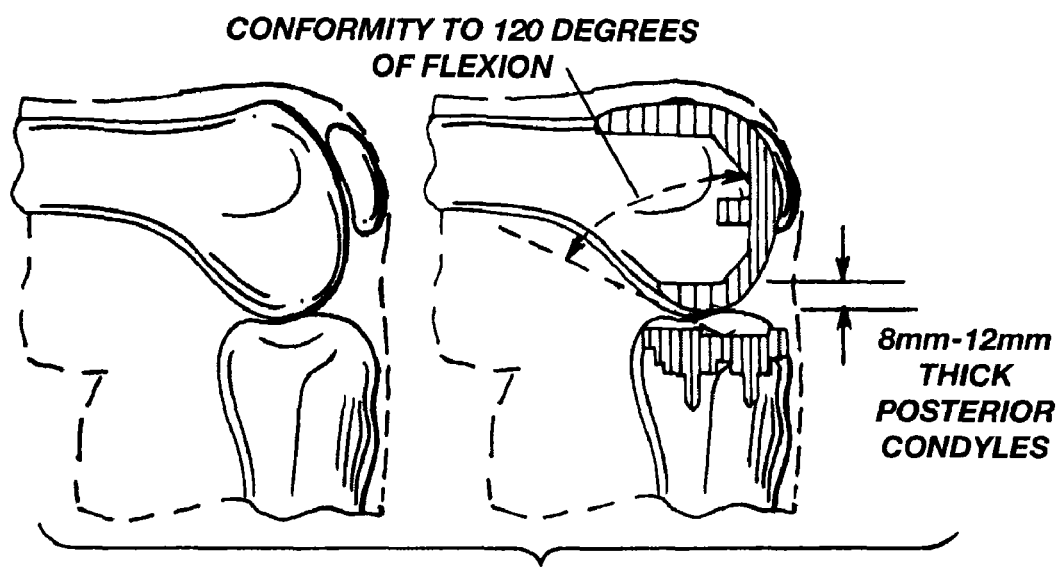
Figure 114:
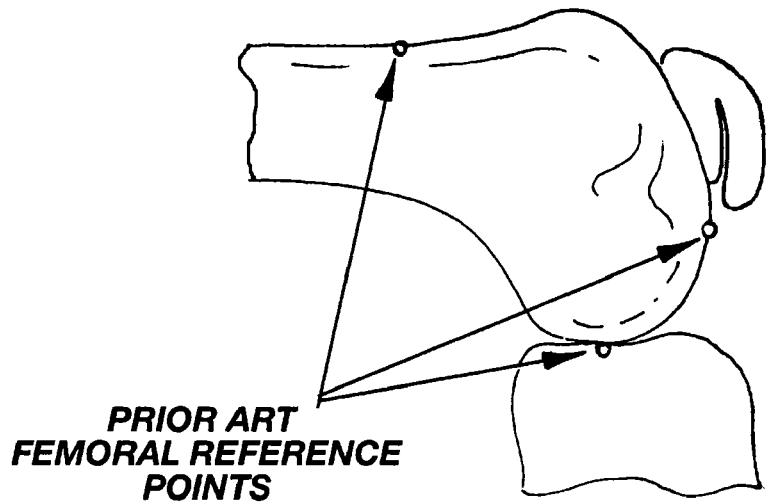
Figure 115:
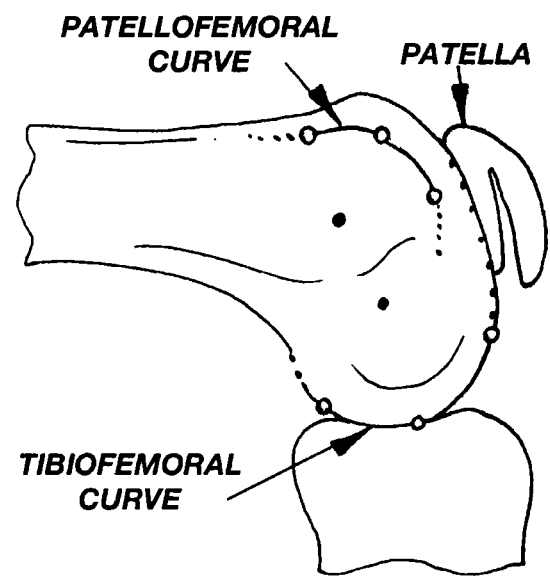
Figure 123:
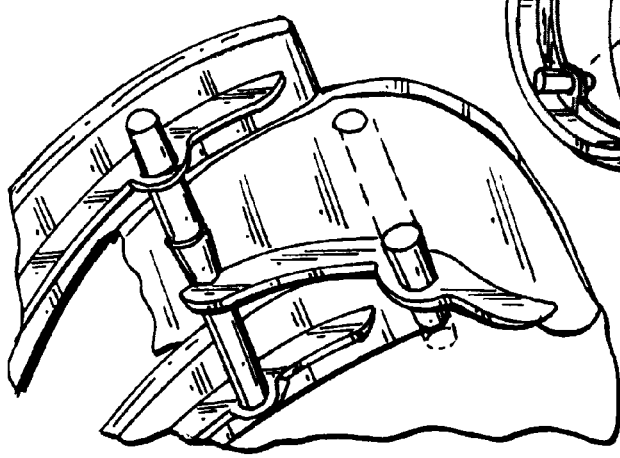
Figure 124:
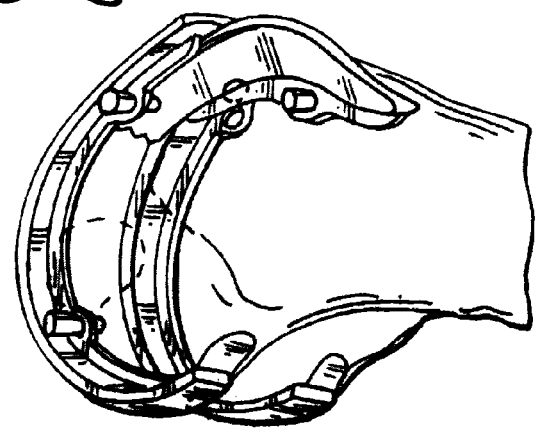
Figure 128:
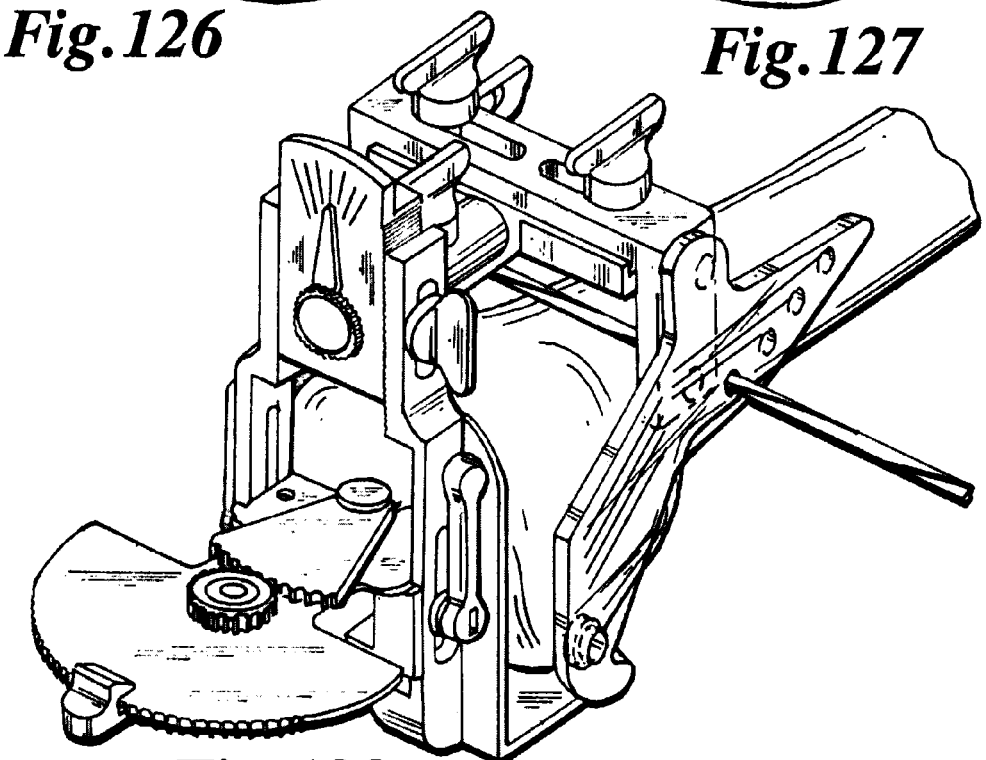

FIGS. 113 through 115 are an embodiment of the present invention that may prove to be a very usefully alternative to conventional rectilinear based referencing techniques. In essence, conventional alignment techniques, once having established appropriate flexion extension angulation and varus valgus angulation of desired implant location, reference the anterior cortex, distal most femoral condylar surface, and posterior most condylar surface (indicated in FIG. 114 by stars) to dictate the anterior posterior location, proximal distal location (otherwise known as distal resection depth), and appropriate implant size in determining the 'perfect' location and orientation for the appropriately sized implant (mediolateral location is normally 'eyeballed' by comparison of some visual reference of the mediolateral border surrounding the distal cut surface and some form of visual guide reference). These conventional techniques fail to directly reference the distinctly different anatomic bone features which dictate the performance of distinctly separate, but functionally interrelated, kinematic phenomena, and they also attempt to reference curvilinear articular surfaces by way of rectilinear approximations. The embodiment of the present invention is an alternative alignment technique with an object to overcome the errors inherent in prior art. As shown in FIG. 115, the femur possesses two distinct kinematic features and functions that lend themselves to physical referencing; the patellofemoral articular surface and the tibiofemoral articular surfaces, both of which are curved, more specifically these surfaces represent logarithmic curves. The one codependency between the two articular functions, and therefore any geometric approximation made of them in referencing, is that they must allow for smooth kinematically appropriate articulation of the patella as it passes from its articulation with the trochlear groove (shown in blue in FIG. 115) to its articulation with intercondylar surfaces between the femoral condyles (shown in red in FIG. 115). Thus, knowing that three points define an arc and may be used to approximate a curve or sections of a curve, what is proposed is to use a referencing device which contacts at least one femoral condyle at three points to determine both an approximation of arc radius and centerpoint location, while independently or simultaneously referencing the trochlear groove at three points to determine both an approximation of arc radius and centerpoint location. The referencing system would further need to provide for the need of the articular surfaces of the trochlear articular surfaces to smoothly transition to those of the intercondylar surfaces. Armed with this information, a surgeon may most appropriately determine appropriate implant location and orientation. This embodiment of the present invention is especially useful in determining the proper location, orientation, and implant size for the modular tricompartment components shown in FIGS. 120 through 124, the non-modular implants shown in FIGS. 125 through 127, and standard implants where the appropriate size, location, and orientation would be determined by that which best mimics existing articular bone surfaces thus resulting in optimal postoperative kinematic function. FIG. 123 represents one method of fixing the patellofemoral implant with respect to the condylar implant(s) so as to maintain smooth transitional articulation. It should be noted that this crosspin method of interconnecting the separate components could be augmented by tongue and groove interlocking between the medial side of the condylar component shown and the lateral side of the patellofemoral component shown. What is critical is that the transition between the patellofemoral component and the condylar component surfaces responsible for patellofemoral articulation are and remain tangent at least one point. FIGS. 128 and 129 represent an alignment guide that could be easily modified to accomplish the aforementioned 3 point referencing by addition or inclusion of dedicated or modular referencing means.

FIG. 119 is a graphical representation of an offset power input for a milling handle embodiment of the present invention. It should be noted that the mechanism represented by the yellow lines/arcs could be a chain, belt, spur gear, or other rotary power transmission linkage. This allows for a milling handle design that allows for the distal ends of the arms to be deeply inserted into a wound without the drive input displacing soft tissue (as somewhat shown in FIG. 71).

FIG. 130 represents a distal femur with the cuts shown for fixation to a conventional total condylar implant with the border of said cuts shown in black.

FIGS. 131 through 146

FIGS. 131 through 146 show embodiments of the present invention for cutting the distal and posterior areas of the femur.

Figure 133:
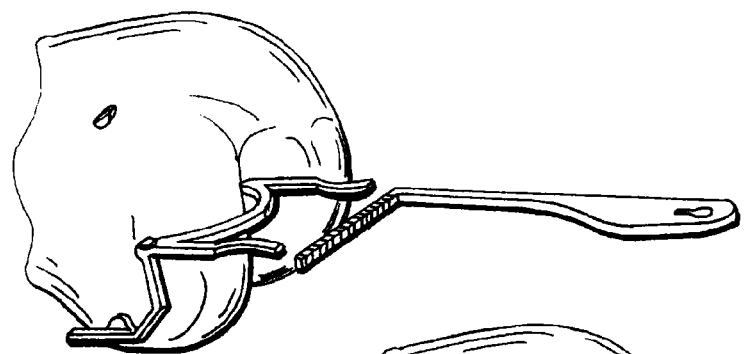
Figure 134:
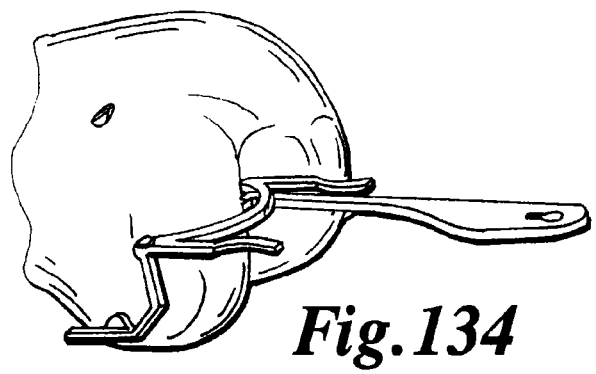
Figure 135:
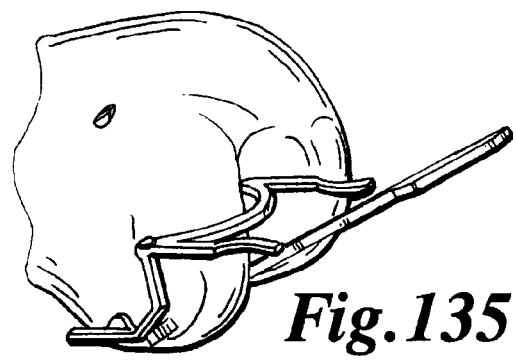

FIGS. 131 and 132 show an embodiment of the present invention constituting an improved oscillating saw design. As shown, this design possesses cutting teeth not only on the leading edge as is commonly known in the art, but also on an adjacent surface allowing the saw to cut both while plunging in a direction parallel its long axis and normal to its long axis. FIGS. 133 through 134 show this in use with a cutting guide in cutting the femur. It should be noted that the two smoother areas surrounding the cutting teeth of the saw are intended for bearing contact with a guide, but that bushings, or bearings could be added to facilitate ease of use and avoidance of debris generation.

Figure 136:
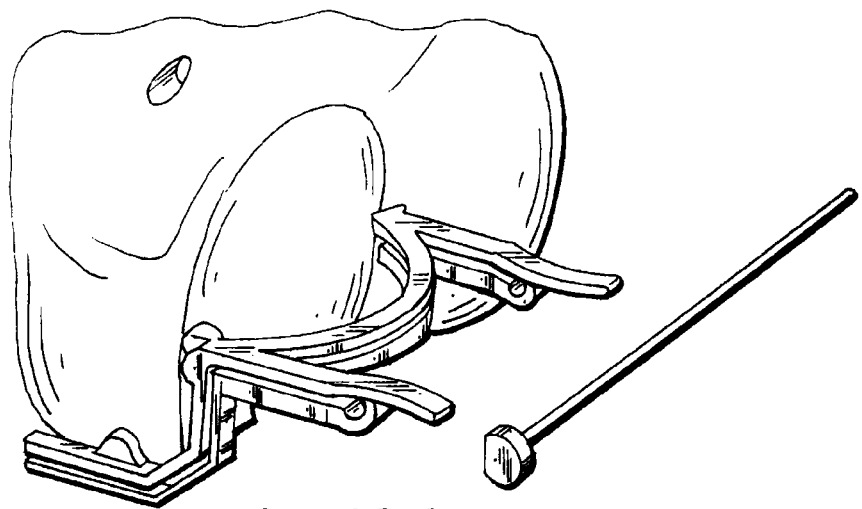
Figure 137:
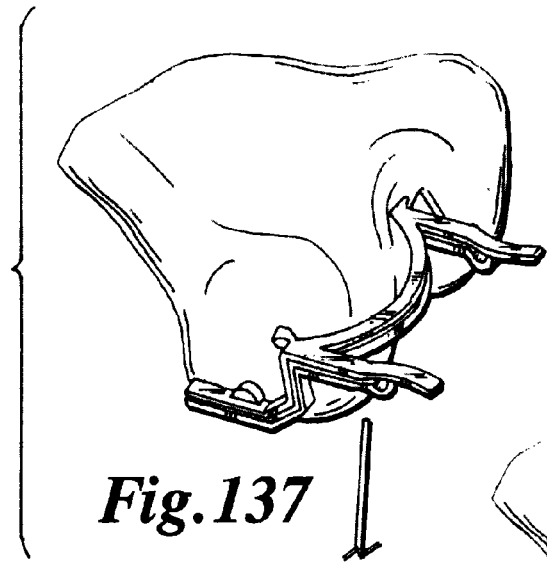
Figure 138:
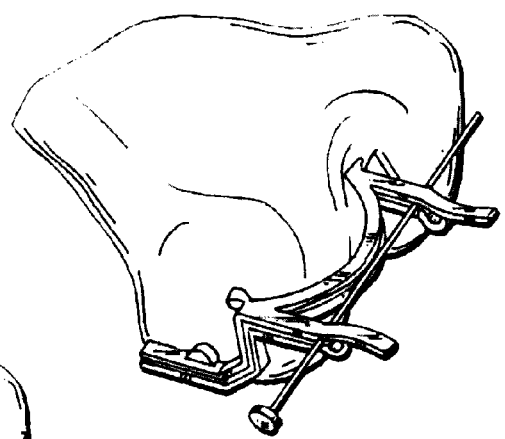
Figure 139:
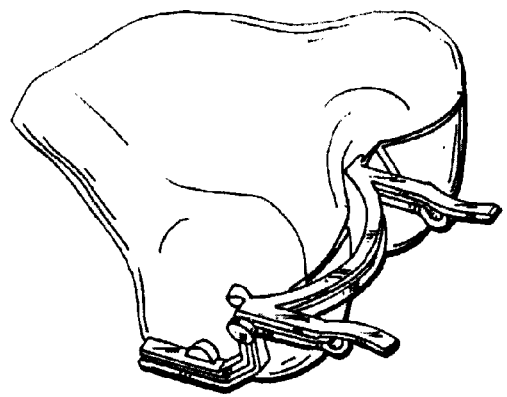
Figure 140:
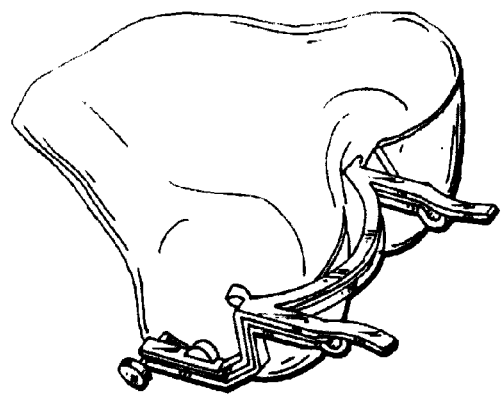
Figure 141:
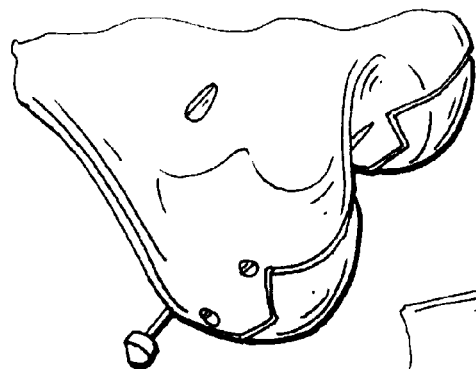
Figure 142:
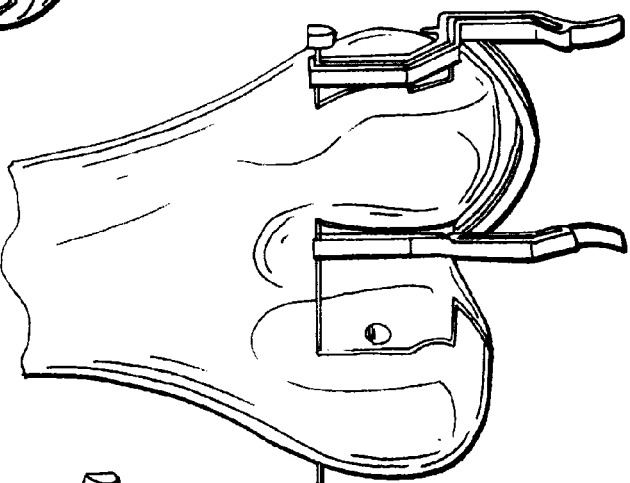
Figure 143:
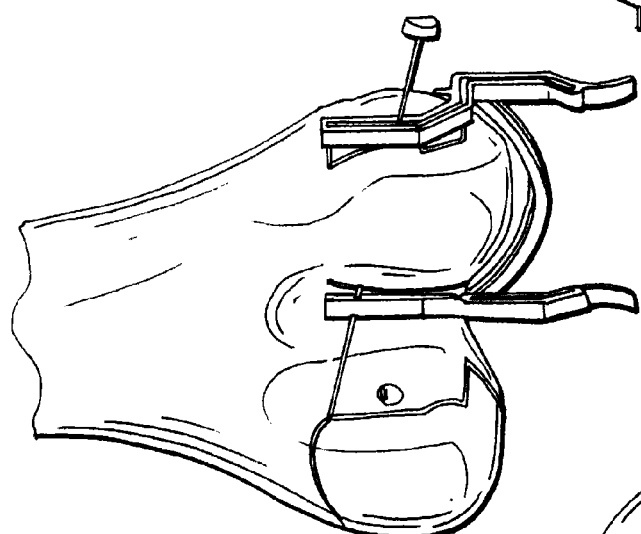
Figure 144:
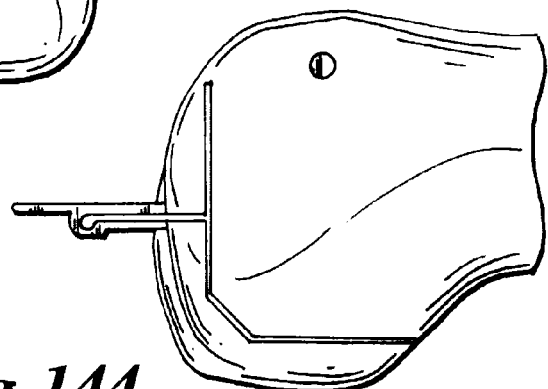
Figure 145:
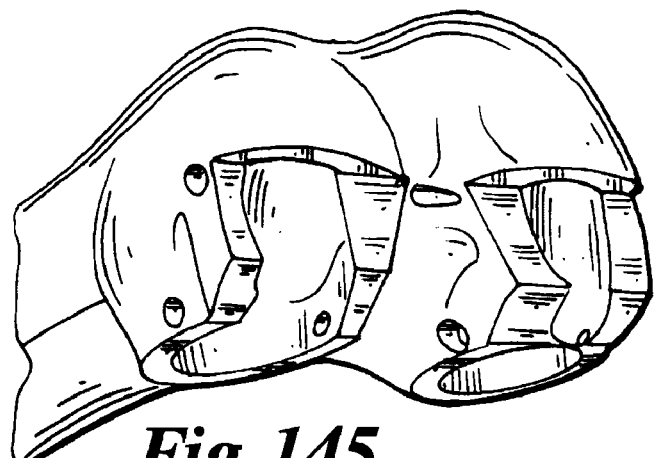
Figure 146:
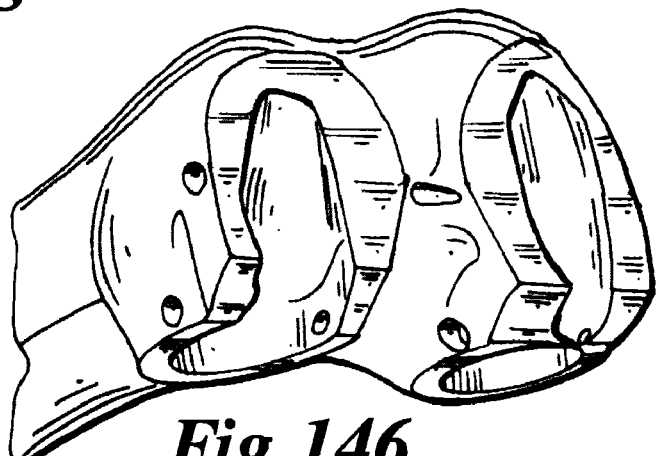
Figure 147:
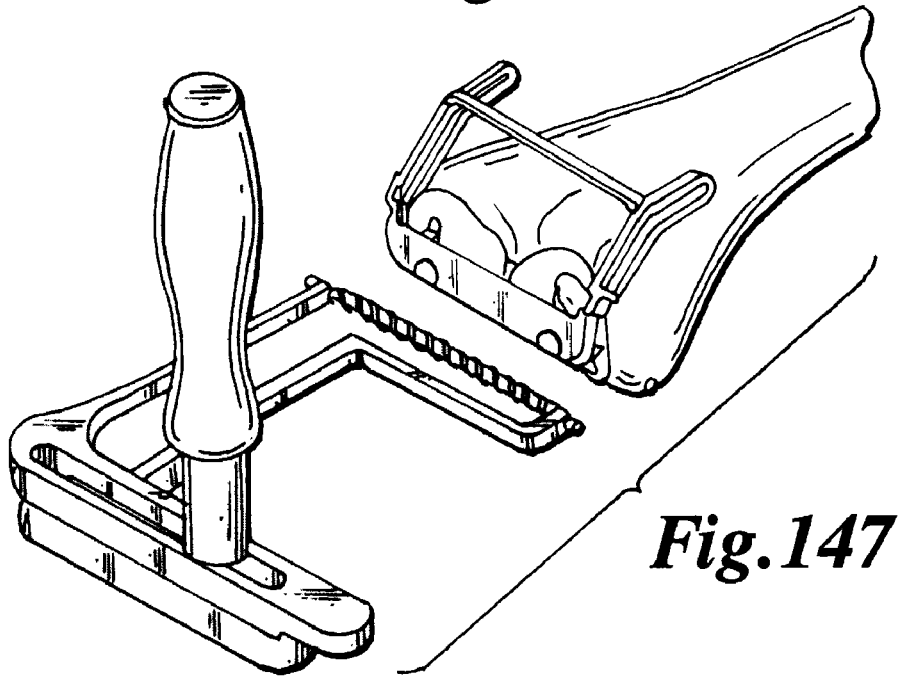
Figure 148:
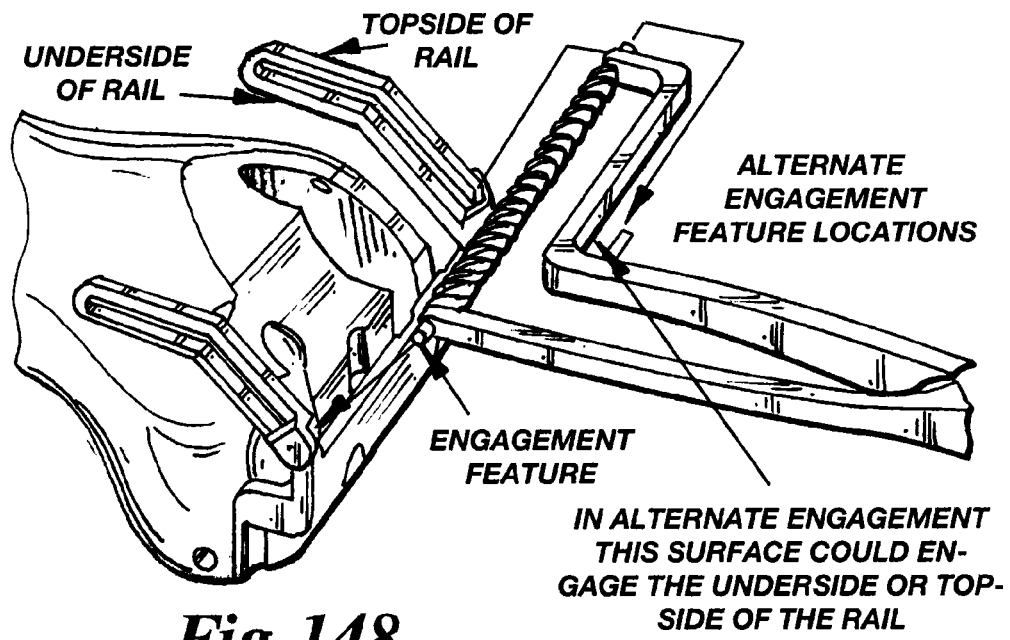
Figure 149:
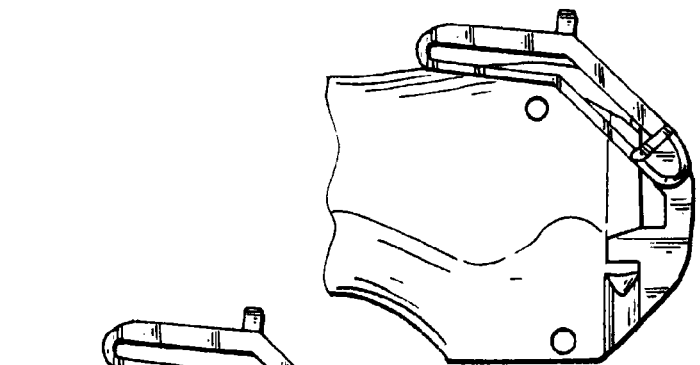
Figure 150:
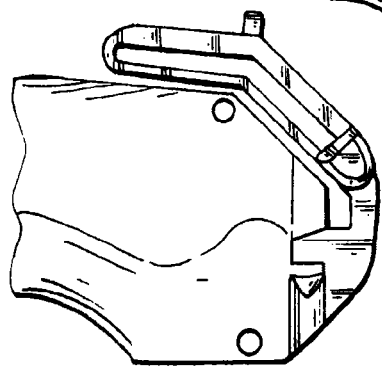
Figure 151:
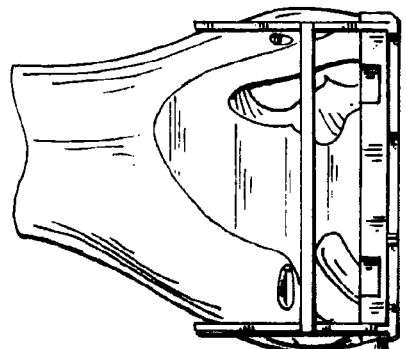
Figure 157:
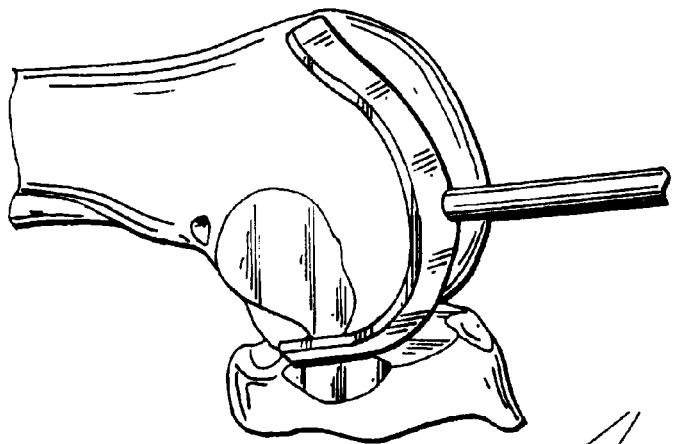
Figure 158:
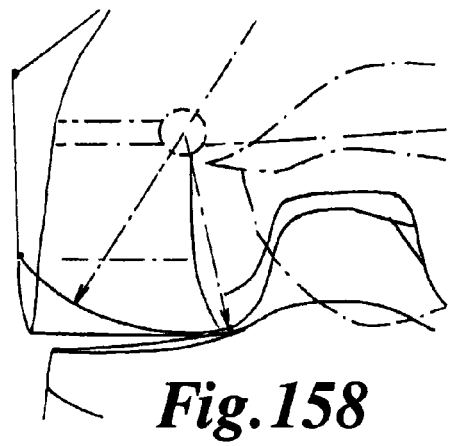
Figure 159:
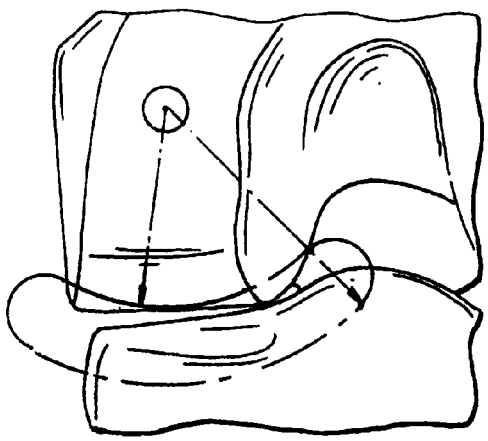
Figure 160:
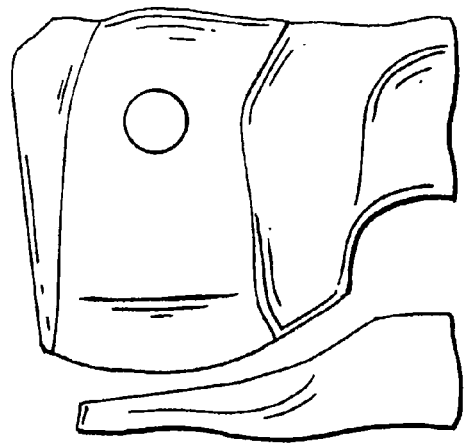
Figure 166:
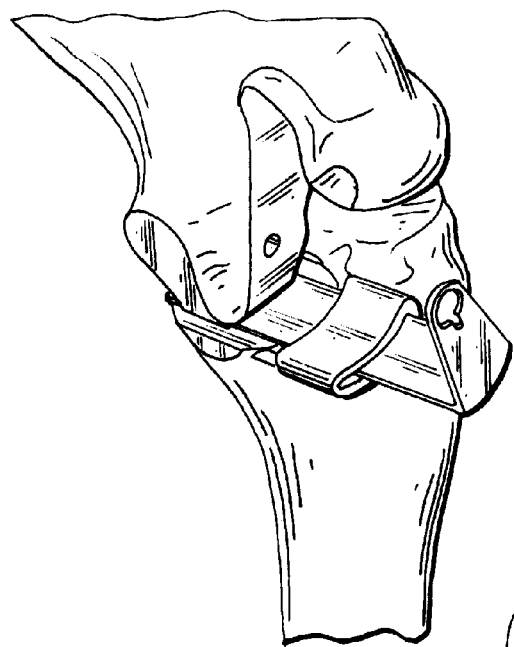
Figure 167:
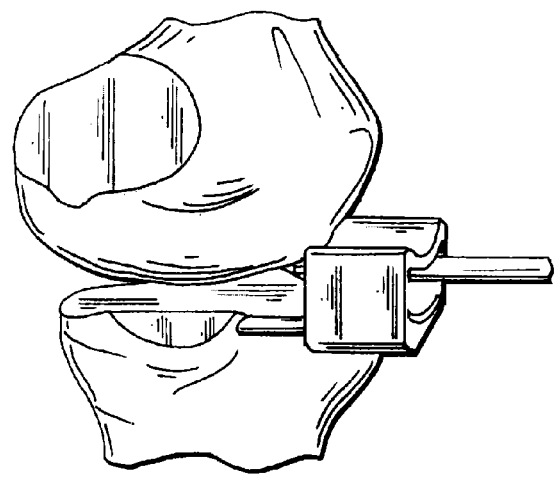
Figure 168:
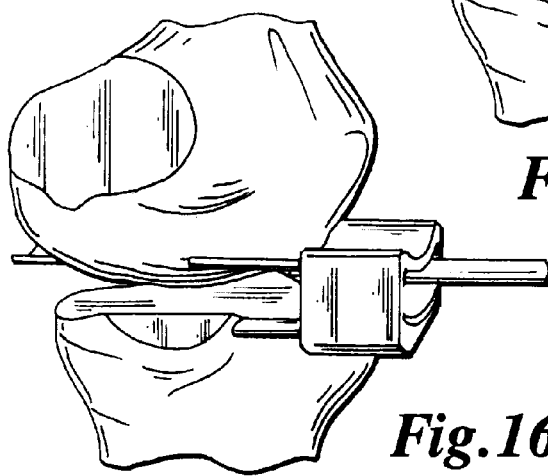

FIGS. 136 through 146 show an alternative cutting means. The small cutting tool best shown in FIG. 136 is a small diameter (0.188 inches to 0.040 inches) side cutting drill, optionally for use in conjunction with a milling handle (not shown). As shown in these figures, a robustly guided cutting tool can be used to cut both condyles when guided by a guide either straddling only one condyle (as shown), or fixed to the medial side of the lateral condyle and the lateral side of the medial condyle. These embodiments may also be applied to cutting of only one condyle, and the cutting path of the guide shown modified to allow for standard or improved Unicondylar use. Also shown, the manipulation of the cutting tool while guided by a PBR guide can include plunging, sweeping and pivotally sweeping manipulations in completing the desired cuts. Once these cuts have been completed, or partially completed and finished by other means, as shown in FIGS. 145 and 146, alternate methods may be employed to complete the remaining cuts. It should be noted that methods allowing for the resection of the posterior femoral condyles and/or the distal femoral condyles in conjunction with the proximal tibia already having been cut, provide for a phenomenal amount of laxity of the soft tissues surrounding the joint allowing for a surgeon to more easily complete cutting of the anterior cut and anterior chamfer cut.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed is:

1. A method of implanting an orthopedic prosthesis during knee arthroplasty surgery, comprising:
   providing a femoral prosthesis having a fixation surface for facing a femur and an articulation surface adapted to articulate with a surface associated with a tibia;
   positioning opposing guide patterns along opposing sides of a distal portion of the femur, the guide patterns possessing cutting tool guide surfaces geometrically corresponding to a geometry of the fixation surface of the femoral prosthesis;
   fixing the opposing guide patterns in position relative to the femur;
   positioning a cutting tool mediolaterally between the femur and the tibia;
   engaging the cutting tool with the cutting tool guide surfaces;
   manipulating the tibia through a range of motion about the femur while simultaneously actuating the cutting tool to cut the femur to form a resected surface for the femoral prosthesis; and
   operably attaching the femoral prosthesis to the resected surface.

2. The method of claim 1, wherein the step of manipulating the tibia through a range of motion about the femur while simultaneously actuating the cutting tool includes preventing a cutting profile of the cutting tool from being exposed to soft tissue regions adjacent respective sides of the femur with a pair of soft tissue protective sleeves, each soft tissue protective sleeve surrounding the cutting tool proximate one of the soft tissue regions and biased to track along a contour of one of the sides of the femur.

3. The method of claim 1, wherein the step of actuating the cutting tool to cut the femur to form a resected surface for the femoral prosthesis is accomplished with a single pass of the cutting tool.

4. The method of claim 1, wherein the step of actuating the cutting tool to cut the femur to form a resected surface for the femoral prosthesis is accomplished with two passes of the cutting tool.

5. The method of claim 1, wherein the step of fixing the opposing guide patterns in position relative to the femur includes extending fixation features from the guide patterns into holes in the femur through an incision in soft tissue adjacent the femur.

6. The method of claim 5, wherein the step of fixing the opposing guide patterns in position relative to the femur includes fixing the opposing guide patterns such that only the fixation features extend through the incision.

7. A method for implanting an orthopedic prosthesis during knee arthroplasty surgery comprising:
   providing a femoral prosthesis having a fixation surface for facing a femur and an articulation surface adapted to articulate with a surface associated with a tibia;
   positioning a medial guide pattern along a medial side of a distal portion of the femur, the guide pattern possessing cutting tool guide surfaces geometrically corresponding to a geometry of the fixation surface of the femoral prosthesis;
   fixing the medial guide pattern in position relative to the femur;
   positioning a cutting tool mediolaterally between the femur and the tibia;
   engaging the cutting tool with the cutting tool guide surfaces;
   manipulating the tibia through a range of motion about the femur while simultaneously actuating the cutting tool to cut the femur to form a resected surface for the femoral prosthesis; and
   operably attaching the femoral prosthesis to the resected surface.

8. The method of claim 7, wherein the step of manipulating the tibia through a range of motion about the femur while simultaneously actuating the cutting tool includes preventing a cutting profile of the cutting tool from being exposed to soft tissue regions adjacent respective sides of the femur with a pair of soft tissue protective sleeves, each soft tissue protective sleeve surrounding the cutting tool proximate one of the soft tissue regions and biased to track along a contour of one of the sides of the femur.

9. The method of claim 7, wherein the step of actuating the cutting tool to cut the femur to form a resected surface for the femoral prosthesis is accomplished with a single pass of the cutting tool.

10. The method of claim 7, wherein the step of actuating the cutting tool to cut the femur to form a resected surface for the femoral prosthesis is accomplished with two passes of the cutting tool.

11. The method of claim 7, wherein the step of fixing the medial guide pattern in position relative to the femur includes extending fixation features from the guide pattern into holes in the femur through an incision in soft tissue adjacent the femur.

12. The method of claim 11, wherein the step of fixing the medial guide pattern in position relative to the femur includes fixing the guide pattern such that only the fixation features extend through the incision.

13. A method for implanting an orthopedic prosthesis during knee arthroplasty surgery comprising:
   providing a femoral prosthesis having a fixation surface for facing a femur and an opposing articulation surface adapted to articulate with a surface associated with a tibia;
   creating an incision in soft tissue adjacent to a distal portion of the femur;
   positioning a guide pattern adjacent to the incision, the guide pattern possessing cutting tool guide surface geometrically corresponding to a geometry of the fixation surface of the femoral prosthesis;
   fixing the guide pattern in position relative to the femur;
   positioning a cutting tool mediolaterally between the femur and the tibia;
   engaging the cutting tool with the cutting tool guide surfaces;
   manipulating the tibia through a range of motion about the femur while simultaneously actuating the cutting tool to cut the femur to form a resected surface for the femoral prosthesis; and
   operably attaching the femoral prosthesis to the resected surface.

14. The method of claim 13, wherein the step of engaging the cutting tool with the cutting tool guide surfaces includes extending a soft tissue protective sleeve surrounding a portion of the cutting tool through the soft tissue and into contact with the femur.

15. The method of claim 14, wherein the step of manipulating the tibia through a range of motion about the femur while simultaneously actuating the cutting tool includes maintaining the soft tissue sleeve in contact with the femur.

16. The method of claim 13, wherein the step of actuating the cutting tool to cut the femur to form a resected surface for the femoral prosthesis is accomplished with a single pass of the cutting tool.

17. The method of claim 13, wherein the step of actuating the cutting tool to cut the femur to form a resected surface for the femoral prosthesis is accomplished with two passes of the cutting tool.

18. The method of claim 13, wherein the step of fixing the guide pattern in position relative to the femur includes extending fixation features from the guide pattern through the incision into holes in the femur.

19. The method of claim 18, wherein the step of fixing the guide pattern in position relative to the femur includes fixing the guide pattern such that only the fixation features extend through the incision.

* * * * *